US012637492B2

(12) United States Patent
Marlowe et al.

(10) Patent No.: US 12,637,492 B2
(45) Date of Patent: May 26, 2026

(54) PEPTIDE INHIBITORS OF FOCAL ADHESION KINASE ACTIVITY AND USES THEREOF

(71) Applicant: Arizona Board of Regents on Behalf of the University of Arizona, Tucson, AZ (US)

(72) Inventors: Timothy Marlowe, Phoenix, AZ (US); Warren S. Weiner, Phoenix, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 1005 days.

(21) Appl. No.: 17/638,930

(22) PCT Filed: Aug. 31, 2020

(86) PCT No.: PCT/US2020/048827
§ 371 (c)(1),
(2) Date: Feb. 28, 2022

(87) PCT Pub. No.: WO2021/042064
PCT Pub. Date: Mar. 4, 2021

(65) Prior Publication Data

US 2022/0306692 A1 Sep. 29, 2022

Related U.S. Application Data

(60) Provisional application No. 62/894,726, filed on Aug. 31, 2019.

(51) Int. Cl.

| | |
|---|---|
| ***C07K 7/64*** | (2006.01) |
| ***A61K 38/12*** | (2006.01) |
| ***A61K 45/06*** | (2006.01) |
| ***A61K 47/60*** | (2017.01) |
| ***A61K 49/00*** | (2006.01) |

(52) U.S. Cl.
CPC ................ *C07K 7/64* (2013.01); *A61K 38/12* (2013.01); *A61K 45/06* (2013.01); *A61K 47/60* (2017.08); *A61K 49/0041* (2013.01)

(58) Field of Classification Search
None
See application file for complete search history.

(56) References Cited

U.S. PATENT DOCUMENTS

| | | | |
|---|---|---|---|
| 2009/0239850 A1 | 9/2009 | Cance et al. | |
| 2013/0022594 A1 | 1/2013 | Holmes et al. | |
| 2016/0251696 A1 | 9/2016 | Georgopoulos et al. | |
| 2019/0202862 A1 | 7/2019 | Verdine et al. | |

FOREIGN PATENT DOCUMENTS

| | | | |
|---|---|---|---|
| CN | 105585618 A | 5/2016 | |
| WO | WO 2018/148666 | 8/2018 | |
| WO | WO 2019/157131 | 8/2019 | |
| WO | WO-2020257260 A1 * | 12/2020 | ........... A61K 47/542 |

OTHER PUBLICATIONS

Nott. Synthesis and Characterization of LD2 Peptide Analogs to Inhibit Focal Adhesion Kinase in Cancer. Dissertation at University of Arizona, Publication Date May 2019 (Year: 2019).*

Marlowe et al. Development of a High-Throughput Fluorescence Polarization Assay to Detect Inhibitors of the FAK-Paxillin Interaction. SLAS Discov. Jan. 2020;25(1):21-32 (Year: 2020).*

Bertolucci CM, Guibao CD, Zheng J. Structural features of the focal adhesion kinase-paxillin complex give insight into the dynamics of focal adhesion assembly. Protein Sci. 2005;14(3):644-52. Epub Feb. 4, 2005. doi: 10.1110/ps.041107205. PubMed PMID: 15689512; PMCID: PMC2279287.

Cance WG, Golubovskaya VM. Focal adhesion kinase versus p53: apoptosis or survival? Sci Signal. 2008;1(20):pe22, 5 pages. PubMed PMID: 18493017.

Chang YS, et al. Stapled alpha-helical peptide drug development: a potent dual inhibitor of MDM2 and MDMX for p53-dependent cancer therapy. Proc Natl Acad Sci U S A. 2013;110(36):E3445-54. Epub Aug. 16, 2013. doi: 10.1073/pnas.1303002110. PubMed PMID: 23946421; PMCID: PMC3767549.

Deramaudt TB, Dujardin D, Noulet F, Martin S, Vauchelles R, Takeda K, Ronde P. Altering FAK-paxillin interactions reduces adhesion, migration and invasion processes. PLoS One. 2014;9(3):e92059. Epub Mar. 20, 2014. doi: 10.1371/journal.pone.0092059. PubMed PMID: 24642576; PMCID: PMC3958421.

(Continued)

*Primary Examiner* — Christina Bradley
(74) *Attorney, Agent, or Firm* — Casimir Jones, S.C.; Robert A. Goetz

(57) ABSTRACT

This disclosure provides peptides which have an affinity for the focal adhesion targeting (FAT) domain of focal adhesion kinase (FAK). In particular, the peptides are modified and derived from the sequence of the LD2 alpha helical domain of paxillin (e.g., LD2 peptides), the LD4 domain of paxillin (e.g., LD4 peptides), and CD8 peptides. These peptides are capable of blocking an interaction between paxillin and FAK, thereby inhibiting FAK activity related to FAK-paxillin interaction. The invention further provides uses for such peptides as therapeutics for the treatment of cancer and other diseases characterized with FAK activity and/or expression (e.g., fibrosis).

9 Claims, 15 Drawing Sheets

Specification includes a Sequence Listing.

(56) References Cited

OTHER PUBLICATIONS

Gao G, Prutzman KC, King ML, Scheswohl DM, DeRose EF, London RE, Schaller MD, Campbell Sl. NMR solution structure of the focal adhesion targeting domain of focal adhesion kinase in complex with a paxillin LD peptide: evidence for a two-site binding model. J Biol Chem. 2004;279(9):8441-51. PubMed PMID: 14662767.
Gao H, Wu Y, Sun Y, Yang Y, Zhou G, Rao Y. Design, Synthesis, and Evaluation of Highly Potent FAK-Targeting PROTACs. ACS Med Chem Lett. 2020, 11, 1855-1862. DOI: 10.1021/acsmedchemlett.9b00372.
Garron ML, Arthos J, Guichou JF, McNally J, Cicala C, Arold ST. Structural basis for the interaction between focal adhesion kinase and CD4. J Mol Biol. 2008;375(5):1320-8. Epub Dec. 15, 2007. doi: 10.1016/j.jmb.2007.11.040. PubMed PMID: 18078954.
Goluboyskaya VM, Finch R, Cance WG. Direct Interaction of the N-terminal domain of Focal Adhesion Kinase with the N-terminal transactivation domain of p53. J Biol Chem. 2005;280(26):25008-21. doi: 10.1074/jbc.M414172200.
Goluboyskaya VM, Kweh FA, Cance WG. Focal adhesion kinase and cancer. Histol Histopathol. 2009;24(4):503-10. Epub Feb. 19, 2009. PubMed PMID: 19224453.
Hoellerer MK, et al. Molecular recognition of paxillin LD motifs by the focal adhesion targeting domain. Structure. 2003;11(10):1207-17. Epub Oct. 7, 2003. PubMed PMID: 14527389.
Ilic D, Furuta Y, Kanazawa S, Takeda N, Sobue K, Nakatsuji N, Nomura S, Fujimoto J, Okada M, Yamamoto T. Reduced cell motility and enhanced focal adhesion contact formation in cells from FAK-deficient mice. Nature. 1995;377(6549):539-44. doi: 10.1038/377539a0. PubMed PMID: 7566154.
Infante Jr, Camidge DR, Mileshkin LR, Chen EX, Hicks RJ, Rischin D, Fingert H, Pierce KJ, Xu H, Roberts WG, Shreeve SM, Burris HA, Siu LL. Safety, pharmacokinetic, and pharmacodynamic phase I dose-escalation trial of PF-00562271, an inhibitor of focal adhesion kinase, in advanced solid tumors. J Clin Oncol. 2012;30(13):1527-33. Epub Mar. 29, 2012. doi: 10.1200/JCO.2011.38.9346. PubMed PMID: 22454420.
International Search Report & Written Opinion, International Patent Application No. PCT/US2020/048827, mailed Feb. 8, 2021, 12 pages.
Jones SF, Siu LL, Bendell JC, Cleary JM, Razak AR, Infante JR, Pandya SS, Bedard PL, Pierce KJ, Houk B, Roberts WG, Shreeve SM, Shapiro GI. A phase I study of VS-6063, a second-generation focal adhesion kinase inhibitor, in patients with advanced solid tumors. Invest New Drugs. 2015;33(5):1100-7. doi: 10.1007/s10637-015-0282-y. PubMed PMID: 26334219.
Kaneda T, Sonoda Y, Ando K, Suzuki T, Sasaki Y, Oshio T, Tago M, Kasahara T. Mutation of Y925F in focal adhesion kinase (FAK) suppresses melanoma cell proliferation and metastasis. Cancer Lett. 2008;270(2):354-61. Epub Jul. 9, 2008. doi: 10.1016/j.canlet.2008.05.042. PubMed PMID: 18606490.
Kanteti R, Batra SK, Lennon FE, Salgia R. FAK and paxillin, two potential targets in pancreatic cancer. Oncotarget. 2016;7(21):31586-601. Epub Mar. 17, 2016. doi: 10.18632/oncotarget.8040. PubMed PMID: 26980710; PMCID: PMC5058780.
Kessler BE, Sharma V, Zhou Q, Jing X, Pike LA, Kerege AA, Sams SB, Schweppe RE. FAK Expression, Not Kinase Activity, Is a Key Mediator of Thyroid Tumorigenesis and Protumorigenic Processes. Mol Cancer Res. 2016;14(9):869-82. Epub Jun. 5, 2016. doi: 10.1158/1541-7786.MCR-16-0007. PubMed PMID: 27259715; PMCID: PMC5025360.
Kurenova E, Xu L-H, Yang X, Baldwin AS, Jr., Craven RJ, Hanks SK, Liu Z-g, Cance WG. Focal Adhesion Kinase Suppresses Apoptosis by Binding to the Death Domain of Receptor-Interacting Protein. Mol Cell Biol. 2004;24(10):4361-71.
Lahlou H, Sanguin-Gendreau V, Zuo D, Cardiff RD, McLean GW, Frame MC, Muller WJ. Mammary epithelial-specific disruption of the focal adhesion kinase blocks mammary tumor progression. Proc Natl Acad Sci U S A. 2007;104(51):20302-7. PubMed PMID: 18056629.
Lark AL, Livasy CA, Calvo B, Caskey L, Moore DT, Yang X, Cance WG. Overexpression of focal adhesion kinase in primary colorectal carcinomas and colorectal liver metastases: immunohistochemistry and real-time PCR analyses. Clin Cancer Res. 2003;9(1):215-22. PubMed PMID: 12538472.
Marlowe TA, Lenzo FL, Figel SA, Grapes AT, Cance WG. Oncogenic Receptor Tyrosine Kinases Directly Phosphorylate Focal Adhesion Kinase (FAK) as a Resistance Mechanism to FAK-Kinase Inhibitors. Mol Cancer Ther. 2016;15(12):3028-39. Epub Sep. 18, 2016. doi: 10.1158/1535-7163.MCT-16-0366. PubMed PMID: 27638858; PMCID: PMC5136315.
Mclean GW, Carragher NO, Avizienyte E, Evans J, Brunton VG, Frame MC. The role of focal-adhesion kinase in cancer—a new therapeutic opportunity. Nat Rev Cancer. 2005;5(7):505-15. PubMed PMID: 16069815.
Nishimura M, Machida K, Imaizumi M, Abe T, Umeda T, Takeshima E, Watanabe T, Ohnishi Y, Takagi K, Hamaguchi M. Tyrosine phosphorylation of 100-130 kDa proteins in lung cancer correlates with poor prognosis. British Journal of Cancer. 1996;74(5):780-7.
Nocula-Lugowska et al. "Engineering synthetic antibody inhibitors specific for LD2 or LD4 motifs of paxillin" J Mol Biol, Jul. 31, 2015, vol. 427, No. 15, pp. 2532-2547.
Nott, R. "Synthesis and Characterization of LD2 Peptide Analogs to Inhibit Focal Adhesion Kinase in Cancer" Thesis, University of Arizona, May 31, 2019, Abstact only, 2 pgs.
Owens LV, Xu L, Craven RJ, Dent GA, Weiner TM, Kornberg L, Liu ET, Cance WG. Overexpression of the focal adhesion kinase (p125FAK) in invasive human tumors. Cancer Research. 1995;55(13):2752-5.
Pylayeva Y, Gillen KM, Gerald W, Beggs HE, Reichardt LF, Giancotti FG. Ras- and PI3K-dependent breast tumorigenesis in mice and humans requires focal adhesion kinase signaling. The Journal of Clinical Investigation. 2009; 119(2):252-66.
Recher C, Ysebaert L, Beyne-Rauzy O, Mansat-De Mas V, Ruidavets J-B, Cariven P, Demur C, Payrastre B, Laurent G, Racaud-Sultan C. Expression of Focal Adhesion Kinase in Acute Myeloid Leukemia Is Associated with Enhanced Blast Migration, Increased Cellularity, and Poor Prognosis. Cancer Res. 2004;64(9):3191-7. doi: 10.1158/0008-5472.can-03-3005.
Schaller MD, Borgman CA, Cobb BS, Vines RR, Reynolds AB, Parsons JT. pp125fak a structurally distinctive protein-tyrosine kinase associated with focal adhesions. Proceedings of the National Academy of Sciences of the United States of America. 1992;89(11):5192-6.
Scheswohl DM, Harrell JR, Rajfur Z, Gao G, Campbell SL, Schaller MD. Multiple paxillin binding sites regulate FAK function. J Mol Signal. 2008;3:1.11 pages Epub Jan. 4, 2008. doi: 10.1186/1750-2187-3-1. PubMed PMID: 18171471; PMCID: PMC2246129.
Sieg DJ, Hauck CR, Ilic D, Klingbeil CK, Schaefer E, Damsky CH, Schlaepfer DD. Fak integrates growth-factor and integrin signals to promote cell migration. Nat Cell Biol. 2000;2(5):249-56.
Sieg DJ, Hauck CR, Schlaepfer DD. Required role of focal adhesion kinase (FAK) for integrin-stimulated cell migration. J Cell Sci. 1999;112(Pt):2677-91.
Siesser PMF, Hanks SK. The Signaling and Biological Implications of FAK Overexpression in Cancer. Clin Cancer Res %R 101158/1078-0432CCR-06-0456. 2006;12(11):3233-7.
Sonoda Y, Matsumoto Y, Funakoshi M, Yamamoto D, Hanks SK, Kasahara T. Anti-apoptotic Role of Focal Adhesion Kinase (FAK). Induction of Inhibitor-Of-Apoptosis Proteins and Apoptosis Suppression By the Overexpression of FAK in a Human Leukemic Cell Line, HL-60. J Biol Chem. 2000;275(21):16309-15. PubMed PMID: 0010821872.
Stokes JB, et al. Inhibition of Focal Adhesion Kinase by PF-562,271 Inhibits the Growth and Metastasis of Pancreatic Cancer Concomitant with Altering the Tumor Microenvironment. Molecular Cancer Therapeutics. 2011. p. 2135-2145, doi: 10.1158/1535-7163.mct-11-0261.
Thomas JW, Cooley MA, Broome JM, Salgia R, Griffin JD, Lombardo CR, Schaller MD. The role of FAK binding in the

(56) References Cited

OTHER PUBLICATIONS regulation of tyrosine phosphorylation of paxillin. J Biol Chem. vol. 274, No. 51, Dec. 1999; pp. 36684-36692.

Verastem I. Placebo Controlled Study of VS-6063 in Subjects With Malignant Pleural Mesothelioma (Command 2015 [updated Oct. 5, 2015; cited Apr. 24, 2016, 2016]. 8 pages Available from: https://clinicaltrials.gov/ct2/show/study/NCT01870609.

Walsh C, Tanjoni I, Uryu S, Tomar A, Nam JO, Luo H, Phillips A, Patel N, Kwok C, McMahon G, Stupack DG, Schlaepfer DD. Oral delivery of PND-1186 FAK inhibitor decreases tumor growth and spontaneous breast to lung metastasis in pre-clinical models. Cancer Biol Ther. 2010;9(10):778-90. PubMed PMID: 20234193; PMCID: PMC2933309.

Weiner TM, Liu ET, Craven RJ, Cance WG. Expression of focal adhesion kinase gene and invasive cancer. Lancet. 1993;342(8878):1024-5.

Xu LH, Yang X, Craven RJ, Cance WG. The COOH-terminal domain of the focal adhesion kinase induces loss of adhesion and cell death in human tumor cells. Cell Growth Differ. 1998;9(12):999-1005.

Xu L-h, Yang X-h, Bradham CA, Brenner DA, Baldwin AS, Craven RJ, Cance WG. The focal adhesion kinase suppresses transformation-associated, anchorage-Independent apoptosis in human breast cancer cells. J Biol Chem. 2000;275:30597-604.

Xu S, Liu Y, Li X, Liu Y, Meijers R, Zhang Y, Wang JH. The binding of DCC-P3 motif and FAK-FAT domain mediates the initial step of netrin-1/DCC signaling for axon attraction. Cell Discov. 2018;4:8. Epub Feb. 27, 2018. doi: 10.1038/s41421-017-0008-8. PubMed PMID: 29479476; PMCID: PMC5818605.

Zhao X, Guan JL. Focal adhesion kinase and its signaling pathways in cell migration and angiogenesis. Advanced drug delivery reviews. 2011;63(8):610-5. Epub Dec. 2, 2010. doi: 10.1016/j.addr.2010.11.001. PubMed PMID: 21118706; PMCID: 3132829.

Mousson et al. Targeting Focal Adhesion Kinase Using Inhibitors of Protein-Protein Interactions, Cancers, vol. 10(9):278, Sep. 2018, 29 pages.

* cited by examiner

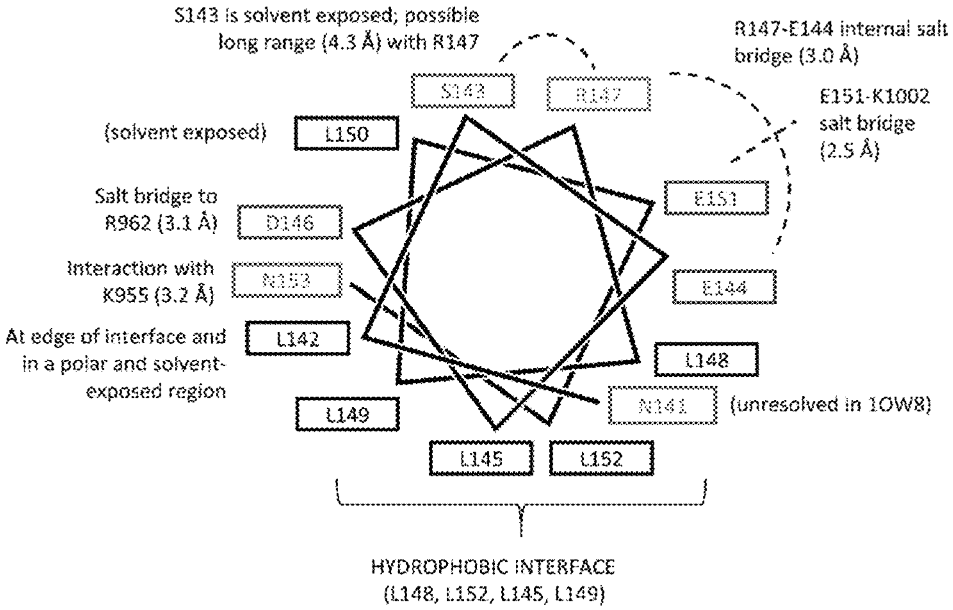

E

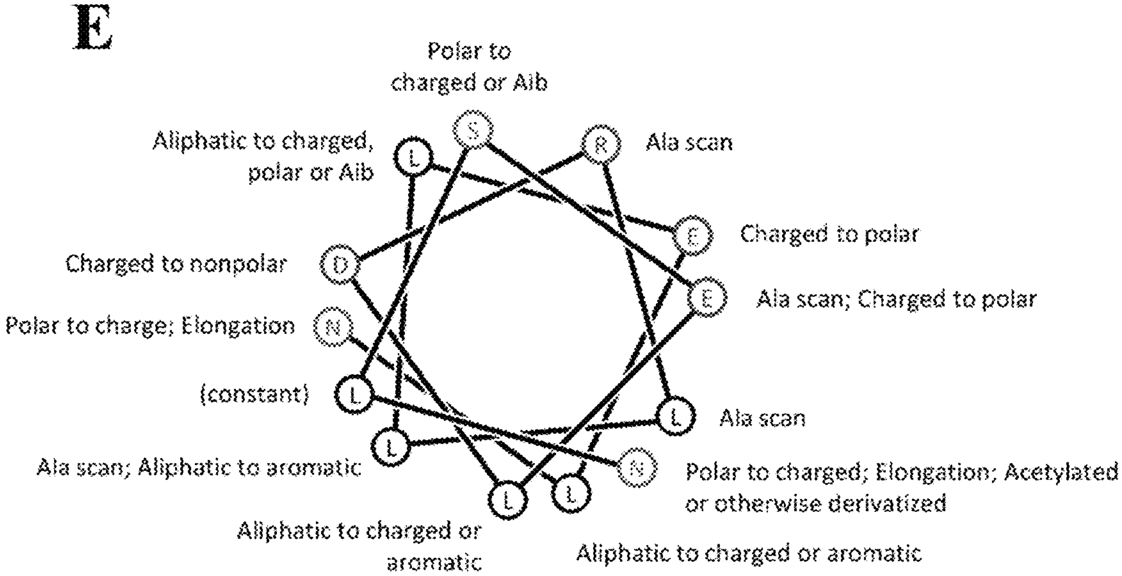

C

S143 is solvent exposed; possible long range (4.3 Å) with R147

R147-E144 internal salt bridge (3.0 Å)

E151-K1002 salt bridge (2.5 Å)

(solvent exposed)

Salt bridge to R962 (3.1 Å)

Interaction with K955 (3.2 Å)

At edge of interface and in a polar and solvent-exposed region (unresolved in 1OW8)

HYDROPHOBIC INTERFACE
(L148, L152, L145, L149)

E

Polar to charged or Aib

Aliphatic to charged, polar or Aib

Ala scan

Charged to nonpolar

Charged to polar

Polar to charge; Elongation

Ala scan; Charged to polar (constant)

Ala scan; Aliphatic to aromatic

Ala scan

Aliphatic to charged or aromatic

Polar to charged; Elongation; Acetylated or otherwise derivatized

Aliphatic to charged or aromatic

Chemical Formula: $C_{77}H_{131}N_{19}O_{22}$
Molecular Weight: 1675.01

A

B

UACC-0002019

P29

P30

P31

P32

P33 a

P34

P37

P38

SEQUENCE LISTING

```
<160> NUMBER OF SEQ ID NOS: 39

<210> SEQ ID NO 1
<211> LENGTH: 13
<212> TYPE: PRT
<213> ORGANISM: Artificial sequence
<220> FEATURE:
<223> OTHER INFORMATION: synthetic

<400> SEQUENCE: 1

Asn Leu Ser Glu Leu Asp Arg Leu Leu Leu Glu Leu Asn
1               5                   10


<210> SEQ ID NO 2
<211> LENGTH: 13
<212> TYPE: PRT
<213> ORGANISM: Artificial sequence
<220> FEATURE:
<223> OTHER INFORMATION: synthetic
```

<220> FEATURE:
<221> NAME/KEY: Xaa
<222> LOCATION: (4)..(4)
<223> OTHER INFORMATION: Xaa = (R)-2-(7-octenyl)alanine
<220> FEATURE:
<221> NAME/KEY: Xaa
<222> LOCATION: (11)..(11)
<223> OTHER INFORMATION: Xaa = (S)-2-(4-pentenyl)alanine

<400> SEQUENCE: 2

Asn Leu Ser Xaa Leu Asp Arg Leu Leu Leu Xaa Leu Asn
1 5 10

<210> SEQ ID NO 3
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (4)..(4)
<223> OTHER INFORMATION: Xaa = (R)-2-(7-octenyl)alanine
<220> FEATURE:
<221> NAME/KEY: Xaa
<222> LOCATION: (11)..(11)
<223> OTHER INFORMATION: Xaa = (S)-2-(4-pentenyl)alanine

<400> SEQUENCE: 3

Asn Leu Ser Xaa Leu Asp Arg Leu Leu Asn Xaa Leu Asn
1 5 10

<210> SEQ ID NO 4
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 4

Asn Leu Xaa Glu Leu Asp Arg Leu Leu Xaa Glu Leu Asn
1 5 10

<210> SEQ ID NO 5
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 5

Asn Leu Xaa Gln Leu Asp Arg Leu Leu Xaa Gln Leu Asn
1 5 10

<210> SEQ ID NO 6

<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = 2-aminoisobutyric acid
<220> FEATURE:
<221> NAME/KEY: Xaa
<222> LOCATION: (10)..(10)
<223> OTHER INFORMATION: Xaa = 2-aminoisobutyric acid

<400> SEQUENCE: 6

Asn Leu Xaa Glu Leu Asp Arg Leu Leu Xaa Glu Leu Asn
1               5                   10

<210> SEQ ID NO 7
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 7

Asp Leu Xaa Glu Leu Asp Arg Leu Leu Xaa Glu Leu Asp
1               5                   10

<210> SEQ ID NO 8
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (5)..(5)
<223> OTHER INFORMATION: Xaa = (R)-2-(7-octenyl)alanine
<220> FEATURE:
<221> NAME/KEY: Xaa
<222> LOCATION: (12)..(12)
<223> OTHER INFORMATION: Xaa = (S)-2-(4-pentenyl)alanine

<400> SEQUENCE: 8

Asn Leu Ser Glu Xaa Asp Arg Leu Leu Leu Glu Xaa Asn
1               5                   10

<210> SEQ ID NO 9
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (5)..(5)
<223> OTHER INFORMATION: Xaa = (S)-2-(4-pentenyl)alanine
<220> FEATURE:
<221> NAME/KEY: Xaa
<222> LOCATION: (9)..(9)
<223> OTHER INFORMATION: Xaa = (S)-2-(4-pentenyl)alanine

<400> SEQUENCE: 9

-continued

Asn Leu Ser Glu Xaa Asp Arg Leu Xaa Leu Glu Leu Asn
1 5 10

<210> SEQ ID NO 10
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (7)..(7)
<223> OTHER INFORMATION: Xaa = (R)-2-(7-octenyl)alanine
<220> FEATURE:
<221> NAME/KEY: Xaa
<222> LOCATION: (14)..(14)
<223> OTHER INFORMATION: Xaa = (S)-2-(4-pentenyl)alanine

<400> SEQUENCE: 10

Ser Leu Gly Ser Asn Leu Xaa Glu Leu Asp Arg Leu Leu Xaa Glu Leu
1 5 10 15

Asn Ala Val Gln His
20

<210> SEQ ID NO 11
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (9)..(9)
<223> OTHER INFORMATION: Xaa = (R)-2-(4-pentenyl)alanine
<220> FEATURE:
<221> NAME/KEY: Xaa
<222> LOCATION: (12)..(12)
<223> OTHER INFORMATION: Xaa = (S)-2-(4-pentenyl)alanine

<400> SEQUENCE: 11

Asn Leu Ser Glu Leu Asp Arg Leu Xaa Leu Glu Xaa Asn
1 5 10

<210> SEQ ID NO 12
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (5)..(5)
<223> OTHER INFORMATION: x = (R)-2-(7-octenyl)alanine
<220> FEATURE:
<221> NAME/KEY: Xaa
<222> LOCATION: (12)..(12)
<223> OTHER INFORMATION: x = (S)-2-(4-pentenyl)alanine

<400> SEQUENCE: 12

Asn Leu Ser Glu Xaa Asp Arg Ala Ala Leu Glu Xaa Asn
1 5 10

<210> SEQ ID NO 13
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)

```
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 13

Arg Arg Xaa Ala Arg Leu Arg Phe Met Xaa Gln Phe Tyr
1               5                   10


<210> SEQ ID NO 14
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (5)..(5)
<223> OTHER INFORMATION: Xaa = (S)-2-(4-pentenyl)alanine
<220> FEATURE:
<221> NAME/KEY: Xaa
<222> LOCATION: (9)..(9)
<223> OTHER INFORMATION: Xaa = (S)-2-(4-pentenyl)alanine

<400> SEQUENCE: 14

Asn Leu Arg Glu Xaa Asp Arg Leu Xaa Arg Glu Leu Asn
1               5                   10


<210> SEQ ID NO 15
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 15

Asn Leu Xaa Glu Trp Asp Arg Leu Leu Xaa Glu Trp Asn
1               5                   10


<210> SEQ ID NO 16
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 16

Asn Leu Xaa Glu Leu Asp Arg Leu Trp Xaa Glu Leu Asn
1               5                   10


<210> SEQ ID NO 17
<211> LENGTH: 13
<212> TYPE: PRT
<213> ORGANISM: Artificial sequence
```

<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 17

Asn Leu Xaa Ala Leu Asp Arg Leu Leu Xaa Glu Leu Asn
1               5                   10

<210> SEQ ID NO 18
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: x
<222> LOCATION: (10)..(10)
<223> OTHER INFORMATION: x = (S)-2-(4-pentenyl)alanine

<400> SEQUENCE: 18

Asn Leu Xaa Ala Leu Asp Ala Leu Leu Xaa Glu Leu Asn
1               5                   10

<210> SEQ ID NO 19
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (1)..(1)
<223> OTHER INFORMATION: Xaa = (R)-2-(7-octenyl)alanine
<220> FEATURE:
<221> NAME/KEY: Xaa
<222> LOCATION: (8)..(8)
<223> OTHER INFORMATION: Xaa = (S)-2-(4-pentenyl)alanine

<400> SEQUENCE: 19

Xaa Glu Leu Asp Arg Leu Leu Xaa
1               5

<210> SEQ ID NO 20
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 20

Asn Leu Xaa Glu Leu Asp Arg Leu Leu Xaa Glu Leu Asn
1               5                   10

<210> SEQ ID NO 21
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 21

Asn Leu Xaa Glu Glu Asp Arg Leu Leu Xaa Glu Glu Asn
1 5 10

<210> SEQ ID NO 22
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (8)..(8)
<223> OTHER INFORMATION: Xaa = (S)-2-(4-pentenyl)alanine
<220> FEATURE:
<221> NAME/KEY: Xaa
<222> LOCATION: (12)..(12)
<223> OTHER INFORMATION: Xaa = (S)-2-(4-pentenyl)alanine

<400> SEQUENCE: 22

Asn Leu Ser Glu Leu Asp Arg Xaa Leu Leu Glu Xaa Asn
1 5 10

<210> SEQ ID NO 23
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (2)..(2)
<223> OTHER INFORMATION: Xaa = (R)-2-(7-octenyl)alanine
<220> FEATURE:
<221> NAME/KEY: Xaa
<222> LOCATION: (9)..(9)
<223> OTHER INFORMATION: Xaa = (S)-2-(4-pentenyl)alanine

<400> SEQUENCE: 23

Asn Xaa Ser Glu Leu Asp Arg Leu Xaa Leu Glu Leu Asn
1 5 10

<210> SEQ ID NO 24
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (5)..(5)
<223> OTHER INFORMATION: Xaa = (R)-2-(4-pentenyl)alanine
<220> FEATURE:
<221> NAME/KEY: Xaa
<222> LOCATION: (8)..(8)
<223> OTHER INFORMATION: Xaa = (S)-2-(4-pentenyl)alanine

<400> SEQUENCE: 24

Asn Leu Ser Glu Xaa Asp Arg Xaa Leu Leu Glu Leu Asn
1 5 10

<210> SEQ ID NO 25
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (2)..(2)
<223> OTHER INFORMATION: Xaa = (R)-2-(4-pentenyl)alanine
<220> FEATURE:
<221> NAME/KEY: Xaa
<222> LOCATION: (5)..(5)
<223> OTHER INFORMATION: Xaa = (S)-2-(4-pentenyl)alanine

<400> SEQUENCE: 25

Asn Xaa Ser Glu Xaa Asp Arg Leu Leu Leu Glu Leu Asn
1 5 10

<210> SEQ ID NO 26
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 26

Asn Leu Xaa Glu Leu Asp Lys Leu Leu Xaa Glu Leu Asn
1 5 10

<210> SEQ ID NO 27
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 27

Asn Leu Xaa Glu Leu Asp Arg Leu Leu Xaa Glu Leu Asn
1 5 10

<210> SEQ ID NO 28
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: misc_feature
<222> LOCATION: (10)..(10)
<223> OTHER INFORMATION: Xaa = (S)-2-(4-pentenyl)alanine

<400> SEQUENCE: 28

Asn Leu Xaa Glu Leu Asp Arg Leu Leu Xaa Glu Leu Asn
1 5 10

<210> SEQ ID NO 29
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 29

Asn Leu Xaa Glu Glu Asp Arg Leu Leu Xaa Glu Glu Asn
1 5 10

<210> SEQ ID NO 30
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: Xaa = (R)-2-(7-octenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 30

Asn Leu Xaa Glu Leu Asp Lys Leu Leu Xaa Glu Leu Asn
1 5 10

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 15
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (4)..(4)
<223> OTHER INFORMATION: Xaa = (R)-2-(7-octenyl)alanine
<220> FEATURE:
<221> NAME/KEY: Xaa
<222> LOCATION: (11)..(11)
<223> OTHER INFORMATION: Xaa = (S)-2-(4-pentenyl)alanine

<400> SEQUENCE: 36

```
Ser Ala Thr Xaa Glu Leu Asp Glu Leu Met Xaa Ser Leu Ser Asp
1               5                   10                  15
```

<210> SEQ ID NO 37
<211> LENGTH: 15
<212> TYPE: PRT
<213> ORGANISM: Artificial sequence
<220> FEATURE:
<223> OTHER INFORMATION: synthetic
<220> FEATURE:
<221> NAME/KEY: Xaa
<222> LOCATION: (6)..(6)
<223> OTHER INFORMATION: Xaa = (S)-2-(4-pentenyl)alanine
<220> FEATURE:
<221> NAME/KEY: Xaa
<222> LOCATION: (10)..(10)
<223> OTHER INFORMATION: Xaa = (S)-2-(4-pentenyl)alanine

<400> SEQUENCE: 37

```
Ser Ala Thr Arg Glu Xaa Asp Glu Leu Xaa Ala Ser Leu Ser Asp
1               5                   10                  15
```

<210> SEQ ID NO 38

<400> SEQUENCE: 38

000

<210> SEQ ID NO 39

<400> SEQUENCE: 39

000

PEPTIDE INHIBITORS OF FOCAL ADHESION KINASE ACTIVITY AND USES THEREOF

CROSS REFERENCE TO RELATED APPLICATION

This application is a US 371 National entry of PCT/US2020/048827 filed Aug. 31, 2020, which claims priority to and the benefit of U.S. Provisional Application No. 62/894,726, filed Aug. 31, 2019, which are hereby incorporated by reference in their entireties.

STATEMENT REGARDING FEDERALLY SPONSORED RESEARCH OR DEVELOPMENT

This invention was made with government support under Grant Nos. CA065910 and CA240124 awarded by National Institutes of Health. The government has certain rights in the invention.

FIELD OF THE INVENTION

This disclosure provides peptides which have an affinity for the focal adhesion targeting (FAT) domain of focal adhesion kinase (FAK). In particular, the peptides are modified and derived from the sequence of the LD2 alpha helical domain of paxillin (e.g., LD2 peptides), the LD4 domain of paxillin (e.g., LD4 peptides), and CD8 peptides. These peptides are capable of blocking an interaction between paxillin and FAK, thereby inhibiting FAK activity related to FAK-paxillin interaction. The invention further provides uses for such peptides as therapeutics for the treatment of cancer and other diseases characterized with FAK activity and/or expression (e.g., fibrosis).

INTRODUCTION

Focal Adhesion Kinase (FAK) is a highly attractive cancer drug target due to its overexpression in 80% of solid tumors and involvement in multiple hallmarks of cancer including, for example, migration, invasion, metastasis, apoptosis, proliferation, angiogenesis, and immune-cell suppression. However, FAK inhibitors to date generally only target the kinase function and ignore FAK's role as a scaffolding protein. Importantly, FAK scaffolding interactions control many key functions of FAK such as apoptosis, proliferation, invasion, and metastasis. FAK localization to the focal adhesion is mediated by the FAK-paxillin interaction and mutation of the binding site was shown have drastic effects on FAK phosphorylation, paxillin phosphorylation, focal adhesion turnover, cell adhesion, migration, and invasion.

Improved pharmaceutical agents and related methods for treating diseases and conditions characterized with FAK activity are needed.

The present invention addresses this need through providing a new class of molecules (e.g., polypeptides, compounds) capable of effectively targeting FAK non-catalytic function through binding of the FAT domain and thereby inhibiting, for example, the FAK-paxillin interaction.

SUMMARY OF THE INVENTION

Experiments conducted during the course of developing embodiments for the present invention synthesized and optimized peptides capable of effectively targeting FAK non-catalytic function through binding of the FAT domain and thereby inhibiting, for example, FAK-paxillin interaction (e.g., FAK-LD2 domain of paxillin). In particular, the present invention provides stapled peptides capable (e.g., LD2 peptides, LD4 peptides) of inhibiting FAK-paxillin interaction. These peptides represent a significant advantage over existing FAK inhibitors due to the ability to disrupt FAK protein-protein interactions (PPIs) and therefore provide novel anti-cancer effects.

As such, the present invention provides a new class of LD2 peptides which function as inhibitors of focal adhesion kinase (FAK) activity through binding with its focal adhesion targeting (FAT) domain and thereby inhibiting FAK-paxillin interaction. The invention further provides uses for such LD2 peptides as therapeutics for the treatment of cancer, fibrotic diseases, and other diseases characterized with FAK activity.

Accordingly, the present invention contemplates that exposure of animals (e.g., humans) suffering from disorders characterized with FAK activity and/or expression (e.g., cancer (e.g., and/or cancer related disorders) (e.g., fibrosis (e.g., IPF, liver fibrosis, keloids)) to therapeutically effective amounts of peptides capable of binding with the FAT domain of a FAK protein will inhibit the growth and/or metastasis of cancer cells or supporting cells outright and/or render such cells as a population more susceptible to the cell death-inducing activity of cancer therapeutic drugs or radiation therapies. In some embodiments, the inhibition of FAK activity occurs through, for example, inhibiting FAK-paxillin binding (e.g., through binding the FAT domain of FAK).

The present invention contemplates that inhibitors of FAK activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or targeted therapy agent or tumor immunotherapy agents or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of the described peptides (e.g., LD2 peptides, LD4 peptides), of the present invention and a course of an anticancer agent produces a greater tumor response and clinical benefit in such animals compared to those treated with such a peptide or anticancer drugs/radiation alone. Since the doses for all approved anticancer drugs and radiation treatments are known, the present invention contemplates the various combinations of them with the described peptides (e.g., LD2 peptides, LD4 peptides). In some embodiments, due to synergistic effects with the described peptides of the present invention, the doses for such anticancer drugs may be lower than standard doses.

In certain embodiments of the invention, combination treatment of animals with a therapeutically effective amount of the described peptides (e.g., LD2 peptides, LD4 peptides), of the present invention and a course of any therapeutic agent for treating disorders characterized with FAK activity and/or expression (e.g., cancer (e.g., and/or cancer related disorders) (e.g., fibrosis (e.g., IPF, liver fibrosis, keloids)) results in a greater clinical benefit in such animals compared to those treated with such a peptide or therapeutic agent alone. Since the doses for all approved therapeutic agents are known, the present invention contemplates the various combinations of them with the described peptides (e.g., LD2 peptides, LD4 peptides). In some embodiments, due to synergistic effects with the described peptides of the present invention, the doses for such therapeutic agents may be lower than standard doses.

In certain embodiments, the present invention provides compounds encompassed within Formula I:

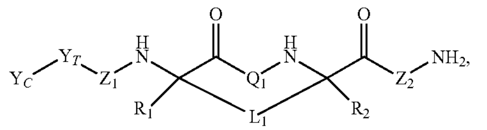

including pharmaceutically acceptable salts, solvates, and/or prodrugs thereof; wherein $Y_C$, $Y_T$, $Z_1$, $R_1$, $L_1$, $Q_1$, $R_2$, and $Z_2$ independently include any chemical moiety that permits the resulting compound to bind with the FAT domain of FAK and inhibit FAK's interaction with a paxillin protein.

In some embodiments, the compound is capable of binding with one or more of the helix1-4 and helix2-3 portions of the FAT domain of FAK. In some embodiments, the compound is capable of binding with one or more of the following amino acid residues within a wild type FAK protein: V928, I936, R962, and K955. However, the compound is capable of also binding additional amino acid residues of a FAK protein. In some embodiments, the compound is capable of inhibiting interaction between FAK and paxillin.

In some embodiments, the compound is an isolated polypeptide.

In some embodiments, wherein the compound is capable of one or more of the following:

- disrupting FAK non-catalytic activity upon inhibition of interaction between FAK and paxillin,
- disrupting FAK catalytic activity through direct binding of the FAT domain,
- inhibiting FAK related scaffolding function,
- inhibiting FAK protein-protein interactions mediated by the FAT domain,
- inhibiting binding of paxillin with the helix 1-4 region of the FAT domain of FAK,
- inhibiting binding of paxillin with the helix 2-3 region of the FAT domain of FAK,
- inhibiting FAK related apoptosis, proliferation, invasion, and/or metastasis,
- inhibiting FAK-paxillin interaction resulting inhibiting of FAK phosphorylation, paxillin phosphorylation, focal adhesion turnover, cell adhesion, migration, and/or invasion,
- inhibiting FAK-Leupaxin interaction through binding the FAT domain of FAK,
- inhibiting FAK-CD4 interaction through binding the FAT domain of FAK,
- inhibiting FAK-CD8 interaction through binding the FAT domain of FAK,
- inhibiting FAK-DCC interaction through binding the FAT domain of FAK,
- inhibiting paxillin LD2 and LD4 binding with respective binding partners,
- inhibiting CD4 and CD8 binding with respective binding partners,
- inhibiting CD4 and CD8 binding with Lck,
- inhibiting Leupaxin binding with respective binding partners,
- inhibiting DCC binding with respective binding partners,
- inhibiting interactions of FAK-related molecules including Pyk2, Vinculin, ILK, Actopaxin, PKL, Git1/2, Pax3, hic-5, and ARF.

In some embodiments, $Q_1$ is a chain of 2 (-[Aa1]-[Aa2]-), 3 (-[Aa1]-[Aa2]-[Aa3]-), 6 (-[Aa1]-[Aa2]-[Aa3]-[Aa4]-[Aa5]-[Aa6]-) or 10 (-[Aa1]-[Aa2]-[Aa3]-[Aa4]-[Aa5]-[Aa6]-[Aa7]-[Aa8]-[Aa9]-[Aa10]-) amino acids resulting in motifs, respectively, of (i, i+3); (i, i+4); (i, i+7) and (i, i+11); wherein "i" refers to the alpha-amino acid backbone residue towards the N-terminus of the macrocycle and the "number" in "i+[number]" refers to the amino acid residue [number] away from i towards the C-terminus; wherein Aa1, Aa2, Aa3, Aa4, Aa5, Aa6, Aa7, Aa8, Aa9, Aa10 are independent of each other and are each a natural or unnatural alpha-amino acid.

In some embodiments, $Z_1$ and $Z_2$ are independent of each other and are each a chain of natural or unnatural amino acids between 0 and 200 units in length.

In some embodiments, $Y_C$ is an optional moiety such as an affinity tag (e.g. biotin), a molecular probe or a dye (fluorescent or otherwise), or a chemically reactive moiety including but not limited to an azide, alkyne, or photoreactive species. Examples can be found in, but are not limited to the selection in, the Molecular Probes Handbook, Eleventh edition, lain D. Johnson, Life Technologies Corporation, 2010 (ISBN 978-0-9829279-0-8), or a FAK kinase inhibiting agent.

In some embodiments, $Y_C$ is a covalent derivative of an inhibitor of FAK kinase catalytic activity. In some embodiments, $Y_C$ is a covalent derivative of other kinase inhibitors (e.g. Src, EGFR, HER2, etc.). In some embodiments, $Y_C$ is a covalent derivative of a GPCR compound. In some embodiments, $Y_C$ is a covalent derivative of a nuclear receptor compound. In some embodiments, $Y_C$ is a covalent derivative of an E3 ubiquitin ligase targeting ligand. In some embodiments, $Y_C$ is a covalent derivative of a protein-protein interaction inhibitor. In some embodiments, $Y_C$ is a covalent derivative of a radioactive moiety. In some embodiments, $Y_C$ is a covalent derivative of a drug transporter-binding ligand. In some embodiments, $Y_C$ is a covalent derivative of a cell penetrating moiety/sequence (e.g. TAT, etc.). In some embodiments, $Y_C$ is a covalent derivative of a chemotherapeutic agent. In some embodiments, $Y_C$ is a covalent derivative of a lipid moiety. In some embodiments, $Y_C$ is a covalent derivative of a pro-drug moiety facilitating favorable bioavailability and/or pharmacokinetics. In some embodiments, $Y_C$ is a covalent derivative of an electrophilic moiety for covalent binding to the target protein.

In some embodiments, $Y_T$ is an optional chemical tether between $Y_C$ and $Z_1$. In some embodiments, $Y_T$ forms an alkyl or amide (e.g., carbamide, sulfonamide or phosphoramide) group if present. In some embodiments, $Y_T$ may or may not contain one or more carbon atoms, or one or more sulfur atoms, or one or more oxygen atoms, or one or more nitrogen atoms, or one or more carbo- or heterocyclic rings. In some embodiments, the chemical tether is selected from beta-alanine, 6-aminohexanoic acid and an amino acid where the amine and acid functionalities are separated by a poly(ethyleneglycol) (PEG) monomer, oligomer or polymer.

In some embodiments, $R_1$ is a hydrogen or lower alkyl or substituted methyl group.

In some embodiments, $R_2$ is a hydrogen or lower alkyl or substituted methyl group.

In some embodiments, $L_1$ is typically a hydrocarbon chain containing a single double bond, of cis- or trans-geometry, or a mixture thereof, typically containing 8 or 11 atoms, but may be a different integer.

In some embodiments, $L_1$ is any combination of atoms and molecules that would allow for the amino acid containing $R_1$ in Formula I to be covalently attached to the amino acid containing $R_2$ in Formula I, exclusive of the inherent peptide backbone. In some embodiments, $L_1$ is a hydrocarbon chain containing 8 atoms and a single double bond of cis- or trans-configuration, or a mixture thereof. In some embodiments, $L_1$ is a hydrocarbon chain containing 11 atoms and a single double bond, of cis- or trans-configuration, or a mixture thereof. In some embodiments, $L_1$ is a hydrocarbon chain containing neither 8 nor 11 atoms, and a single double bond of cis- or trans-configuration, or a mixture thereof. In some embodiments, $L_1$ contains two sulfur atoms that are covalently attached in a manner other than a disulfide bond. In some embodiments, $L_1$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group. $L_1$ may or may not contain one or more sulfur atoms, or one or more oxygen atoms, or one or more nitrogen atoms. This list is not meant to be exhaustive and one skilled in the art can readily imagine other covalent linking strategies.

In some embodiments, the compound is at least 60% identical with one of SEQ ID Nos: 1-30, 36, and 37. In some embodiments, the compound is at least 75% identical with one of SEQ ID Nos: 1-30, 36, and 37. In some embodiments, the compound is at least 80% identical with one of SEQ ID Nos: 1-30, 36, and 37. In some embodiments, the compound is at least 85% identical with one of SEQ ID Nos: 1-30, 36, and 37. In some embodiments, the compound is at least 90% identical with one of SEQ ID Nos: 1-30, 36, and 37. In some embodiments, the compound is at least 95% identical with one of SEQ ID Nos: 1-30, 36, and 37. In some embodiments, the compound is at least 98% identical with one of SEQ ID Nos: 1-30, 36, and 37. In some embodiments, the compound is at least 99% identical with one of SEQ ID Nos: 1-30, 36, and 37. In some embodiments, the compound comprises, consists of, or consists essentially of one of SEQ ID Nos: 1-30, 36, and 37.

In certain embodiments, the present invention provides compounds encompassed within Formula II:

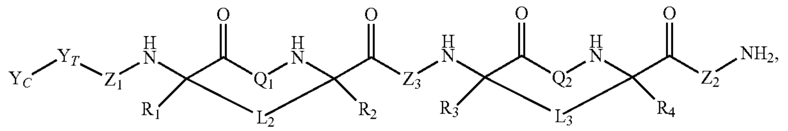

including pharmaceutically acceptable salts, solvates, and/or prodrugs thereof; wherein $Y_C$, $Y_T$, $Z_1$, $R_1$, $Q_1$, $L_2$, $R_2$, $Z_3$, $R_3$, $Q_2$, $L_3$, $R_4$ and $Z_2$ include any chemical moiety that permits the resulting compound to bind with the FAT domain of FAK and inhibit FAK's interaction with a paxillin protein.

In some embodiments, the compound is capable of binding with one or more of the helix1-4 and helix2-3 portions of the FAT domain of FAK. In some embodiments, the compound is capable of binding with one or more of the following amino acid residues within a wild type FAK protein: V928, I936, R962, and K955. However, the compound is capable of also binding additional amino acid residues of a FAK protein. In some embodiments, the compound is capable of inhibiting interaction between FAK and paxillin. In some embodiments, the compound is an isolated polypeptide.

In some embodiments, wherein the compound is capable of one or more of the following:

- disrupting FAK non-catalytic activity upon inhibition of interaction between FAK and paxillin,
- disrupting FAK catalytic activity through direct binding of the FAT domain,
- inhibiting FAK related scaffolding function,
- inhibiting FAK protein-protein interactions mediated by the FAT domain,
- inhibiting binding of paxillin with the helix 1-4 region of the FAT domain of FAK,
- inhibiting binding of paxillin with the helix 2-3 region of the FAT domain of FAK,
- inhibiting FAK related apoptosis, proliferation, invasion, and/or metastasis,
- inhibiting FAK-paxillin interaction resulting inhibiting of FAK phosphorylation, paxillin phosphorylation, focal adhesion turnover, cell adhesion, migration, and/or invasion,
- inhibiting FAK-Leupaxin interaction through binding the FAT domain of FAK,
- inhibiting FAK-CD4 interaction through binding the FAT domain of FAK,
- inhibiting FAK-CD8 interaction through binding the FAT domain of FAK,
- inhibiting FAK-DCC interaction through binding the FAT domain of FAK,
- inhibiting paxillin LD2 and LD4 binding with respective binding partners,
- inhibiting CD4 and CD8 binding with respective binding partners,
- inhibiting CD4 and CD8 binding with Lck,
- inhibiting Leupaxin binding with respective binding partners,
- inhibiting DCC binding with respective binding partners,
- inhibiting interactions of FAK-related molecules including Pyk2, Vinculin, ILK, Actopaxin, PKL, Git1/2, Pax3, hic-5, and ARF.

In some embodiments, $Q_1$ is a chain of 2 (-[Aa1]-[Aa2]-), 3 (-[Aa1]-[Aa2]-[Aa3]-), 6 (-[Aa1]-[Aa2]-[Aa3]-[Aa4]-[Aa5]-[Aa6]-) or 10 (-[Aa11]-[Aa2]-[Aa3]-[Aa4]-[Aa5]-[Aa6]-

[Aa7]-[Aa8]-[Aa9]-[Aa10]-) amino acids resulting in motifs, respectively, of (i, i+3); (i, i+4); (i, i+7) and (i, i+11);

$Q_2$ is a chain of 2 (-[Aa11]-[Aa12]-), 3 (-[Aa11]-[Aa12]-[Aa13]-), 6 (-[Aa11]-[Aa12]-[Aa13]-[Aa14]-[Aa15]-[Aa16]-) or 10 (-[Aa11]-[Aa12]-[Aa13]-[Aa14]-[Aa15]-[Aa16]-[Aa17]-[Aa18]-[Aa19]-[Aa20]-) amino acids resulting in motifs, respectively, of (i, i+3); (i, i+4); (i, i+7) and (i, i+11);

"i" refers to the alpha-amino acid backbone residue towards the N-terminus of the macrocycle and the "number" in "i+[number]" refers to the amino acid residue [number] away from i towards the C-terminus;

Aa1, Aa2, Aa3, Aa4, Aa5, Aa6, Aa7, Aa8, Aa9, Aa10 are independent of each other and are each a natural or unnatural alpha-amino acid; and Aa11, Aa12, Aa13, Aa14, Aa15, Aa16, Aa17, Aa18, Aa19, Aa20 are independent of each other and are each a natural or unnatural alpha-amino acid.

In some embodiments, $Z_1$ and $Z_2$ and $Z_3$ are independent of each other and are each a chain of natural or unnatural amino acids between 0 and 200 units in length.

In some embodiments, $Y_C$ is an optional moiety such as an affinity tag (e.g. biotin), a molecular probe or a dye (fluorescent or otherwise), or a chemically reactive moiety including but not limited to an azide, alkyne, or photoreactive species. Examples can be found in, but are not limited to the selection in, the Molecular Probes Handbook, Eleventh edition, Iain D. Johnson, Life Technologies Corporation, 2010 (ISBN 978-0-9829279-0-8), or a FAK kinase inhibiting agent.

In some embodiments, $Y_C$ is a covalent derivative of an inhibitor of FAK kinase catalytic activity. In some embodiments, $Y_C$ is a covalent derivative of other kinase inhibitors (e.g., EGFR, HER2, etc.). In some embodiments, $Y_C$ is a covalent derivative of a GPCR compound. In some embodiments, $Y_C$ is a covalent derivative of a nuclear receptor compound. In some embodiments, $Y_C$ is a covalent derivative of an E3 ubiquitin ligase targeting ligand. In some embodiments, $Y_C$ is a covalent derivative of a protein-protein interaction inhibitor. In some embodiments, $Y_C$ is a covalent derivative of a radioactive moiety. In some embodiments, $Y_C$ is a covalent derivative of a drug transporter-binding ligand. In some embodiments, $Y_C$ is a covalent derivative of a cell penetrating moiety/sequence (e.g. TAT, etc.). In some embodiments, $Y_C$ is a covalent derivative of a chemotherapeutic agent. In some embodiments, $Y_C$ is a covalent derivative of a lipid moiety. In some embodiments, $Y_C$ is a covalent derivative of a pro-drug moiety facilitating favorable bioavailability and/or pharmacokinetics. In some embodiments, $Y_C$ is a covalent derivative of an electrophilic moiety for covalent binding to the target protein.

In some embodiments, $Y_T$ is an optional chemical tether between $Y_C$ and $Z_1$. In some embodiments, $Y_T$ forms an alkyl or amide (e.g., carbamide, sulfonamide or phosphoramide) group if present. In some embodiments, $Y_T$ may or may not contain one or more carbon atoms, or one or more sulfur atoms, or one or more oxygen atoms, or one or more nitrogen atoms, or one or more carbo- or heterocyclic rings. In some embodiments, the chemical tether is selected from beta-alanine, 6-aminohexanoic acid and an amino acid where the amine and acid functionalities are separated by a poly(ethyleneglycol) (PEG) monomer, oligomer or polymer.

In some embodiments, $R_1$ and $R_2$ are independently a hydrogen or lower alkyl or substituted methyl group.

In some embodiments, $R_3$ and $R_4$ are independently a hydrogen or lower alkyl or substituted methyl group.

In some embodiments, $L_2$ is typically a hydrocarbon chain containing a single double bond, of cis- or trans-geometry, or a mixture thereof, typically containing 8 or 11 atoms, but may be a different integer.

In some embodiments, $L_2$ is any combination of atoms and molecules that would allow for the amino acid containing $R_1$ in Formula II to be covalently attached to the amino acid containing $R_2$ in Formula II, exclusive of the inherent peptide backbone. In one embodiment, $L_2$ is a hydrocarbon chain containing 8 atoms and a single double bond of cis- or trans-configuration, or a mixture thereof. In another embodiment, $L_2$ is a hydrocarbon chain containing 11 atoms and a single double bond, of cis- or trans-configuration, or a mixture thereof. In another embodiment, $L_2$ is a hydrocarbon chain containing neither 8 nor 11 atoms, and a single double bond of cis- or trans-configuration, or a mixture thereof. In another embodiment, $L_2$ contains two sulfur atoms that are covalently attached in a manner other than a disulfide bond. In another embodiment, $L_2$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group. $L_1$ may or may not contain one or more sulfur atoms, or one or more oxygen atoms, or one or more nitrogen atoms. This list is not meant to be exhaustive and one skilled in the art can readily imagine other covalent linking strategies.

In some embodiments, $L_3$ is typically a hydrocarbon chain containing a single double bond, of cis- or trans-geometry, or a mixture thereof, typically containing 8 or 11 atoms, but may be a different integer.

In some embodiments, $L_3$ is any combination of atoms and molecules that would allow for the amino acid containing $R_1$ in Formula II to be covalently attached to the amino acid containing $R_2$ in Formula II, exclusive of the inherent peptide backbone. In one embodiment, $L_3$ is a hydrocarbon chain containing 8 atoms and a single double bond of cis- or trans-configuration, or a mixture thereof. In another embodiment, $L_3$ is a hydrocarbon chain containing 11 atoms and a single double bond, of cis- or trans-configuration, or a mixture thereof. In another embodiment, $L_3$ is a hydrocarbon chain containing neither 8 nor 11 atoms, and a single double bond of cis- or trans-configuration, or a mixture thereof. In another embodiment, $L_3$ contains two sulfur atoms that are covalently attached in a manner other than a disulfide bond. In another embodiment, $L_3$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group. $L_1$ may or may not contain one or more sulfur atoms, or one or more oxygen atoms, or one or more nitrogen atoms. This list is not meant to be exhaustive and one skilled in the art can readily imagine other covalent linking strategies.

In some embodiments, at least a portion of the compound encompasses an amino acid sequence that is at least 60% identical with one of SEQ ID Nos: 1-30, 36, and 37. In some embodiments, at least a portion of the compound encompasses an amino acid sequence that is at least 75% identical with one of SEQ ID Nos: 1-30, 36, and 37. In some embodiments, at least a portion of the compound encompasses an amino acid sequence that is at least 80% identical with one of SEQ ID Nos: 1-30, 36, and 37. In some embodiments, at least a portion of the compound encompasses an amino acid sequence that is at least 85% identical with one of SEQ ID Nos: 1-30, 36, and 37. In some embodiments, at least a portion of the compound encompasses an amino acid sequence that is at least 90% identical with one of SEQ ID Nos: 1-30, 36, and 37. In some embodiments, at least a portion of the compound encompasses an amino acid sequence that is at least 95% identical with one of SEQ ID Nos: 1-30, 36, and 37. In some embodiments, at least a portion of the compound encompasses an amino acid sequence that is at least 98% identical with one of SEQ ID Nos: 1-30, 36, and 37. In some embodiments, at least a portion of the compound encompasses an amino acid sequence that is at least 99% identical with one of SEQ ID Nos: 1-30, 36, and 37. In some embodiments, at least a portion of the compound comprises one of SEQ ID Nos: 1-30, 36, and 37.

In certain embodiments, the present invention encompassed within Formula III:

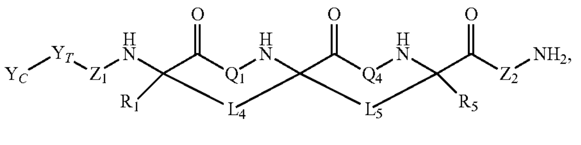

including pharmaceutically acceptable salts, solvates, and/or prodrugs thereof; wherein $Y_C$, $Y_T$, $Z_1$, $R_1$, $Q_1$, $L_4$, $Q_4$, $L_5$, $R_5$, and $Z_2$ independently include any chemical moiety that permits the resulting compound to bind with the FAT domain of FAK and inhibit FAK's interaction with a paxillin protein.

In some embodiments, the compound is capable of binding with one or more of the helix1-4 and helix2-3 portions of the FAT domain of FAK. In some embodiments, the compound is capable of binding with one or more of the following amino acid residues within a wild type FAK protein: V928, I936, R962, and K955. However, the compound is capable of also binding additional amino acid residues of a FAK protein. In some embodiments, the compound is capable of inhibiting interaction between FAK and paxillin.

In some embodiments, the compound is an isolated polypeptide.

In some embodiments, wherein the compound is capable of one or more of the following:

disrupting FAK non-catalytic activity upon inhibition of interaction between FAK and paxillin, disrupting FAK catalytic activity through direct binding of the FAT domain, inhibiting FAK related scaffolding function, inhibiting FAK protein-protein interactions mediated by the FAT domain, inhibiting binding of paxillin with the helix 1-4 region of the FAT domain of FAK, inhibiting binding of paxillin with the helix 2-3 region of the FAT domain of FAK, inhibiting FAK related apoptosis, proliferation, invasion, and/or metastasis, inhibiting FAK-paxillin interaction resulting inhibiting of FAK phosphorylation, paxillin phosphorylation, focal adhesion turnover, cell adhesion, migration, and/or invasion, inhibiting FAK-Leupaxin interaction through binding the FAT domain of FAK, inhibiting FAK-CD4 interaction through binding the FAT domain of FAK, inhibiting FAK-CD8 interaction through binding the FAT domain of FAK, inhibiting FAK-DCC interaction through binding the FAT domain of FAK, inhibiting paxillin LD2 and LD4 binding with respective binding partners, inhibiting CD4 and CD8 binding with respective binding partners, inhibiting CD4 and CD8 binding with Lck, inhibiting Leupaxin binding with respective binding partners, inhibiting DCC binding with respective binding partners, inhibiting interactions of FAK-related molecules including Pyk2, Vinculin, ILK, Actopaxin, PKL, Git1/2, Pax3, hic-5, and ARF.

In some embodiments, $Q_1$ is a chain of 2 (-[Aa1]-[Aa2]-), 3 (-[Aa1]-[Aa2]-[Aa3]-), 6 (-[Aa1]-[Aa2]-[Aa3]-[Aa4]-[Aa5]-[Aa6]-) or 10 (-[Aa1]-[Aa2]-[Aa3]-[Aa4]-[Aa5]-[Aa6]-[Aa7]-[Aa8]-[Aa9]-[Aa10]-) amino acids resulting in motifs, respectively, of (i, i+3); (i, i+4); (i, i+7) and (i, i+11);

$Q_4$ is a chain of 2 (-[Aa11]-[Aa12]-), 3 (-[Aa11]-[Aa12]-[Aa13]-), 6 (-[Aa11]-[Aa12]-[Aa13]-[Aa14]-[Aa15]-[Aa16]-) or 10 (-[Aa11]-[Aa12]-[Aa13]-[Aa14]-[Aa15]-[Aa16]-[Aa17]-[Aa18]-[Aa19]-[Aa20]-) amino acids resulting in motifs, respectively, of (i, i+3); (i, i+4); (i, i+7) and (i, i+11);

"i" refers to the alpha-amino acid backbone residue towards the N-terminus of the macrocycle and the "number" in "i+[number]" refers to the amino acid residue [number] away from i towards the C-terminus;

Aa1, Aa2, Aa3, Aa4, Aa5, Aa6, Aa7, Aa8, Aa9, Aa10 are independent of each other and are each a natural or unnatural alpha-amino acid; and Aa11, Aa12, Aa13, Aa14, Aa15, Aa16, Aa17, Aa18, Aa19, Aa20 are independent of each other and are each a natural or unnatural alpha-amino acid.

In some embodiments, $Z_1$ and $Z_2$ are independent of each other and are each a chain of natural or unnatural amino acids between 0 and 200 units in length.

In some embodiments, $Y_C$ is an optional moiety such as an affinity tag (e.g. biotin), a molecular probe or a dye (fluorescent or otherwise), or a chemically reactive moiety including but not limited to an azide, alkyne, or photoreactive species. Examples can be found in, but are not limited to the selection in, the Molecular Probes Handbook, Eleventh edition, lain D. Johnson, Life Technologies Corporation, 2010 (ISBN 978-0-9829279-0-8), or a FAK kinase inhibiting agent.

In some embodiments, $Y_T$ is an optional chemical tether between $Y_C$ and $Z_1$. In some embodiments, $Y_T$ forms an alkyl or amide (e.g., carbamide, sulfonamide or phosphoramide) group if present. In some embodiments, $Y_T$ may or may not contain one or more carbon atoms, or one or more sulfur atoms, or one or more oxygen atoms, or one or more nitrogen atoms, or one or more carbo- or heterocyclic rings. In some embodiments, the chemical tether is selected from beta-alanine, 6-aminohexanoic acid and an amino acid where the amine and acid functionalities are separated by a poly(ethyleneglycol) (PEG) monomer, oligomer or polymer.

In some embodiments, $Y_C$ is a covalent derivative of an inhibitor of FAK kinase catalytic activity. In some embodiments, $Y_C$ is a covalent derivative of other kinase inhibitors (e.g., EGFR, HER2, etc.). In some embodiments, $Y_C$ is a covalent derivative of a GPCR compound. In some embodiments, $Y_C$ is a covalent derivative of a nuclear receptor compound. In some embodiments, $Y_C$ is a covalent derivative of an E3 ubiquitin ligase targeting ligand. In some embodiments, $Y_C$ is a covalent derivative of a protein-protein interaction inhibitor. In some embodiments, $Y_C$ is a covalent derivative of a radioactive moiety. In some embodiments, $Y_C$ is a covalent derivative of a drug transporter-binding ligand. In some embodiments, $Y_C$ is a covalent derivative of a cell penetrating moiety/sequence (e.g. TAT, etc.). In some embodiments, $Y_C$ is a covalent derivative of a chemotherapeutic agent. In some embodiments, $Y_C$ is a covalent derivative of a lipid moiety. In some embodiments, $Y_C$ is a covalent derivative of a pro-drug moiety facilitating favorable bioavailability and/or pharmacokinetics. In some embodiments, $Y_C$ is a covalent derivative of an electrophilic moiety for covalent binding to the target protein.

In some embodiments, $R_1$ and $R_5$ are independently selected from a hydrogen or lower alkyl or substituted methyl group.

In some embodiments, $L_4$ and L5 are independently selected from a hydrocarbon chain containing a single double bond, of cis- or trans-geometry, or a mixture thereof, typically containing 8 or 11 atoms, but may be a different integer.

In some embodiments, $L_4$ is any combination of atoms and molecules that would allow for the amino acid containing $R_1$ in Formula III to be covalently attached to the amino acid containing $R_2$ in Formula III, exclusive of the inherent peptide backbone. In one embodiment, $L_4$ is a hydrocarbon chain containing 8 atoms and a single double bond of cis- or trans-configuration, or a mixture thereof. In another embodiment, $L_4$ is a hydrocarbon chain containing 11 atoms and a single double bond, of cis- or trans-configuration, or a mixture thereof. In another embodiment, $L_4$ is a hydrocarbon chain containing neither 8 nor 11 atoms, and a single double bond of cis- or trans-configuration, or a mixture thereof. In another embodiment, $L_4$ contains two sulfur atoms that are covalently attached in a manner other than a disulfide bond. In another embodiment, $L_4$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group. $L_1$ may or may not contain one or more sulfur atoms, or one or more oxygen atoms, or one or more nitrogen atoms. This list is not meant to be exhaustive and one skilled in the art can readily imagine other covalent linking strategies.

In some embodiments, $L_5$ is any combination of atoms and molecules that would allow for the amino acid containing $R_1$ in Formula III to be covalently attached to the amino acid containing $R_2$ in Formula III, exclusive of the inherent peptide backbone. In one embodiment, $L_5$ is a hydrocarbon chain containing 8 atoms and a single double bond of cis- or trans-configuration, or a mixture thereof. In another embodiment, $L_5$ is a hydrocarbon chain containing 11 atoms and a single double bond, of cis- or trans-configuration, or a mixture thereof. In another embodiment, $L_5$ is a hydrocarbon chain containing neither 8 nor 11 atoms, and a single double bond of cis- or trans-configuration, or a mixture thereof. In another embodiment, $L_5$ contains two sulfur atoms that are covalently attached in a manner other than a disulfide bond. In another embodiment, $L_5$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group. $L_1$ may or may not contain one or more carbon atoms, or one or more sulfur atoms, or one or more oxygen atoms, or one or more nitrogen atoms. This list is not meant to be exhaustive and one skilled in the art can readily imagine other covalent linking strategies.

In some embodiments, at least a portion of the compound encompasses an amino acid sequence that is at least 60% identical with one of SEQ ID Nos: 1-30, 36, and 37. In some embodiments, at least a portion of the compound encompasses an amino acid sequence that is at least 75% identical with one of SEQ ID Nos: 1-30, 36, and 37. In some embodiments, at least a portion of the compound encompasses an amino acid sequence that is at least 80% identical with one of SEQ ID Nos: 1-30, 36, and 37. In some embodiments, at least a portion of the compound encompasses an amino acid sequence that is at least 85% identical with one of SEQ ID Nos: 1-30, 36, and 37. In some embodiments, at least a portion of the compound encompasses an amino acid sequence that is at least 90% identical with one of SEQ ID Nos: 1-30, 36, and 37. In some embodiments, at least a portion of the compound encompasses an amino acid sequence that is at least 95% identical with one of SEQ ID Nos: 1-30, 36, and 37. In some embodiments, at least a portion of the compound encompasses an amino acid sequence that is at least 98% identical with one of SEQ ID Nos: 1-30, 36, and 37. In some embodiments, at least a portion of the compound encompasses an amino acid sequence that is at least 99% identical with one of SEQ ID Nos: 1-30, 36, and 37. In some embodiments, at least a portion of the compound comprises one of SEQ ID Nos: 1-30, 36, and 37.

In certain embodiments, the present invention provides a compound encompassed within Formula IV:

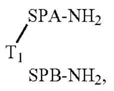

including pharmaceutically acceptable salts, solvates, and/or prodrugs thereof; wherein SPA-NH2 and SPB-NH2 are independently a compound of Formula I excluding $Y_C$-$Y_T$-, or a compound of Formula II excluding $Y_C$-$Y_T$-, or a compound of Formula III excluding $Y_C$-$Y_T$-; wherein $T_j$ is a tether or 0-400 atoms in length, which typically, but not necessarily, might include a poly(ethyleneglycol) chain and which is typically, but not necessarily, connected to SPA-NH2 and SPB-NH2 as an amide functionality and which may or may not contain an internal structure such as a carbocycle or heterocycle which may or may not function as a dye or chromophore, and may or may not branch to a pendant moiety such as biotin or a dye or chemical probe or reactive group or reactive E3 ligase ligand. In some embodiments, the tether ($T_1$) is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group or E3 ligase ligand. In some embodiments, $T_1$ may or may not contain one or more carbon atoms, or one or more sulfur atoms, or one or more oxygen atoms, or one or more nitrogen atoms.

In some embodiments, $T_1$ is the product of a "click chemistry" reaction. As a non-limiting example, SPA-NH2 might have an N-terminal alkyne and SPB-NH2 might have an N-terminal azido functionality. The product of these two species is a substituted 1H-1,2,3-triazole. In some instances a catalyst is used in the reaction.

In certain embodiments, the present invention provides compounds encompassed within Formula V:

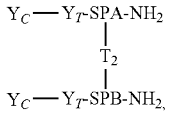

including pharmaceutically acceptable salts, solvates, and/or prodrugs thereof; wherein $Y_C$-$Y_T$-SPA-$NH_2$ and $Y_C$-$Y_T$-SPB-$NH_2$ are independently a compound of Formula I, or a compound of Formula II, or a compound of Formula III, wherein the side chain from an individual member of [Aa1], [Aa2], [Aa3], [Aa4], [Aa5], [Aa6], [Aa7], [Aa8], [Aa9], [Aa10], [Aa11], [Aa12], [Aa13], [Aa14], [Aa15], [Aa16], [Aa17], [Aa18], [Aa19] or [Aa20]; or from an amino acid that is part of $Z_1$; or from an amino acid that is part of $Z_2$; or from an amino acid that is part of $Z_3$, as found on $Y_C$-$Y_T$-SPA-$NH_2$, is connected via a tether ($T_2$) to the side chain from an individual member of [Aa1], [Aa2], [Aa3], [Aa4], [Aa5], [Aa6], [Aa7], [Aa8], [Aa9], [Aa10], [Aa11], [Aa12], [Aa13], [Aa14], [Aa15], [Aa16], [Aa17], [Aa18], [Aa19] or [Aa20]; or from an amino acid that is part of $Z_1$; or from an amino acid that is part of $Z_2$; or from an amino acid that is part of $Z_3$, as found on $Y_C$-$Y_T$-SPB-$NH_2$ via chemical ligation.

In some embodiments, the tether ($T_2$) is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group or E3 ligase ligand. In some embodiments, $T_2$ may or may not contain one or more carbon atoms, or one or more sulfur atoms, or one or more oxygen atoms, or one or more nitrogen atoms.

In some embodiments, $T_2$ is the product of a "click chemistry" reaction. As a non-limiting example, SPA-$NH_2$ might have an N-terminal alkyne and SPB-$NH_2$ might have an N-terminal azido functionality. The product of these two species is a substituted 1H-1,2,3-triazole. In some instances a catalyst is used in the reaction.

In certain embodiments, the present invention provides compounds encompassed within Formula VI:

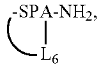

including pharmaceutically acceptable salts, solvates, and/or prodrugs thereof; wherein SPA-$NH_2$ is a compound of Formula I (as recited in claim 1) excluding $Y_C$-$Y_T$-, or a compound of Formula II excluding $Y_C$-$Y_T$—, or a compound of Formula III excluding $Y_C$-$Y_T$—, wherein the N-terminus of SPA-$NH_2$ is connected via linker $L_6$ to an internal amino acid (individually a member of [Aa1], [Aa2], [Aa3], [Aa4], [Aa5], [Aa6], [Aa7], [Aa8], [Aa9], [Aa10], [Aa1 1], [Aa12], [Aa13], [Aa14], [Aa15], [Aa16], [Aa17], [Aa18], [Aa19] or [Aa20]; or from an amino acid that is part of $Z_1$; or from an amino acid that is part of $Z_2$; or from an amino acid that is part of $Z_3$) from SPA-$NH_2$, wherein the linker might be a hydrocarbon chain containing a cis- or trans-alkene, or a mixture thereof; or it might be an ether (including a polyether such as poly(ethyleneglycol)), ester, amide, thioether, thioester or a hydrocarbon chain, which may or may not contain internal unsaturation (such as a single or multiple double bonds, or one or more alkynes).

In some embodiments, $L_6$ is any combination of atoms and molecules that would allow for the covalent attachment of the N-terminus of SPA-$NH_2$ with any other amino acid that comprises SPA-$NH_2$, exclusive of direct attachment via the peptide backbone. Typically the attachment of $L_6$ to the N-terminus of SPA-$NH_2$ is via an amide linkage. In one embodiment, $L_6$ contains a hydrocarbon chain containing 8 atoms and a single double bond of cis- or trans-configuration, or a mixture thereof. In another embodiment, $L_6$ contains a hydrocarbon chain containing a single double bond, of cis- or trans-configuration, or a mixture thereof. In another embodiment, $L_6$ contains one oxygen atom internal to a hydrocarbon chain. In another embodiment, $L_6$ contains multiple oxygen atoms interspaced with carbon atoms, as in a poly(ethyleneglycol) system. In another embodiment, $L_6$ contains one sulfur atom internal to a hydrocarbon chain. In another embodiment, $L_6$ contains two sulfur atoms that are covalently attached in a manner other than a disulfide bond. In another embodiment, $L_6$ contains an ester functionality internal to a hydrocarbon chain. In another embodiment, $L_6$ contains a thioester functionality internal to a hydrocarbon chain. In another embodiment, $L_6$ contains a hydrocarbon chain with an internal polysubstituted triazole, or a substituted 4,5,6,7,8,9-hexahydro-1H-cycloocta[d][1,2,3]triazole, or a substituted 8,9-dihydro-1H-dibenzo[3,4:7,8]cycloocta[1,2-d][1,2,3]triazole, or a substituted 2,3,8,9-tetrahydrodibenzo[3,4:7,8]cycloocta[1,2-d]isoxazole, or a substituted 4a,5,6,7,8,9,10,10a-octahydrocycloocta[d]pyridazine. In some embodiments, the linker is selected from an ether (including a polyether such as poly(ethyleneglycol)), ester, amide, thioether, thioester or a hydrocarbon chain, which may or may not contain internal unsaturation (such as a single or multiple double bonds, or one or more alkynes) and may or may not contain an internal structure such as a carbocycle or heterocycle which may or may not function as a dye or chromophore and may or may not branch to a pendant moiety such as biotin or a dye or chemical probe or reactive group or E3 ligase ligand. $L_1$ may or may not contain one or more carbon atoms, or one or more sulfur atoms, or one or more oxygen atoms, or one or more nitrogen atoms. This list is not meant to be exhaustive and one skilled in the art can readily imagine other covalent linking strategies. $L_6$ may be branched, or $L_6$ may be chemical derivatives of the aforementioned non-inclusive possibilities. Non-limiting examples of these derivatives include epoxidation or aziridination or cyclopropanation or dihydroxylation of a double bond.

In certain embodiments, the present invention provides compounds encompassed within Formula VII:

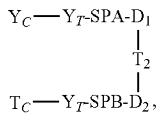

including pharmaceutically acceptable salts, solvates, and/or prodrugs thereof; wherein $Y_C$-$Y_T$-SPA- and $Y_C$-$Y_T$-SPB- are independently a compound of Formula I, or a compound of Formula II, or a compound of Formula III. The C-termini of the two stapled peptides SPA and SPB are linked via tether $D_1T2D_2$. In some instances, D1 and D2 might be (optionally substituted) nitrogens, thereby being part of amide bonds with the C-termini. D1 and D2 are independent of one another and might contain N, O or S as the atom of attachment. SPA and SPB are synthesized on 2-chlorotrityl chloride resin, or some other resin that would allow for the cleavage from resin of a protected peptide. An example of this chemistry can be found in Alhassan et al. Green Chem. 2020, 22, 2840-2845. The protected stapled peptides as free carboxylic acids may also be synthesized by traditional solution phase methods. The protected peptide acids may be reacted with a polyfunctional molecule such as a polyamine or amino alcohol to create a compound of Formula VII in protected form. Global deprotection would afford a compound of Formula VII. In some instances, SPA and SPB might independently be reacted with complementary click chemistry partners, for instance SPA might be reacted with an amino alkyne and SPB might be reacted with an amino azide. These new derivatives would product a compound of Formula VII, in protected form, under appropriate reaction conditions (e.g. a copper(I) species). Global deprotection would afford a compound of Formula VII.

In certain embodiments, the present invention provides compounds encompassed within Formula VIII: $Y_C$-$Y_T$-SPA-$T_2$-SPB-$NH_2$, including pharmaceutically acceptable salts, solvates, and/or prodrugs thereof; wherein $Y_C$-$Y_T$-SPA- and $Y_C$—$Y_T$-SPB- are independently a compound of Formula I, or a compound of Formula II, or a compound of Formula III. Compounds of formula VIII may be synthesized in a fashion similar to that for a compound of Formula I or Formula II or Formula III, with the substitution of $Y_C$ for a continuation of the synthesis, thereby elongating SPB, through a tether, to the production of SPA, etc. In another scenario, a protected peptide carboxylic acid SPA, as described for Formula VII, or a protected click chemistry partner, as described for Formula VII, is appended to SPB via chemistry known to one skilled in the art; for instance, amide bond formation or CuAAC reaction as appropriate. Global deprotection would afford a compound of Formula VIII.

In some embodiments, the compounds encompassed within Formulas I, II, III, IV, V, VI, VII, and VIII include amino acids selected from all standard amino acids, L-α-tert-butylglycine, D-α-tert-butylglycine, 0-(2-thienyl)-L-alanine, L-allo-isoleucine, 4,5-dehydro-L-leucine, D-homoleucine, L-homoleucine, 1-aminocyclopentane-1-carboxylic acid, D-allo-isoleucine, 3-(4-thiazolyl)-L-alanine, L-Homoarginine, 5,5,5-Trifluoro-DL-leucine, γ-carboxy γ-(di-tert-butyl ester)-L-glutamic acid, γ-carboxy γ-(di-tert-butyl ester)-D-glutamic acid, L-α-aminobutyric acid, D-α-aminobutyric acid, α,β-dehydro-2-aminobutyric acid, 4-nitro-L-phenylalanine, 4-chloro-L-phenylalanine, 4-chloro-D-phenylalanine, 4-fluoro-L-phenylalanine, 4-fluoro-D-phenylalanine, L-homophenylalanine, D-homophenylalanine, 3,4-dichloro-D-phenylalanine, 3-fluoro-L-phenylalanine, 4-iodo-L-phenylalanine, p-phenyl-L-Phenylalanine, p-phenyl-D-Phenylalanine, 4-bromo-L-phenylalanine, 4-bromo-D-phenylalanine, 2-chloro-L-phenylalanine, 2-chloro-D-phenylalanine, 3-cyano-L-phenylalanine, and 3-cyano-D-phenylalanine.

In some embodiments, the compounds encompassed within Formulas I, II, III, IV, V, VI, VII, and VIII are further conjugated with an additional therapeutic agent (e.g., thalidomide) (e.g., bifunctional compounds (e.g., PROTACs).

In some embodiments, the compounds encompassed within Formulas I, II, III, IV, V, VI, VII, and VIII have a central disubstituted amino acid with a geminal bis(tethered alkene) pattern at the alpha-carbon bracketed on both sides with a complementary (in terms of spacing and stereochemistry) mono-alkenyl residue. The geminal bis(tethered alkene) is typically symmetrically substituted, but this is not a requirement.

In any instance of a compound of Formula I, or a compound of Formula II, or a compound of Formula III, or a compound of Formula IV, or a compound of Formula V, or a compound of Formula VI, or a compound of Formula VII, or a compound of Formula VIII, a nitrogen atom that is part of the peptide backbone, or is part of the side chain of an amino acid, may be covalently attached to a chemical moiety that is not a hydrogen atom. In one embodiment, this chemical moiety is a hydrocarbon chain or a substituted hydrocarbon chain containing a reactive species that may or may not further participate in chemical reactions including, but not limited to, a ring closing metathesis reaction, esterification, amide formation, Diels-Alder reaction, etc.

In certain embodiments, the present invention provides an alpha-helical stapled peptide comprising hydrophobic amino acids and hydrophilic amino acids, wherein two or more amino acids of the peptide are connected to each other, wherein the peptide is capable of binding with the FAT domain of FAK.

In some embodiments, the peptide is capable of binding with one or more of the helix1-4 and helix2-3 portion of the FAT domain of the FAK protein. In some embodiments, the compound is capable of binding with one or more of the following amino acid residues within a wild type FAK protein: V928, I936, R962, and K955. However, the compound is capable of also binding additional amino acid residues of a FAK protein. In some embodiments, the peptide is capable of inhibiting interaction between FAK and paxillin. In some embodiments, the peptide is capable of disrupting FAK non-catalytic activity upon inhibition of interaction between FAK and paxillin.

In some embodiments, wherein the peptide is capable of one or more of the following:

- disrupting FAK non-catalytic activity upon inhibition of interaction between FAK and paxillin,
- disrupting FAK catalytic activity through direct binding of the FAT domain,
- inhibiting FAK related scaffolding function,
- inhibiting FAK protein-protein interactions mediated by the FAT domain,
- inhibiting binding of paxillin with the helix 1-4 region of the FAT domain of FAK,
- inhibiting binding of paxillin with the helix 2-3 region of the FAT domain of FAK,
- inhibiting FAK related apoptosis, proliferation, invasion, and/or metastasis,
- inhibiting FAK-paxillin interaction resulting inhibiting of FAK phosphorylation, paxillin phosphorylation, focal adhesion turnover, cell adhesion, migration, and/or invasion,
- inhibiting FAK-Leupaxin interaction through binding the FAT domain of FAK,
- inhibiting FAK-CD4 interaction through binding the FAT domain of FAK,
- inhibiting FAK-CD8 interaction through binding the FAT domain of FAK,
- inhibiting FAK-DCC interaction through binding the FAT domain of FAK,
- inhibiting paxillin LD2 and LD4 binding with respective binding partners,
- inhibiting CD4 and CD8 binding with respective binding partners,
- inhibiting CD4 and CD8 binding with Lck,
- inhibiting Leupaxin binding with respective binding partners,
- inhibiting DCC binding with respective binding partners,
- inhibiting interactions of FAK-related molecules including Pyk2, Vinculin, ILK, Actopaxin, PKL, Git1/2, Pax3, hic-5, and ARF.

In some embodiments, the amino acids at two or more positions selected from the group consisting of i, i+3, i+4, i+7, i+8, i+10 and i+11 (where i is an integer) are connected to each other.

In some embodiments, the stapled peptide comprises any one of SEQ ID Nos: 1-30, 36, and 37 as recited in Table 1.

TABLE 1

Table 1. Peptides and identifiers.

| SEQ ID NO: | Name | Sequence |
|---|---|---|
| 1 | 1967 | Ac-NLSELDRLLLELN-$NH_2$ (Ac-LD2-$NH_2$) |
| 2 | 1905 | Ac-NLS$R_8$LDRLLL$S_5$LN-$NH_2$ |
| 3 | 1906 | H-NLS$R_8$LDRLLN$S_5$LN-$NH_2$ |
| 4 | 1907 | Ac-NL$R_8$ELDRLL$S_5$ELN-$NH_2$ |
| 5 | 1910 | Ac-NL$R_8$QLDRLL$S_5$QLN-$NH_2$ |
| 6 | 1912 | Ac-NLAibELDRLLAibELN-$NH_2$ |
| 7 | 1913 | Ac-DL$R_8$ELDRLL$S_5$ELD-$NH_2$ |
| 8 | 1914 | Ac-NLSE$R_8$DRLLLE$S_5$N-$NH_2$ |
| 9 | 1919 | Ac-NLSE$S_5$DRL$S_5$LELN-$NH_2$ |
| 10 | 1920 | Ac-SLGSNL$R_8$ELDRLL$S_5$ELNAVQH-$NH_2$ |
| 11 | 1921 | Ac-NLSELDRL$R_5$LE$S_5$N-$NH_2$ |
| 12 | 1925 | Ac-NLSE$R_8$DRAALE$S_5$N-$NH_2$ |
| 13 | 1929 | Ac-RR$R_8$ARLRFM$S_5$QFY-$NH_2$ |
| 14 | 1931 | Ac-NLRE$S_5$DRL$S_5$RELN-$NH_2$ |
| 15 | 1933 | Ac-NL$R_8$EWDRLL$S_5$EWN-$NH_2$ |
| 16 | 2007 | Ac-NL$R_8$ELDRLW$S_5$ELN-$NH_2$ |
| 17 | 2009 | Ac-NL$R_8$ALDRLL$S_5$ELN-$NH_2$ |
| 18 | 2010 | Ac-NL$R_8$ALDALL$S_5$ELN-$NH_2$ |
| 19 | 2011 | Ac-$R_8$ELDRLL$S_5$-$NH_2$ |
| 20 | 2013 | Ac-NL$R_8$ELDRLL$S_5$ELN-$NH_2$ (unstapled) |
| 21 | 2014 | Ac-NL$R_8$EEDRLL$S_5$EEN-$NH_2$ |
| 22 | 2015 | Ac-NLSELDR$S_5$LLE$S_5$N-$NH_2$ |
| 23 | 2017 | Ac-N$R_8$SELDRL$S_5$LELN-$NH_2$ |
| 24 | 2022 | Ac-NLSE$R_5$DR$S_5$LLELN-$NH_2$ |
| 25 | 2024 | Ac-N$R_5$SE$S_5$DRLLLELN-$NH_2$ |
| 26 | 2028 | Ac-NL$R_8$ELDKLL$S_5$ELN-$NH_2$ |
| 27 | 2006 | $N_3(CH_2CH_2O)_3CH_2CO$-NL$R_8$ELDRLL$S_5$ELN-$NH_2$ (Az-1907) |
| 28 | 2012 | Myristoyl-NL$R_8$ELDRLL$S_5$ELN-$NH_2$ |
| 29 | 2020 | Myristoyl-NL$R_8$EEDRLL$S_5$EEN-$NH_2$ |
| 30 | 2029 | Ac-NL$R_8$ELDK(myristoyl)LL$S_5$ELN-$NH_2$ |
| 31 | 2025 | 4-Dodecyl-(Az-1907) |
| 32 | 2018 | (Az-1907)-[DBCO-PEG-DBCO]-(Az-1907) |
| 33 | 2021 | (Az-1907)-PEG18-(Az-1907) |
| 34 | 2023 | (Az-1907)-PEG10-(Az-1907) |
| 35 | 2019 | Thalidomide-(Az-1907) |
| 36 | 1916 | Ac-SAT$R_8$ELDELM$S_5$SLSD-$NH_2$ |
| 37 | 1917 | Ac-SATRE$S_5$DEL$S_5$ASLSD-$NH_2$ |
| 38 | 2030 | (PF-562271 analog)-(Az-1907) |
| 39 | 2016 | RhoB-1907 |

Abbreviations: $R_8$: (R)-2-(7-octenyl)alanine; $S_5$: (S)-2-(4-pentenyl)alanine; $R_5$: (R)-2-(4-pentenyl)alanine; Az: 2-(2-(2-(2-azidoethoxy)ethoxy)ethoxy)acetyl; Aib: 2-aminoisobutyric acid; DBCO: 3-amino-1-(2-azatricyclo[10.4.0.$0^{4,9}$]hexadeca-1(16),4,6,8,12,14-hexaen-10-yn-2-yl)propan-1-one; RhoB: rhodamine B; or derivatives thereof. Unless otherwise stated, the peptides are the product(s) of an intramolecular ring-closing metathesis reaction; double bond geometry has not been established or quantified. These sequences are abbreviated and may refer to "click" chemistry products. FIG. 14 shows the structures of peptides P29-P34, P37 and P38.

As recited in Table 1: $R_8$ refers to (R)-2-(7-octenyl) alanine; $S_5$ refers to (S)-2-(4-pentenyl) alanine; $R_5$ refers to (R)-2-(4-pentenyl) alanine; Aib refers to 2-aminoisobutyric acid;

Az refers to 2-(2-(2-(2-azidoethoxy)ethoxy)ethoxy) acetyl; Ac refers to acetyl; DBCO refers to 3-amino-1-(2-azatricyclo[10.4.0.$0^{4,9}$]hexadeca-1(16),4,6,8,12,14-hexaen-10-yn-2-yl)propan-1-one; and wherein standard one letter amino acid codes are used.

In some embodiments, the peptide is further conjugated with an imaging agent. In some embodiments, the imaging agent is 5- or 6-carboxytetramethylrhodamine (TAMRA) or a mixture of isomers.

In certain embodiments, the present invention provides a pharmaceutical composition comprising one or more of such stapled peptides in a pharmaceutically acceptable carrier.

In certain embodiments, the present invention provides a composition comprising two or more of such stapled peptides, wherein the two or more stapled peptides are tethered together via a linker (e.g., a PEG based linker).

In certain embodiments, the present invention provides a method of treating, ameliorating, or preventing a hyperproliferative disease in a patient comprising administering to said patient a therapeutically effective amount of a pharmaceutical composition comprising one or more of such stapled peptides.

In some embodiments, the hyperproliferative disease is cancer (e.g., a cancer characterized with FAK expression, FAK pathway activation, FAK dependence, FAK activity and/or FAK-paxillin related activity).

In some embodiments, patient is a human patient.

In some embodiments, the method further comprises administering to said patient one or more anticancer agents. In some embodiments, the anticancer agent is a chemotherapeutic agent. In some embodiments, the anticancer agent is radiation therapy.

In certain embodiments, the present invention provides a kit comprising one or more of such stapled peptides and instructions for administering such stapled peptides to a patient having a hyperproliferative disease.

In certain embodiments, the stapled peptides are capable of binding with other proteins having a similar FAT domain type structure (e.g., Pyk2, Vinculin, ILK, Actopaxin, PKL, Git1/2, Pax3, hic-5, and ARF).

The invention further provides processes for preparing any of the stapled peptides of the present invention through following at least a portion of the techniques recited in Example I.

The invention also provides the use of such stapled peptides to induce cell cycle arrest and/or apoptosis in cells containing FAK proteins (e.g., functional FAK proteins, non-functional FAK proteins, aberrantly regulated FAK proteins, mutant FAK proteins). The invention also relates to the use of such stapled peptides for sensitizing cells to additional agent(s), such as inducers of apoptosis and/or cell cycle arrest, and chemoprotection of normal cells through the induction of cell cycle arrest prior to treatment with chemotherapeutic agents.

As noted, the stapled peptides of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, such stapled peptides can be used to treat, ameliorate, or prevent cancer that is characterized by resistance to cancer therapies (e.g., those cancer cells which are chemoresistant, radiation resistant, hormone resistant, and the like). In certain embodiments, the cancer is multiple myeloma, acute myeloid leukemia, melanoma, breast cancer, head or neck cancers, colon cancer, lung cancer, ovarian cancer, prostate cancer, and/or pancreatic cancer. In other embodiments, such stapled peptides can be used to treat hyperproliferative diseases characterized by expression of functional FAK protein activity and, in particular, functional FAK-paxillin related activity.

The stapled peptides of the invention are useful for the treatment, amelioration, or prevention of disorders, such as those related to FAK expression and/or activity (e.g., bone disease, regulation of bone density, fibrotic disorders, rheumatoid arthritis, osteoarthritis, neurological disorders, Alzheimer's disease, pro-inflammatory, gene expression, chronic inflammatory diseases, vascular inflammation, vitiligo, psoriasis, acute lung injury (ALI), cardiovascular disease, diabetic nephropathy, HHV-8 (Kaposi sarcoma-associated herpesvirus (KSHV), Ventilator Induced Lung Injury, and/or AIDS & HIV-CD4 related.

The stapled peptides of the invention are useful for the treatment, amelioration, or prevention of disorders, such as those related to FAK and Pyk2 expression and/or activity (e.g., chronic diseases such as cardiovascular disease, bone disease, fibrosis (e.g., liver fibrosis, lung fibrosis, keloids, etc.), rheumatoid arthritis, and neurological disorders).

The invention also provides kits comprising such stapled peptides of the invention and instructions for administering to an animal. The kits may optionally contain other therapeutic agents, e.g., anticancer agents or apoptosis-modulating agents.

The present disclosure further provides bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited. An exemplary advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer (e.g., a cancer characterized with FAK expression, FAK pathway activation, FAK dependence, FAK activity and/or FAK-paxillin related activity.

In an additional aspect, the disclosure provides bifunctional or PROTAC compounds, which comprise an E3 Ubiquitin Ligase binding moiety (e.g., a ligand for an E3 Ubquitin Ligase or "ULM" group), and a moiety that binds a target protein (e.g., a protein/polypeptide targeting ligand or "PTM" group) (e.g., a FAT domain of FAK) such that the target protein/polypeptide is placed in proximity to the ubiquitin ligase to effect degradation (and inhibition) of that protein (e.g., inhibit interaction between paxillin and FAK). In certain embodiments, the PTM is any of the peptides as described herein having affinity for the FAT domain of FAK (e.g., thereby inhibiting interaction between FAK and paxillin) (e.g., any of the peptides encompassed within Formulas I-VI) (e.g., any of the peptides recited in Table 1). In some embodiments, the ULM is a von-Hippel-Lindau (VHL) ligase, cereblon, mouse double minute 2 (MDM2), and/or inhibitor of apoptosis protein (IAP) E3 ligase binding moiety. For example, the structure of the bifunctional compound can be depicted as PTM-ULM.

The respective positions of the PTM and ULM moieties, as well as their number as illustrated herein, is provided by way of example only and is not intended to limit the peptides in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as PTM-L-ULM, where PTM is a protein/polypeptide targeting moiety (e.g., any of the compounds as described herein showing modulatory activity against modulatory activity against FAK), L is a linker, and ULM is a VHL, cereblon, MDM2, or IAP E3 ligase binding moiety binding moiety.

Such embodiments are not limited to a specific type of linker. In some embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, azido, or heterocycle group. In certain embodiments, the linker is a dye compound. In certain embodiments, the linker is photoreactive compound. In certain embodiments, the linker may be asymmetric or symmetrical. In some embodiments, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ULM group and PTM group may be covalently linked to the linker group through any group which is appropriate and stable to the chemistry of the linker. In exemplary aspects of the present invention, the linker is independently covalently bonded to the ULM group and the PTM group in certain embodiments through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain aspects where the PTM group is a ULM group, the target protein for degradation may be the ubiquitin ligase itself. In certain exemplary aspects, the linker may be linked to an optionally substituted alkyl, alkylene, alkene or alkyne group, an aryl group or a heterocyclic group on the ULM and/or PTM groups.

In certain embodiments, the compounds as described herein comprise multiple ULMs, multiple PTMs, multiple chemical linkers, or any combinations thereof.

In some embodiments, the present invention provides a method of one or more of the following:

- disrupting FAK non-catalytic activity upon inhibition of interaction between FAK and paxillin,
- disrupting FAK catalytic activity through direct binding of the FAT domain,
- inhibiting FAK related scaffolding function,
- inhibiting FAK protein-protein interactions mediated by the FAT domain,
- inhibiting binding of paxillin with the helix 1-4 region of the FAT domain of FAK,
- inhibiting binding of paxillin with the helix 2-3 region of the FAT domain of FAK,
- inhibiting FAK related apoptosis, proliferation, invasion, and/or metastasis,
- inhibiting FAK-paxillin interaction resulting inhibiting of FAK phosphorylation, paxillin phosphorylation, focal adhesion turnover, cell adhesion, migration, and/or invasion,
- inhibiting FAK-Leupaxin interaction through binding the FAT domain of FAK,
- inhibiting FAK-CD4 interaction through binding the FAT domain of FAK,
- inhibiting FAK-CD8 interaction through binding the FAT domain of FAK,
- inhibiting FAK-DCC interaction through binding the FAT domain of FAK,
- inhibiting paxillin LD2 and LD4 binding with respective binding partners,
- inhibiting CD4 and CD8 binding with respective binding partners,
- inhibiting CD4 and CD8 binding with Lck,
- inhibiting Leupaxin binding with respective binding partners,
- inhibiting DCC binding with respective binding partners,
- inhibiting interactions of FAK-related molecules including Pyk2, Vinculin, ILK, Actopaxin, PKL, Git1/2, Pax3, hic-5, and ARF; comprising administering a bifunctional compound as described herein comprising an ULM and a PTM, in certain embodiments linked through a linker moiety, as otherwise described herein, wherein the ULM is coupled to the PTM and wherein the ULM recognizes a ubiquitin pathway protein and the PTM recognizes the target protein such that degradation of the target protein occurs when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

DETAILED DESCRIPTION OF THE INVENTION

Figure 1:
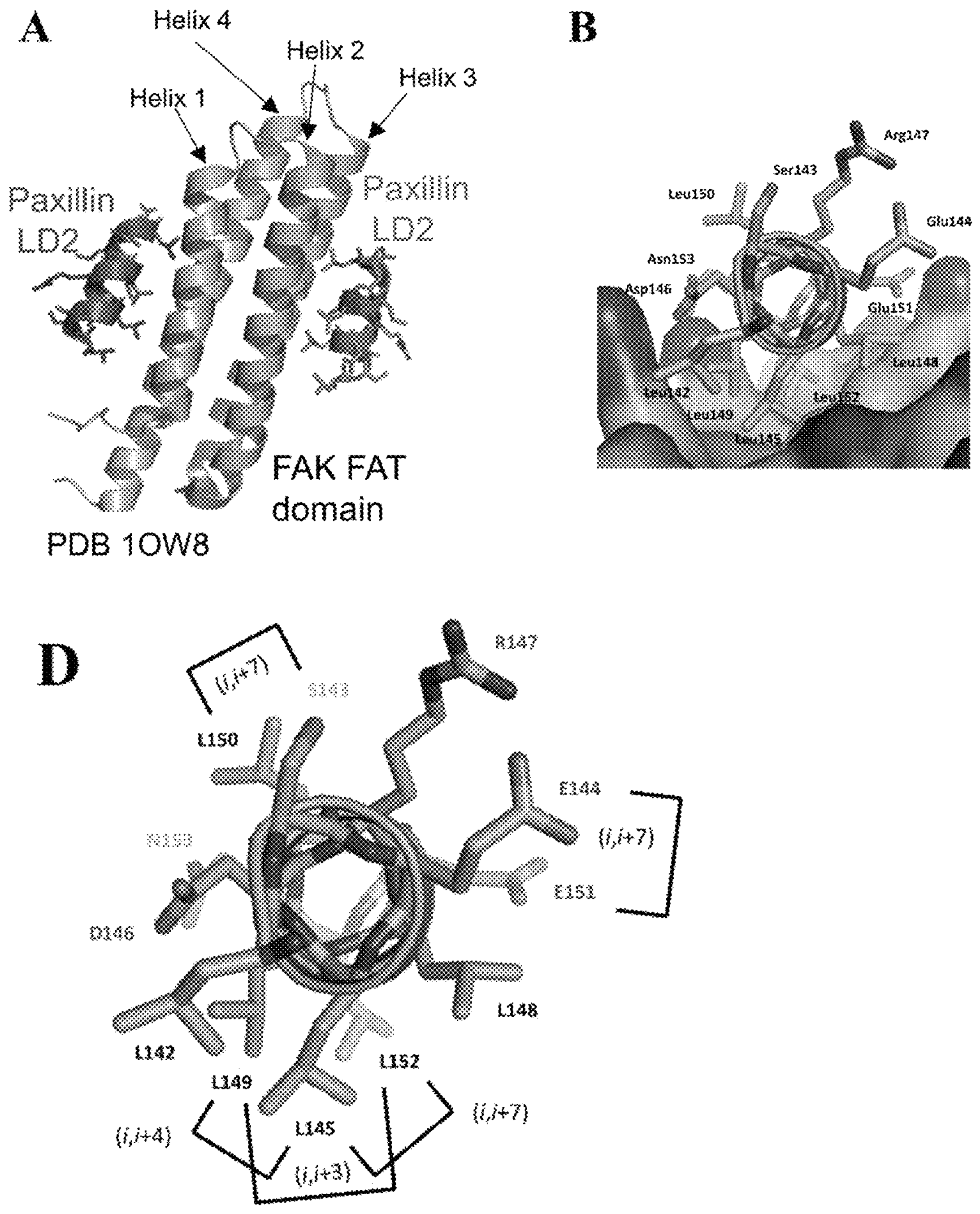
FIG. 1: Overview of stapled alpha-helical peptides targeting the FAT domain of FAK. A. Crystal structure of the FAT-paxillin interaction (PDB 10W8) containing two paxillin LD2 motifs (shown in green & magenta). Stapled peptides are based off the structure of the paxillin LD2 motif. B. Zoomed inset of the FAT Helix 2-3 binding interface with paxillin LD2. C. Helix wheel structural analysis of LD2-FAT inter- and intramolecular interactions. D. 3D representation of stapling strategies used for peptide optimization. E. Summary of amino acid modifications used in peptide design strategies.

Focal adhesion kinase (FAK) is a non-receptor tyrosine kinase that is overexpressed in numerous tumors including melanoma, breast, colon, ovarian, pancreatic, glioblastoma, and others (1), and has been shown to be a necessary component for human cancer progression (2-4).

From a biological standpoint, FAK is involved in motility, invasion, angiocrine signaling, lymphangiogenesis, metastasis, and epithelial-mesenchymal transition (EMT) (5-8). FAK also sequesters and inactivates pro-apoptotic proteins like p53 and RIP to enhance the survival signals necessary for a cancer to invade and metastasize (9, 10). FAK's role in cancer has been confirmed by clinical prognostic studies, genetically-engineered mouse models, and knockout studies (11-15).

FAK knockdown results in robust activation of apoptosis and growth arrest in cancer cells with no effects in normal cells (16, 17). Conversely, FAK-kinase inhibitors have a partial effect on apoptosis/tumor growth (18-20) and it has been hypothesized that the FAK scaffold is the major modulator of FAK-dependent anti-apoptosis (21). FAK directly binds p53 to suppress p53-mediated apoptosis and disruption of the FAT domain by adenoviral FAK-CD was shown to induce apoptosis in cancer cells (22). It has been shown that FAK-kinase inhibitors do not drastically inhibit FAK phosphorylation at autophosphorylation residue Y397 and Receptor Tyrosine Kinases (RTKs) transphosphorylate FAK as a drug resistance mechanism (23). Furthermore, FAK-kinase inhibitors (e.g., FAK-kinase catalytic domain inhibitors) have shown limited efficacy in Phase I/II clinical trials (24-26).

The FAT domain is a four-helical bundle at the C-terminus of FAK that contains key residue Y925 and is involved in multiple protein-protein interactions at the focal adhesion site. Numerous data have emerged showing the importance of the Focal Adhesion Targeting (FAT) domain as the initiator of FAK activation through its multiple interactions with paxillin, Leupaxin, CD4, and DCC (27-29). The integrity of the FAT domain is essential for localization of FAK to focal adhesions, association with integrins/RTKs, and downstream FAK signaling (30-32). Mutation of the FAT domain demonstrated dramatic biological effects on metastasis, invasion, and apoptosis (33, 34). As such, experiments conducted during the course of developing embodiments for the present invention hypothesized that peptide inhibitors that target the FAT domain will be more efficacious than FAK-kinase inhibitors and less-prone to drug resistance mechanisms.

Paxillin is a major focal adhesion adaptor protein that integrates key cytoskeletal proteins and signaling molecules such as Vinculin, FAK, Actin, Src, and Crk (35). FAK localization to the focal adhesion is mediated by the FAK-paxillin interaction and mutation of the binding site was shown have drastic effects on FAK phosphorylation, paxillin phosphorylation, focal adhesion turnover, cell adhesion, migration, and invasion (34, 36). Paxillin contains two alpha helical LD motifs (LD2 and LD4) that are required for binding to the FAT domain of FAK. The FAT-paxillin LD2/LD4 interaction is well-characterized, has a $K_D$ of 50-100 μM, and has been validated by multiple orthogonal assays (X-ray, SPR, ITC, NMR, FP, and mutagenesis). LD2 and LD4 interact at two separate hydrophobic patches on the FAT domain (Helix 1-4, Helix 2-3) and disruption of both sites is required for maximal biological effect (27, 37, 38).

Experiments conducted during the course of developing embodiments for the present invention synthesized and optimized peptides capable of effectively targeting FAK non-catalytic function through binding of the FAT domain and thereby inhibiting, for example, FAK-paxillin interaction (e.g., FAK-LD2 domain of paxillin). In particular, the present invention provides stapled LD2 domain peptides capable of inhibiting FAK-paxillin interaction. These LD2 peptides represent a significant advantage over existing FAK inhibitors due to the ability to disrupt FAK protein-protein interactions (PPIs) and therefore provide novel anti-cancer effects.

As such, the present invention provides a new class of peptides which function as inhibitors of focal adhesion kinase (FAK) activity through binding with its focal adhesion targeting (FAT) domain and thereby inhibiting FAK-paxillin interaction (e.g., LD2 peptides). Indeed, in certain embodiments, the present invention provides LD2 peptides capable of inhibiting FAK-paxillin interaction. In some embodiments, such LD2 peptides are amphipathic alpha-helical stapled peptides comprising hydrophobic amino acids and hydrophilic amino acids, wherein two or more amino acids of the peptide are connected to each other.

As used herein, the term “stapled peptide” means that peptide regions are connected to each other. In some embodiments, in order to increase the chemical stability and secondary structure of alpha-helices, the i position and i+ position of the alpha-helix can be stapled using various covalent bonding methods. Specifically, the amino acids at one or more positions selected from the group consisting of i, i+3, i+4, i+7, i+8, i+10 and i+11 (where i is an integer) may be stapled. Amino acids may be stapled by a covalent bond and linker moeity to thereby increase the cell-penetrating ability. In some cases, two or more amino acid positions selected from the group consisting of i, i+3, i+4, i+7, i+8, i+10 and i+11 (where i is an integer) may be stapled.

Typically, two amino acids may be connected to each other by a disulfide bond, a carbon-carbon double bond, an azide-alkyne cycloaddition, or an amide bond. Examples of the method for linking two amino acids to each other include introduction of disulfide between two amino acid positions, introduction of a carbon-carbon double bond by a metathesis reaction, introduction of an amide bond, introduction of a short linker by the Michael reaction, and the like. Such stapling makes it highly possible to prepare a cell-penetrating peptide having an improved cell-penetrating ability and desired chemical stability.

If a peptide is alpha-helical, two or more amino acids of the peptide can be connected to each other exclusive of the basic peptide backbone, creating a cyclic structure. The size of the cyclic ring may vary depending on the position of the amino acid and length of the linking moiety. One or more staples may be contained in the peptide.

In a particular embodiment of the present invention, one or more amino acids of the peptide may be functionalized with a double bond-containing compound. For example, amino acids can be connected to each other by a ring structure produced by a ring-closing metathesis between double bond-containing compounds. The functionalized amino acids may be amino acids substituted with an alkenyl side-chain. The alkenyl side-chain may be one or more selected from the group consisting of 2-propylenyl, 3-butenyl, 4-pentenyl, 5-hexenyl, 6-heptenyl, 7-octenyl, 8-nonenyl, 9-decenyl, 10-undecenyl and 11-dodecenyl groups.

The amino acids of the peptide are not specifically limited as long as they can maintain the $\alpha$-helical structure while showing amphipathic properties. For example, the hydrophilic amino acid may be one or more selected from the group consisting of arginine, lysine, and histidine, and the hydrophobic amino acid may be one or more selected from the group consisting of leucine, valine, tryptophan, phenylalanine, tyrosine, and isoleucine. Non-natural amino acids may also be utilized in the peptide structure.

Specifically, in an example of the present invention, an amphipathic alpha-helical stapled peptide capable of inhibiting FAK-paxillin interaction was generated.

As noted, in certain embodiments, the present invention provides LD2 peptides capable of inhibiting FAK-paxillin interaction. In some embodiments, such LD2 peptides are amphipathic alpha-helical stapled peptides comprising hydrophobic amino acids and hydrophilic amino acids, wherein two or more amino acids of the peptide are connected to each other.

Specifically, such stapled LD2 peptides capable of inhibiting FAK-paxillin interaction may comprise any one of the following sequences, and are produced by introducing the carbon-carbon double bond through a metathesis reaction. In the following sequences, $R_8$ denotes (R)-2-(7'-octenyl) alanine, $S_5$ denotes (S)-2-(4'-pentenyl) alanine and $R_5$ denotes (R)-2-(4'-pentenyl) alanine.

In some embodiments, two or more of the LD2 peptides are tethered together with a linker (e.g., a PEG based linker) that is constructed via chemistries that are compatible with the various functionalities and solvent and known to those skilled in the art (e.g., linked via “click” chemistry)).

In some embodiments, the LD2 peptides are further conjugated with an imaging agent (e.g., conjugated with (5-/6-)carboxytetramethylrhodamine (TAMRA)).

An important aspect of the present invention is that the LD2 peptides of the invention induce cell cycle arrest and/or apoptosis and also potentiate the induction of cell cycle arrest and/or apoptosis either alone or in response to additional apoptosis induction signals (e.g., through inhibiting FAK non-catalytic activity) (e.g., through inhibiting FAK-paxillin interaction). Therefore, it is contemplated that such LD2 peptides sensitize cells to induction of cell cycle arrest and/or apoptosis, including cells that are resistant to such inducing stimuli. The LD2 peptides of the present invention can be used to induce apoptosis in any disorder that can be treated, ameliorated, or prevented by the induction of apoptosis. In one embodiment, the LD2 peptides can be used to induce apoptosis in cells comprising functional FAK activity. In one embodiment, the LD2 peptides can be used to inhibit cancer metastasis. In one embodiment, the LD2 peptides can be used to inhibit angiogenesis.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head and neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms’ tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi’s sarcoma, polycythemia vera, essential thrombocytosis, Hodgkin’s disease, non-Hodgkin’s lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having FAK activity and/or FAK-paxillin related activity.

Some embodiments of the present invention provide methods for administering an effective amount of an LD2 peptide of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed stapled peptides (LD2 peptides) are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); BCL-2 family inhibitors (VENCLEXTA); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., Butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide an LD2 peptide of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide); and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 4 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 4

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H -pyrazolo[3,4-d]pyrimidin-4-one monosodium salt) | Zyloprim | GlaxoSmithKline, Research Triangle Park, NC |
| Altretamine (N,N,N',N',N",N",- hexamethyl-1,3,5-triazine-2, 4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-O, O']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3- (trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |

TABLE 4-continued

| | | |
|---|---|---|
| Daunorubicin HCl, daunomycin ((1 S ,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L- lyxo -hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax- 11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy] -8-glycolyl-7,8,9,10-tetrahydro-6,8,11- trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino- hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b -D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |

TABLE 4-continued

| | | |
|---|---|---|
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)- propyl]-[N-[2-bis(carboxymethyl)amino]-2-(methyl) - ethyl]glycine) | Zevalin | Biogen IDEC, Inc., Cambridge MA |
| Idarubicin (5, 12-Naphthacenedione, 9-acetyl-7-[(3-amino-2,3,6-trideoxy-(alpha)-L- lyxo - hexopyranosyl)oxy]-7,8,9,10-tetrahydro-6,9,11-trihydroxyhydrochloride, (7S- cis )) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesyilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4- piperi-dinopiperidino)carbonyloxy]-1H-pyrano[3', 4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4 -Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5, 6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)- 6 -methylpregna- 4,6- diene-3,20- dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H -purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2- [(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |

TABLE 4-continued

| | | |
|---|---|---|
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R, 3 S)- N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11 - 17 -adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1 -methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2 -deoxy - 2 - [[(methylnitrosoamino)carbonyl]amino] - a(and b ) - D - glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2- thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H - purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |

TABLE 4-continued

| | | |
|---|---|---|
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2- [1,2,3,4,6,11-hexahydro-2,5,12-trihydroxy-7 methoxy-6,11-dioxo-[[4 2,3,6-trideoxy-3- [(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}$•$H_2SO_4$) | Velban | Eli Lilly |
| Vincristine ($C_{46}H_{56}N_4O_{10}$•$H_2SO_4$) | Oncovin | Eli Lilly |
| Vinorelbine (3' ,4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB–, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering an LD2 peptide of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, an LD2 peptide of the invention and one or more therapeutic agents or anticancer agents are administered to an animal under one or more of the following conditions: at different periodicities, at different durations, at different concentrations, by different administration routes, etc. In some embodiments, the LD2 peptide is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the LD2 peptide is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the LD2 peptide and the therapeutic or anticancer agent are administered concurrently but on different schedules, e.g., the LD2 peptide is administered daily while the therapeutic or anticancer agent is administered once a week, once every two weeks, once every three weeks, or once every four weeks. In other embodiments, the LD2 peptide is administered once a week while the therapeutic or anticancer agent is administered daily, once a week, once every two weeks, once every three weeks, or once every four weeks.

Compositions within the scope of this invention include all compositions wherein the LD2 peptides of the present invention are contained in an amount which is effective to achieve its intended purpose. While individual needs vary, determination of optimal ranges of effective amounts of each component is within the skill of the art.

In addition to administering the stapled peptide (e.g., LD2 peptide) as a raw peptide, the LD2 peptides of the invention may be administered as part of a pharmaceutical preparation containing suitable pharmaceutically acceptable carriers comprising excipients and auxiliaries which facilitate processing of the LD2 peptides into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active peptide(s), together with the excipient. In some embodiments, the formulation of the LD2 peptide can also be liposomal in nature. In some embodiments, the liposomal formulation of the peptides (e.g., LD2, LD4) may be consisting of HSPC, Cholesterol, PEG2000-DSPE, DSPC, DOPE, DOTAP, Triolein, EPC, DOPS, POPC, SM, DMPC, DMPG, DOPC, mPEG derivatives, MVL5, DOTMA, DDAB, DC-Cholesterol, GL67, DODMA, Soy phospholipids, cationic lipids, anionic lipids, neutral lipids in various combinations and/or ratios and/or buffer solutions. In some embodiments, the liposomal formulation of the peptides (e.g., LD2, LD4) may comprise a combination of one or any combination of sphingomyelin (SM), D-erythrose-sphingomyelin, D-erythrose dihydrosphingomyelin, palmitoylsphingomyelin, lysophospholipids, galactocerebroside, gangliosides, cerebrosides, glycerides, triglycerides, diglycerides, small alkyl chain phospholipids, phosphatidylcholine, egg phosphatidylcholine, soybean phosphatidylcholine, dipalmitoylphosphatidylcholine (DPPC), dimyristoylphosphatidylcholine, 1-palmitoyl-2-oleoyl-phosphatidylcholine (POPC), 1,2-dimyristoyl-sn-glycero-3-phosphatidylcholine (DMPC), 1,2-distearoyl-sn-glycero-3-phosphatidylcholine (DSPC), distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipahnitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, ceramides, a phosphatidylserine, dimyristoylphosphatidylserine, dipalmitoylphosphatidylserine, brain phosphatidylserine, brain sphingomyelin, egg sphingomyelin, milk sphingomyelin, palmitoyl sphingomyelin, phytosphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives, lyso-phosphotydyl choline, lyso-sphingomyelin, dioleoyl-sn-glycero-3-phosphoethanolamine-N-[3-(2-pyridyldithio) propionate](DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], Lyso phoshphatidic acid, Lyso phosphatidyicholine, OA-$NO_2$ (nitrated oleic acid 9- and 10-nitro-cis-octedecenolic acids), $LNO_2$ (nitrated linoleic Acid 9-, 10-, 12- and 13-nitro-cis-octedecadienoic acids), AA-$NO_2$ (nitrated Arachidonic Acid 5-, 6-, 8-, 9-, 11-, 12-, 14-, and 15-nitro-cis-eicosatetraenoic acids), $CLNO_2$ (nitrated cholesteryl linoleate cholestaryl-9-, 10-, 12- and 13-nitro-cis-octedecadiencates), fatty acid, omega-3 polyunsaturated fatty acids, hexadecatrienoic acid (HTA; 16:3 (n-3); all-cis-7,10,13-hexadecatrienoic acid), α-Linolenic acid (ALA; 18:3 (n-3); all-cis-9,12,15-octadecatrienoic acid), stearidonic acid (SDA; 18:4 (n-3); all-cis-6,9,12,15-octadecatetraenoic acid), eicosatrienoic acid (ETE; 20:3 (n-3); all-cis-11,14,17-eicosatrienoic acid), eicosatetraenoic acid (ETA; 20:4 (n-3); all-cis-8,11,14,17-eicosatetraenoic acid), eicosapentaenoic acid (EPA; 20:5 (n-3); all-cis-5,8,11,14,17-eicosapentaenoic acid), heneicosapentaenoic acid (HPA; 21:5 (n-3); all-cis-6,9,12,15,18-heneicosapentaenoic acid); docosapentaenoic acid (DPA; clupanodonic acid; 22:5 (n-3); all-cis-7,10,13,16,19-docosapentaenoic acid), docosahexaenoic acid (DHA; 22:6 (n-3); all-cis-4,7,10,13,16,19-docosahexaenoic acid), tetracosapentaenoic acid; 24:5 (n-3); all-cis-9,12,15,18,21-tetracosapentaenoic acid), tetracosahexaenoic acid (Nisinic acid; 24:6 (n-3), all-cis-6,9,12,15,18,21-tetracosahexaenoic acid), sphingosine-1-phosphate analogs, sphingosine-1-phosphate antagonists, sphingosine-1-phosphate agonists, sphingosine-1-phosphate receptor agonists, sphingosine-1-phosphate receptor antagonists, and sphingosine-1-phosphate receptor analogs.

The pharmaceutical compositions of the invention may be administered to any patient which may experience the beneficial effects of the stapled peptides (LD2 peptides) of the invention. Foremost among such patients are mammals, e.g., humans, although the invention is not intended to be so limited. Other patients include veterinary animals (cows, sheep, pigs, horses, dogs, cats and the like).

The LD2 peptides and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active LD2 peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active stapled peptides (e.g., LD2 peptides) in the form of granules which may be mixed with fillers such as lactose, binders such as starches, and/or lubricants such as talc or magnesium stearate and, optionally, stabilizers. In soft capsules, the active stapled peptides (e.g., LD2 peptides) are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active peptides with a suppository base. Suitable suppository bases are, for example, natural or synthetic triglycerides, or paraffin hydrocarbons. In addition, it is also possible to use gelatin rectal capsules which consist of a combination of the active stapled peptides (e.g., LD2 peptides) with a base. Possible base materials include, for example, liquid triglycerides, polyethylene glycols, or paraffin hydrocarbons.

Suitable formulations for parenteral administration include aqueous solutions of the active peptides in water-soluble form, for example, water-soluble salts and alkaline solutions. In addition, suspensions of the active stapled peptides (e.g., LD2 peptides) as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the stapled peptides (e.g., LD2 peptides), compositions, and methods of the present invention. Other suitable modifications and adaptations of the variety of conditions and parameters normally encountered in clinical therapy and which are obvious to those skilled in the art are within the spirit and scope of the invention.

Example I

This example describes the generation of peptides which have an affinity for the FAT domain of FAK, and which are capable of blocking the interaction of paxillin with focal adhesion kinase (FAK), thereby inhibiting FAK activity related to FAK-paxillin interaction.

To develop inhibitors of the FAK-paxillin interaction experiments were conducted that took a stapled peptide approach which has the following advantages: (1) using the native peptide as a starting point, (2) spanning the entire interaction interface, (3) having a chemical moiety to enhance alpha helicity, cell permeability, and proteolytic stability, and (4) a workable molecule for straight-forward SAR analysis (amide chemistry).

Experiments were conducted that first started with synthesis of a series of cyclic peptides based on the paxillin LD2 motif and all-hydrocarbon stapling (FIG. 1). Solid phase peptide synthesis and the incorporation of olefinic amino tion by proteases, experiments were conducted that substituted natural amino acids with hydrophobic/polar/charged substitutions, non-natural amino acids, or D-amino acids (39) (FIG. 1).

To understand the structure-activity relationships of FAK stapled peptides, experiments were designed and 36 peptides were synthesized (Table 2) that varied based on staple strategy ((i, i+3), (i, i+4), and (i, i+7)), staple position, sequence length, amino acid composition, and homologous sequences (LD2, LD4, CD4, DCC, Leupaxin). Stapled peptide UACC-1907

Figure 2:
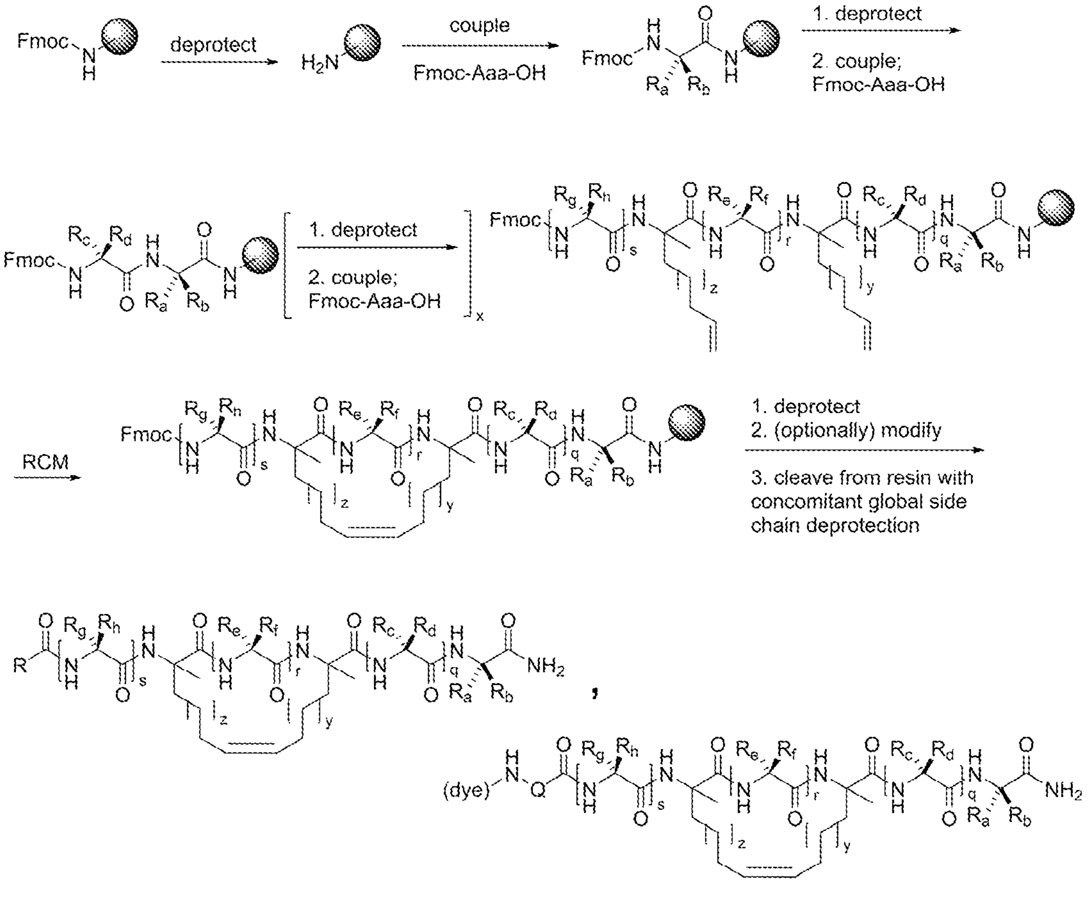
FIG. 2: Synthetic scheme for stapled peptide synthesis.

(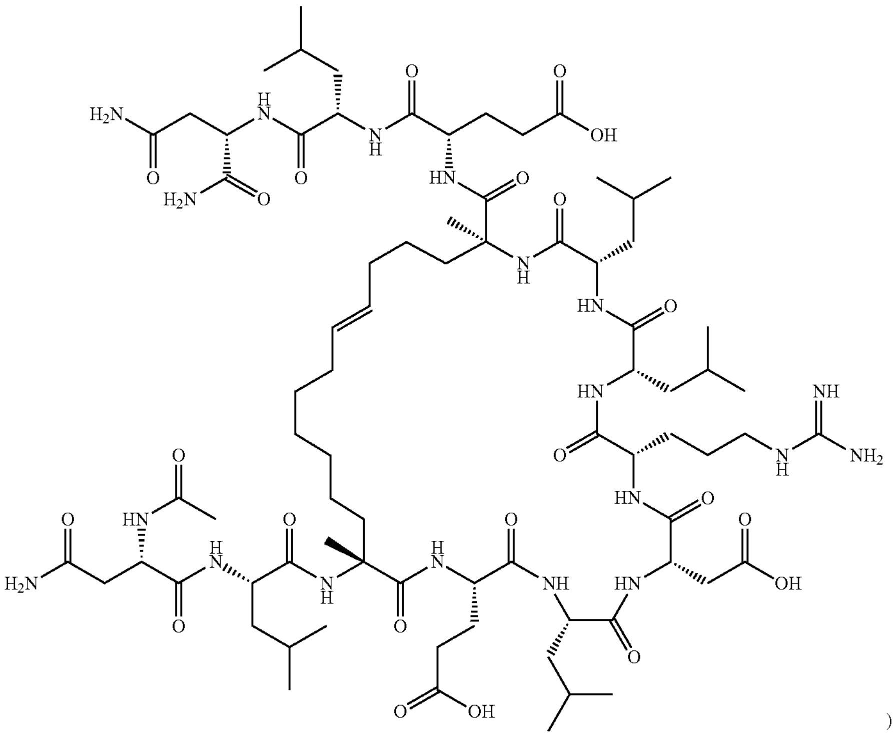)

acids ((R)-N-Fmoc-2-(4'-pentenyl)alanine and (S)-N-Fmoc-2-(7'-octenyl)alanine) in the i, i+7 position (six amino acids apart or two helical turns), followed by ring closing olefin metathesis and cleavage from the resin were used (FIG. 2) (see, Kim Y, et al., Nature Protocols. 2011; 6: 761-71). Stapled peptides were designed using molecular modeling and the x-ray crystal structure of the FAT-LD2 complex (PDB 10W8), in which residues that were not part of the binding interface were selected for replacement by olefinic amino acids. Residues part of the binding interface were also selected for SAR studies.

Figure 3:
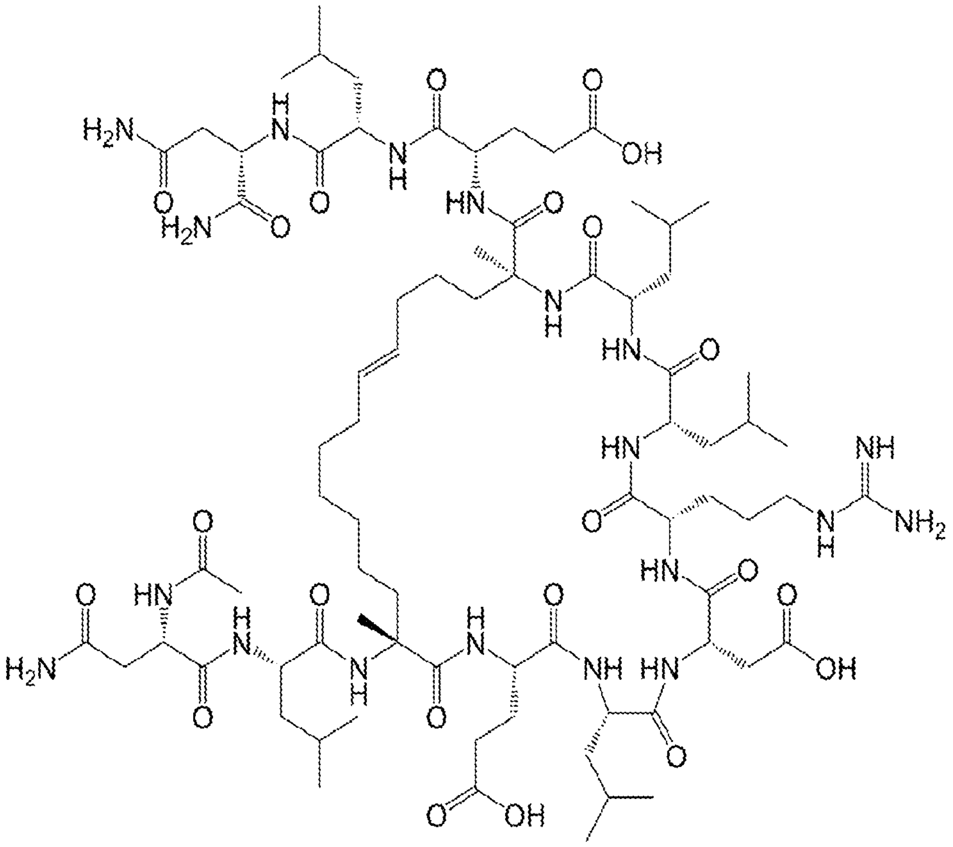
FIG. 3: Chemical structure of stapled peptide UACC-1907.
Figure 4:
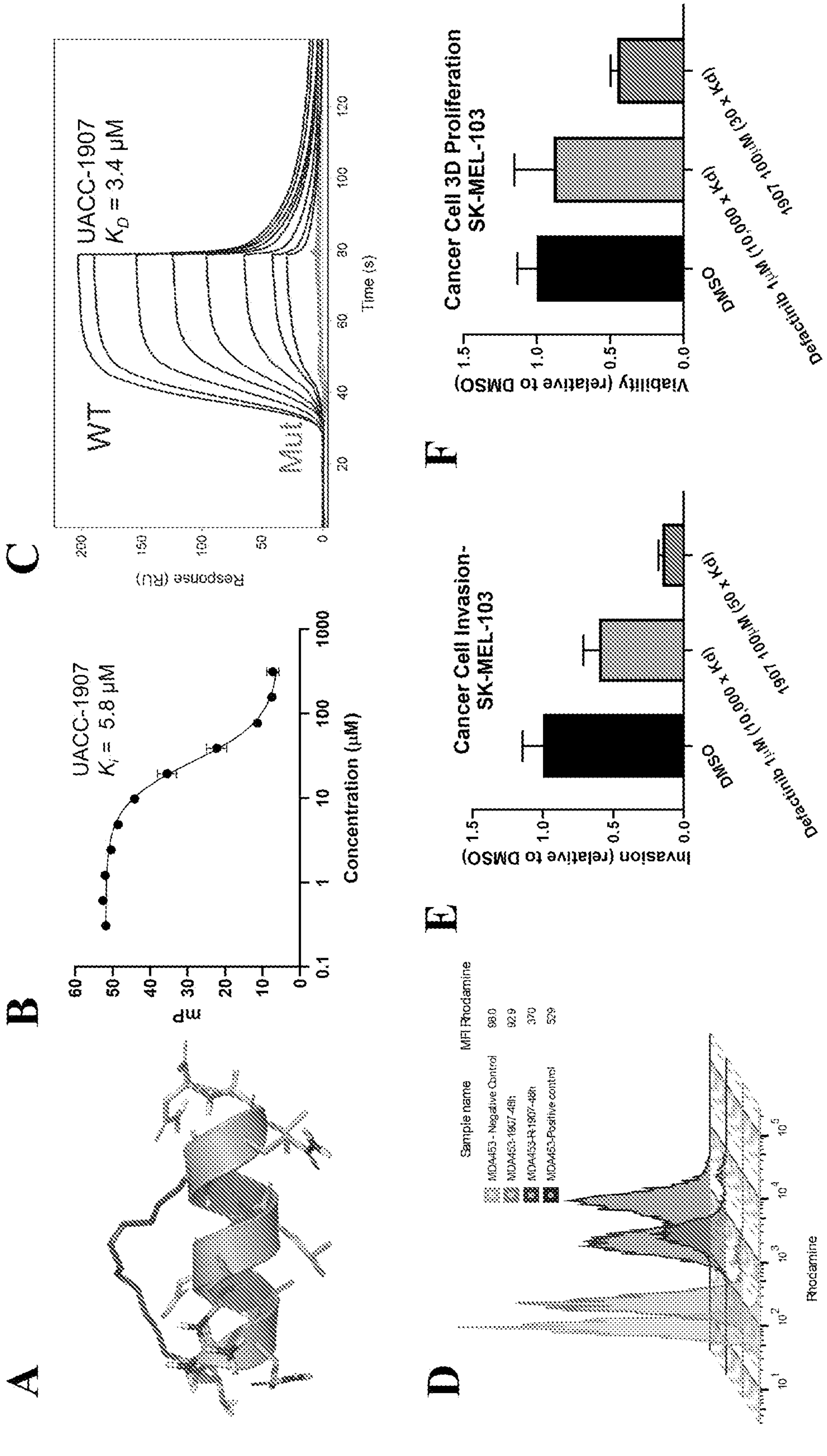
FIG. 4: Biochemical, biophysical, and cellular data of stapled peptide UACC-1907 (1907). A. 3D model of peptide 1907 with staple highlighted in red. B. Competition FP experiment with 1907 showing inhibition of TAMRA-LD2 binding to FAT. C. SPR binding and selectivity analysis using WT FAT and Mutant FAT (L994E, I936A) at the helix-protein interface. D. Flow cytometry analysis of Rhodamine-1907 (10 μM) cellular uptake in MDA-MB-453 breast cancer cells. E. Boyden-chamber invasion assays in SK-MEL-103 melanoma cells. F. 3D Matrigel-on-top proliferation assays in SK-MEL-103 melanoma cells.

There are three major approaches for hydrocarbon stapling of alpha helical peptides: (1) i, i+3, (2) i, i+4, and (3) i, i+7, each having the potential for different biological effects. Experiments were conducted that synthesized various iterations of these i motifs (staple scanning) at different positions (shifting N or C terminal), stapling at residues present at both the hydrophobic interface and solvent-accessible area. Experiments were conducted that extended residues on the N- and C-terminus of the peptide, as these amino acids can have a beneficial effect on both binding affinity and cell permeability. Finally, to enhance protein contacts, enhance permeability, and further inhibit recogni- was identified which gave a $K_D$ of 3.4 μM in SPR affinity analysis, showed very high selectivity for WT/mutant protein in SPR, and competitively inhibited paxillin-FAT binding in fluorescence polarization (FP) assays ($K_i$=5.8 μM) (FIG. 4). The activity of UACC-1907 was much improved compared to the native paxillin LD2 peptide UACC-1967 ($K_D$=156 μM, $K_i$=70.6 μM). The chemical structure of UACC-1907 (1907) is also shown in FIG. 3.

The specific staple position of 1907 was essential for biochemical/biophysical activity, as 1905, with the same i+7 stapling motif shifted just one amino acid away, had no binding and inhibitory properties. Other LD2 peptides with the same i+7 stapling motif in different positions (1914, 2017) also showed limited activity compared to 1907. LD2 peptides with different stapling motifs (1919—(i, i+4), 1921—(i, i+3), 2015—(i, i+4), 2022—(i, i+3), 2024—(i, i+3)) did not show much activity compared to 1907. Also, a peptide with the Aib (2-Aminoisobutyric acid)-based alpha-helical stabilization strategy, 1912, had lower activity compared to 1907. Amino acid sequence was also very important for activity, as 1910, with two glutamic acid to glutamine conversions, was not as active as 1907. Leucines 145, 149, and 152 (based off paxillin sequence) were very important for activity, as peptides with conversions to tryptophan (1933, 2007) had worse binding and inhibitory properties compared to 1907. Peptide 2014, with a L145E and L152E substitution, showed completely no binding and inhibitory properties. Overall, stapled peptides based off homologous protein sequences (1929, 1916) did not have comparable activity to LD2-derived 1907. Paxillin LD4-derived peptide 1917 had similar, albeit lower activity than LD2-derived 1907. The length of stapled peptide 1907 was also crucial for activity, as 2011, a truncated stapled peptide at the n- and c-terminus, had no binding and inhibitory properties. An extended peptide, 1920, had a modest binding affinity ($K_D$=7.0 μM), however worse inhibitory properties ($K_i$=25.0 μM) compared to 1907. These data showed that an empirically derived optimal stapling chemistry and amino acid sequence was required for best FAK binding and inhibition.

To further evaluate the activity of 1907, experiments were conducted that tested the peptide in a flow cytometry-based cell permeability assay. In this assay, Rhodamine-tagged 1907 successfully crossed the cell membrane in MDA-MB-453 breast cancer cells compared to Rhodamine only control (FIG. 4). Experiments were also conducted to test the cellular efficacy in SK-MEL-103 melanoma cells. Peptide 1907 effectively inhibited SK-MEL-103 invasion and 3D proliferation at a lower relative concentration (relative to compound $K_D$) compared to known FAK inhibitor Defactinib (FIG. 4).

Figure 5:
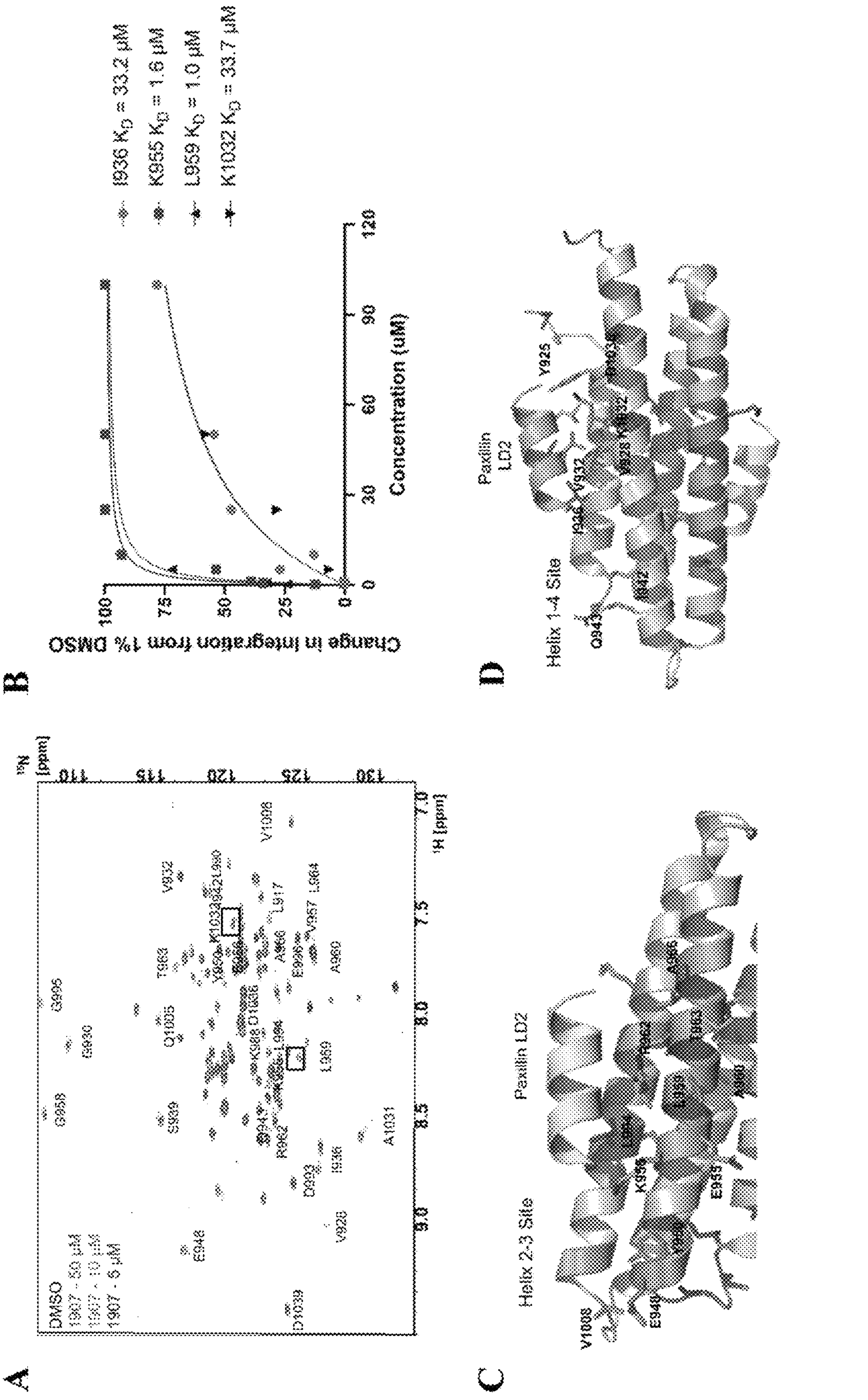
FIG. 5: HSQC NMR data of $^{15}N$ labeled FAT domain protein in complex with peptide 1907. A. $^{1}H/^{15}N$ HSQC spectra of the FAT domain with 1% DMSO (black), 50 μM 1907 (red), 10 μM 1907 (green), and 5 μM 1907 (blue) using a 600 MHz NMR spectrometer. Note: the peptide causes peak intensity changes at both the Helix 1-4 (K1032) and Helix 2-3 (L959) binding sites. B. 1907 binding curve using HSQC NMR and four different residues (V932, L959, L994, and D1036) on the FAT domain. 1907 concentration was titrated from 100-0.01 μM and percent change in peak integration was plotted vs concentration to calculate $K_D$. C. Mapping of key perturbations caused by 1907 at the Helix 2-3 site and D. Helix 1-4 site. Residues with large shifts are highlighted in green. Note, 1907 binds to the same site as native paxillin LD2 (yellow and cyan).
Figure 6:
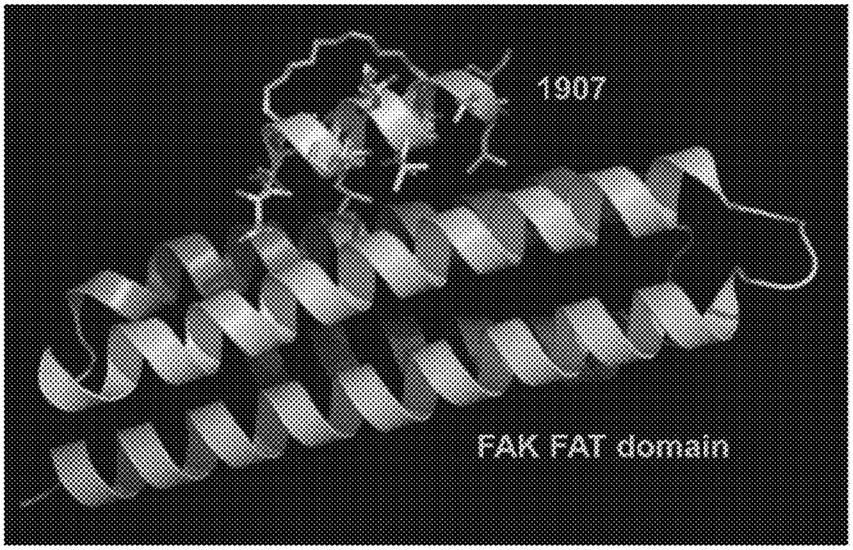
FIG. 6: X-ray crystal structure of FAK peptidic inhibitor, 1907, in complex with the human FAK FAT domain at 1.95 Å resolution. Left panel shows the stapled peptide in blue and FAT domain in green. Right panel shows the electron density map of the peptide in the binding pocket.
Figure 6:
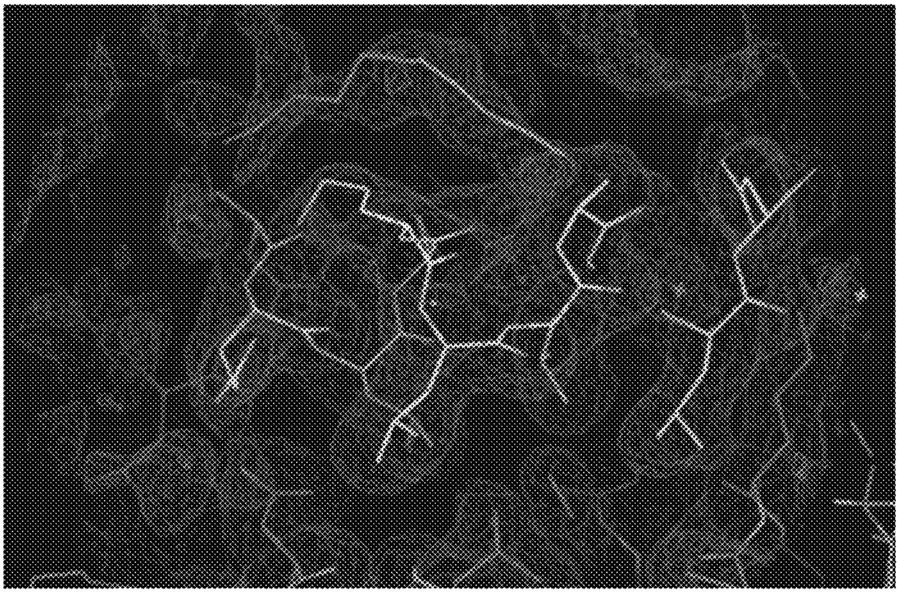

Further structural biology experiments were conducted to test 1907 for binding to the paxillin binding site of the FAK FAT domain. In HSQC NMR experiments with $^{15}N$ labeled FAT domain protein, 1907 showed specific binding at both the FAT Helix 2-3 ($L_{959}$, R962, K955) and FAT Helix 1-4 (V928, 1936) binding sites for the native paxillin LD2 peptide (FIG. 5). NMR-derived FAT binding affinities showed that 1907 had a stronger affinity for the FAT Helix 2-3 site (L959: $K_D$=1.0 μM, K955: $K_D$=1.6 μM) compared to the Helix 1-4 site (1936: $K_D$=33.2 μM, K1032: $K_D$=33.7 μM). Also, the X-ray co-crystal structure of 1907 in complex with the human FAK FAT domain was successfully determined (FIG. 6). In this crystal structure, 1907 was bound to the same FAT Helix 2-3 site as paxillin LD2 and showed prominent alpha helical structure. In all, these studies supported the feasibility of the stapled peptide approach and gave 1907 as a peptide lead for further chemical optimization.

Figure 7:
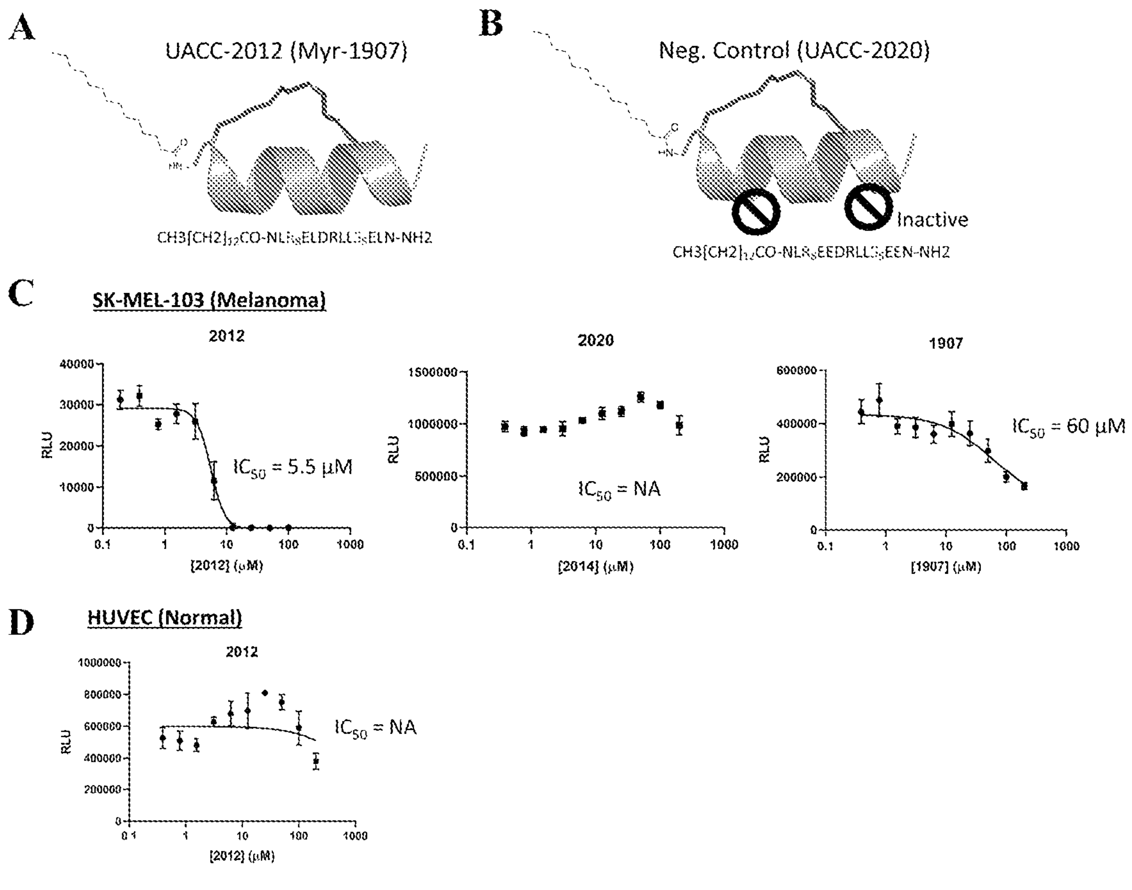
FIG. 7. Anti-cancer efficacy of myristoylated peptide 1907 (UACC-2012). A. 3D structure of UACC-2012. B. 3D structure of negative control molecule (UACC-2020). C. 3D Matrigel-on-top cell proliferation data of stapled peptides in SK-MEL-103 melanoma cells. D. 3D Matrigel-on-top cell proliferation of stapled peptide UACC-2012 in HUVEC "normal" cells.
Figure 14:
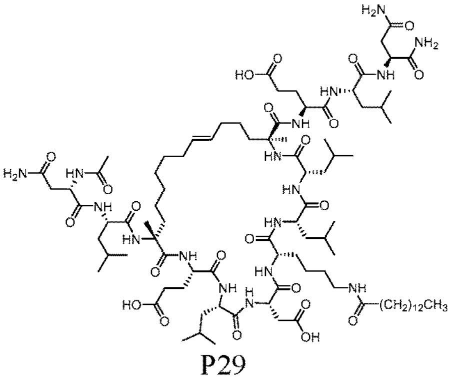
FIG. 14. Structures of compounds P29-P34, P37 and P38.
Figure 14:
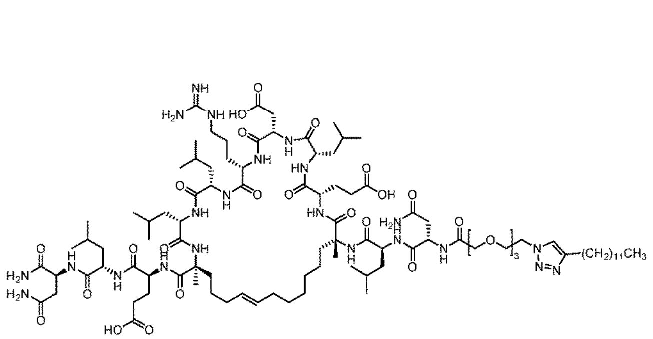
Figure 14:
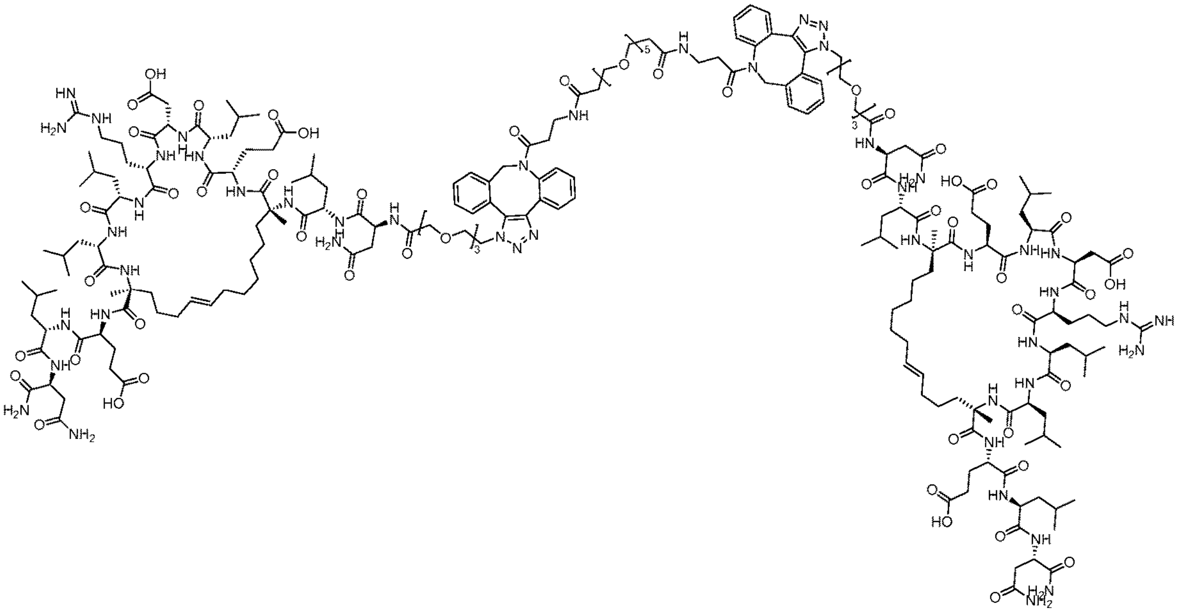
Figure 14:
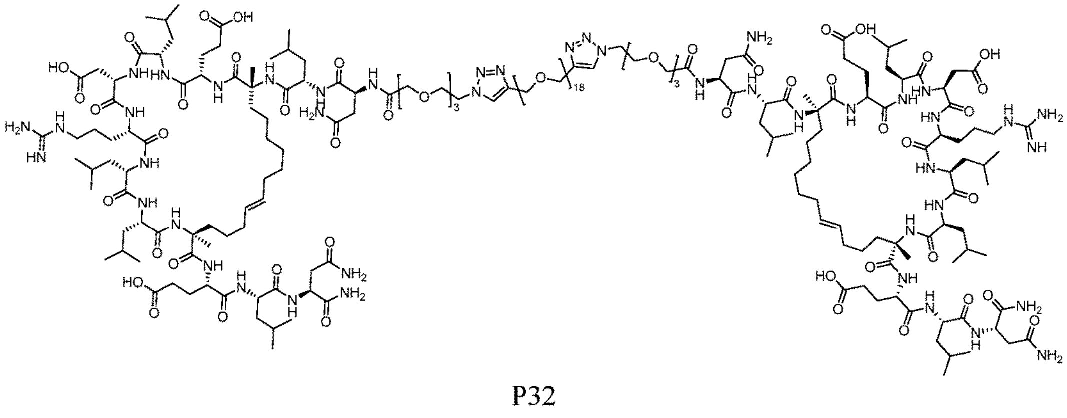
Figure 14:
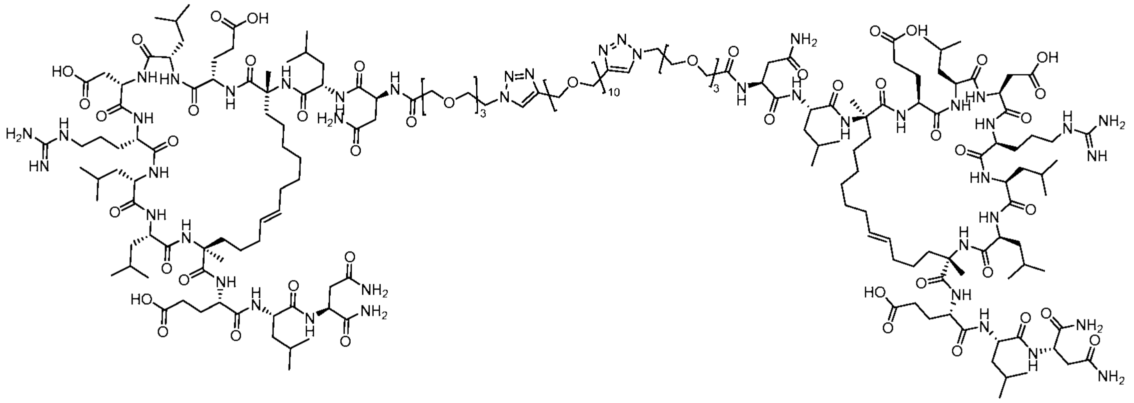
Figure 14:
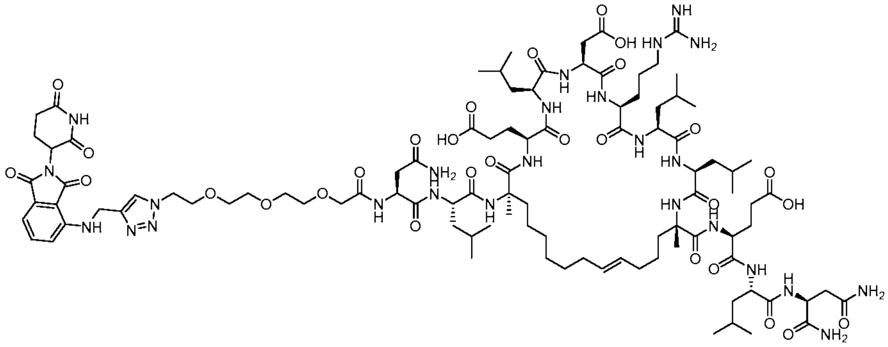
Figure 14:
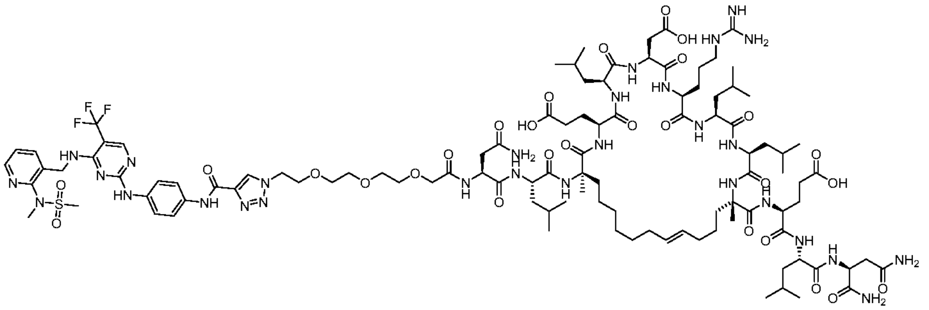
Figure 14:
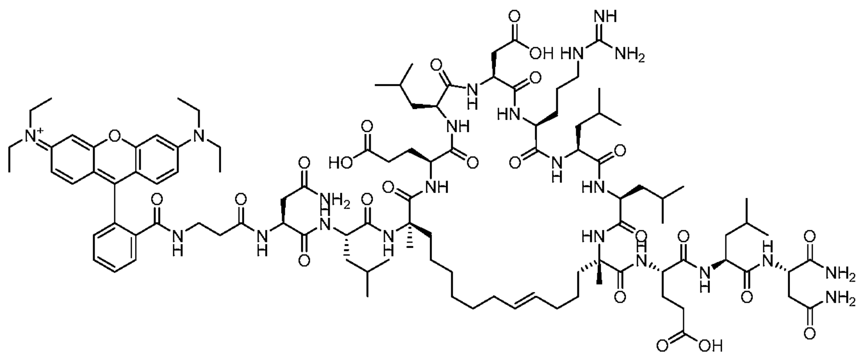

To improve the cellular potency of 1907, peptide analogs were designed and synthesized with a myristoyl (2012, 2029) or dodecyl (2025) modification for increased hydrophobicity and cellular uptake (FIG. 7, Table 2, FIG. 14). A negative control myristoylated peptide (2020) was designed and synthesized based on non-active molecule 2014. Experiments were conducted to test the efficacy of these peptides in 3D proliferation assays using SK-MEL-103 melanoma cells. Peptide 2012 ($IC_{50}$=5.5 μM) had an improved cellular potency compared to 1907 ($IC_{50}$=60 μM), while negative control 2020 had no effect ($IC_{50}$=NA). Furthermore, 2012 had no effects on the proliferation of normal HUVEC cells ($IC_{50}$=NA) (FIG. 7).

Figure 8:
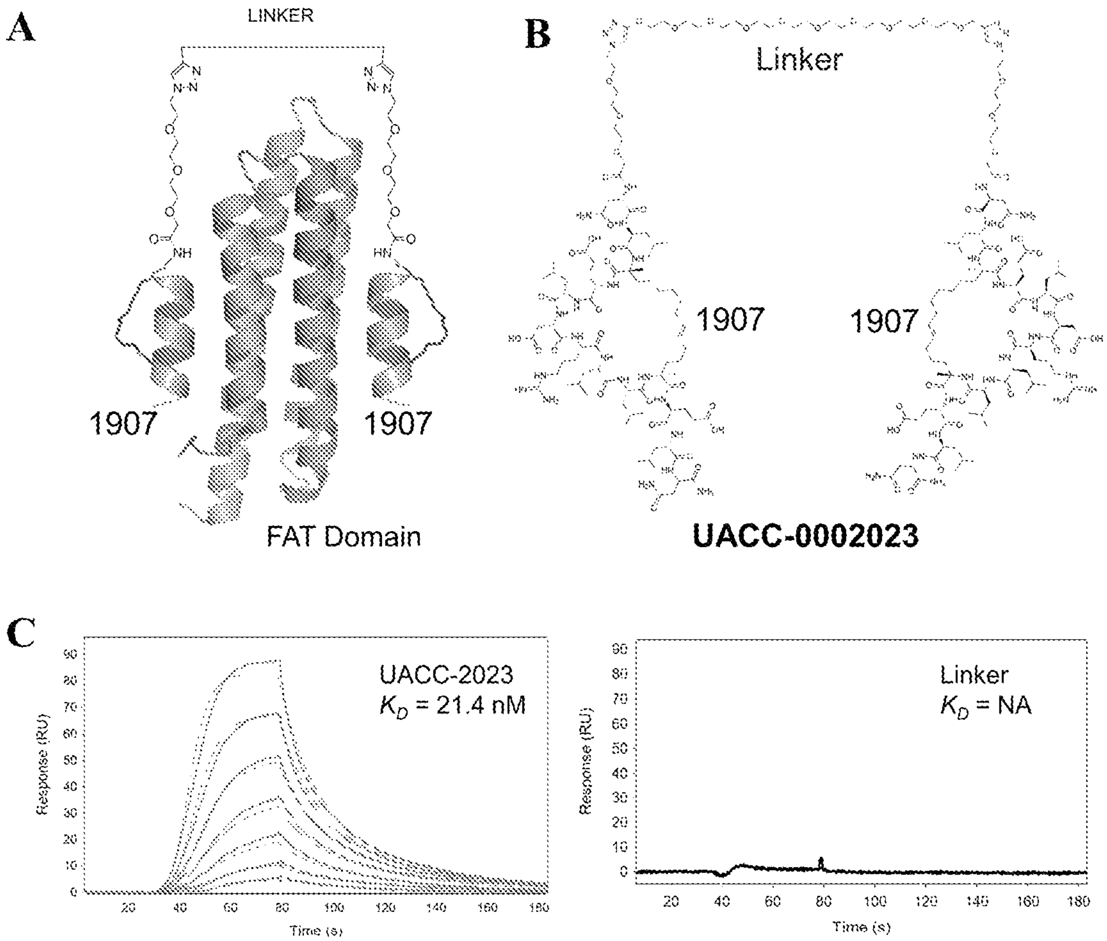
FIG. 8. FAT bivalent stapled peptide strategy and SPR data of synthesized peptide UACC-2023. A. Overview of bivalent stapled peptide strategy to enable FAT domain dual-site binding using click chemistry and linker approaches. B. Structure of UACC-2023. C. SPR sensograms of bivalent peptide UACC-2023 and $PEG_{10}$ linker binding to FAT.

As evidenced by SPR, mutagenesis, and NMR data, peptide 1907 has the ability to bind to both the Helix 2-3 and Helix 1-4 binding sites on the FAT domain. To create a multivalent peptide with the ability to bind both sites simultaneously and therefore with nanomolar binding affinity, we designed and synthesized a series of linked peptides (2018, 2021, 2023) via the coupling of two azido-modified 1907 molecules (2006) to a DBCO-$[PEG]_n$-DBCO or an alkyne-$[PEG]_n$-alkyne linker (Table 2, FIG. 8). The chemical structures of 2018, 2021, and 2023 are shown in FIG. 14. Synthesized azide-containing stapled peptide (2006) showed that the binding affinity to FAT was comparable to the parent peptide 1907 (4.6 vs 2.8 μM). Azide-alkyne cycloaddition or "click" chemistry was used to tether the multivalent peptides. Experiments were conducted to test the FAT binding affinity of multivalent peptides 2018, 2021, and 2023 (Table 2). The DBCO-based multivalent peptide 2018 had no gain in binding affinity ($K_D$=24.2 μM) compared to 1907, however alkyne-based peptides 2021 ($K_D$=237 nM) and 2023 ($K_D$=21 nM) had a drastic improvement in FAT binding affinity (FIG. 8). These data showed proof-of-principle for the FAT multivalent approach and highlighted the empirical determination of optimal linker length ($PEG_n$) and chemistry (DBCO vs alkyne) for maximum FAT binding.

Figure 9:
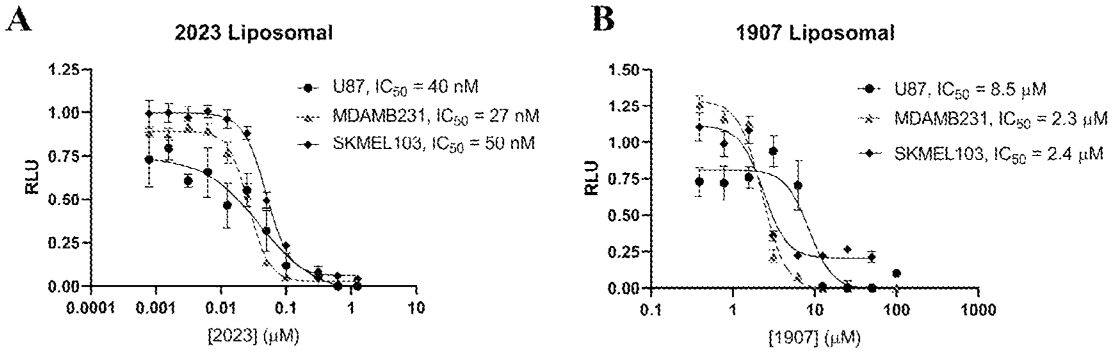
FIG. 9. Anti-cancer efficacy data of stapled peptides 2023 and 1907 in liposomal formulations. A. 2D proliferation data of peptide 2023 in combination with cationic lipid reagent Saint-Protein (Synvolux). B. 2D proliferation data of peptide 1907 in combination with cationic lipid reagent Saint-Protein. Lipid:peptide formulations were prepared as 10× stocks using a 1:1 (v:v) ratio in PBS PH 7.4+1% DMSO and titrating concentrations of peptide.

To facilitate membrane permeability of peptides 2023 and 1907, in vitro experiments were conducted with liposomal formulation Saint-Protein (Synvolux). A 3:1 volume:volume ratio of Saint:Peptide was used to prepare formulations and peptide concentration was titrated in PBS PH 7.4+1% DMSO. As shown in FIG. 9, the 2023 liposomal formulation displayed nanomolar effects on the proliferation of a variety of cancer cells (U87 $IC_{50}$=40 nM, MDAMB231 $IC_{50}$=27 nM, SKMEL103 $IC_{50}$=50 nM). The 1907 liposomal formulation showed low micromolar effects on cancer cell proliferation (U87 $IC_{50}$=8.5 μM, MDAMB231 $IC_{50}$=2.3 μM, SKMEL103 $IC_{50}$=2.4 μM). The calculated cellular IC50's for both 2023 and 1907 were in alignment with FAT domain $K_D$ values determined by SPR and NMR.

Figure 10:
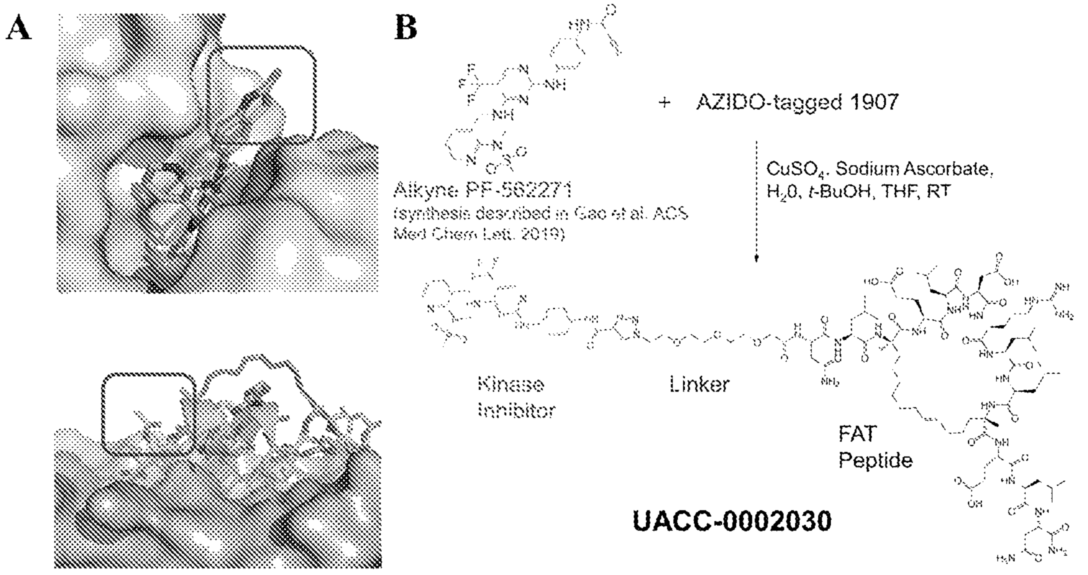
FIG. 10. Overview of synthetic strategy for FAT-Kinase bifunctional inhibitors and proof-of-concept molecule UACC-2030. A. (Upper) Site of attachment for FAK kinase domain inhibitor PF-562271. (Lower) Site of attachment for FAT domain inhibitor 1907. B. Synthesis plan for FAT-Kinase bifunctionals and chemical structure of synthesized molecule UACC-2030.

To create bifunctional peptides with the dual-ability to inhibit both the FAK FAT domain and the FAK kinase domain, we designed hybrid peptides based on FAT stapled peptide 1907 and FAK kinase domain inhibitor PF-562271 (PF-271) (FIG. 10). "Click" chemistry was utilized to link alkyne-derivatized PF-271 to azido-modified peptide 2006. Rational selection of 2006 as conjugation partner was determined by X-ray crystallography information and calculated biophysical data (Table 2 & FIG. 6). Site of alkyne functionalization on PF-271 was selected based on prior X-ray co-crystal structures of PF-271:FAK kinase and demonstrated feasibility for PROTAC approaches (40). Successful synthesis of FAT-Kinase bifunctional (UACC-2030) is shown in Table 3. Chemical structure of 2030 is shown in FIG. 10 and FIG. 14.

Figure 11:
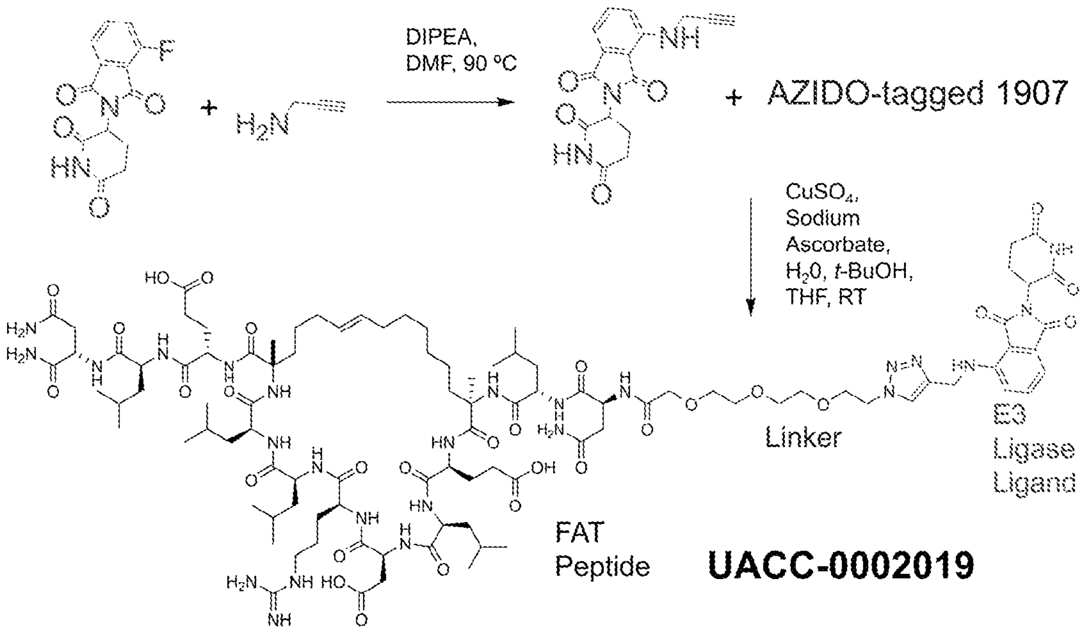
FIG. 11. Overview of FAT-PROTAC synthetic strategy and proof-of-concept synthesized molecule UACC-2019.

To create FAT peptides with the ability to degrade FAK protein in cells through the PROteoylsis TArgeting Chimera (PROTAC) approach, we designed hybrid peptides based on FAT stapled peptide 1907 and E3-ligase targeting ligand thalidomide (FIG. 11). "Click" chemistry was utilized to link alkyne-derivatized thalidomide to azido-modified peptide 2006. Rational selection of 2006 as conjugation partner was determined by X-ray crystallography information and calculated biophysical data (Table 2 & FIG. 6). Successful synthesis of FAT-PROTAC molecule (UACC-2019) is shown in Table 3. Chemical structure of 2019 is shown in FIG. 11 and FIG. 14. Peptide 2019 ($K_D$=10.2 μM) showed FAT domain binding affinity comparable to parent structure 1907 (Table 2).

Figure 12:
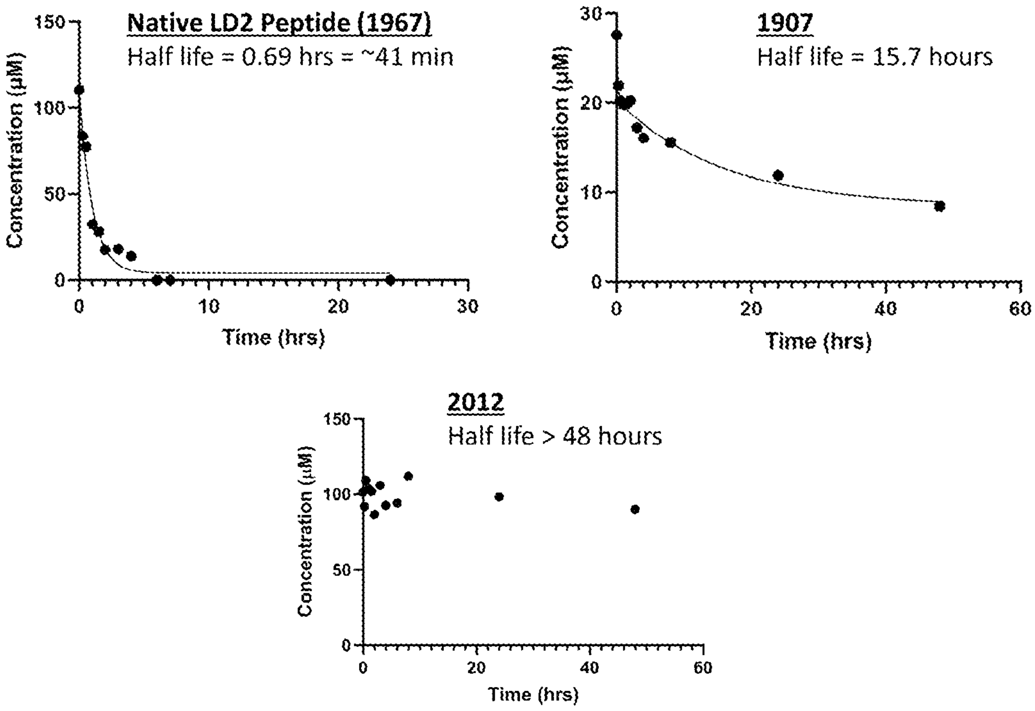
FIG. 12. In vitro trypsin digest assays to measure peptide (1967, 1907, and 2012) stability and protease resistance. Assays were performed using trypsin-agarose beads (ThermoFisher) and measurement of peptide concentration using LC-MS. Peptide half-lives were calculated using GraphPad Prism software.

Experiments were conducted to test the protease resistance of synthesized peptides 1967 (native LD2), 1907, and 2012 (FIG. 12). Trypsin-agarose beads were used to test the potential cleavage of peptides in a physiological buffer and LC-MS was used as the analytical method to determine peptide concentration. As shown in FIG. 12, both stapled peptides 1907 ($t_{1/2}$=15.7 h) and 2012 ($t_{1/2}$>48 h) showed greatly improved stability and protease resistance compared to native LD2 peptide 1967 ($t_{1/2}$=0.69 h).

Figure 13:
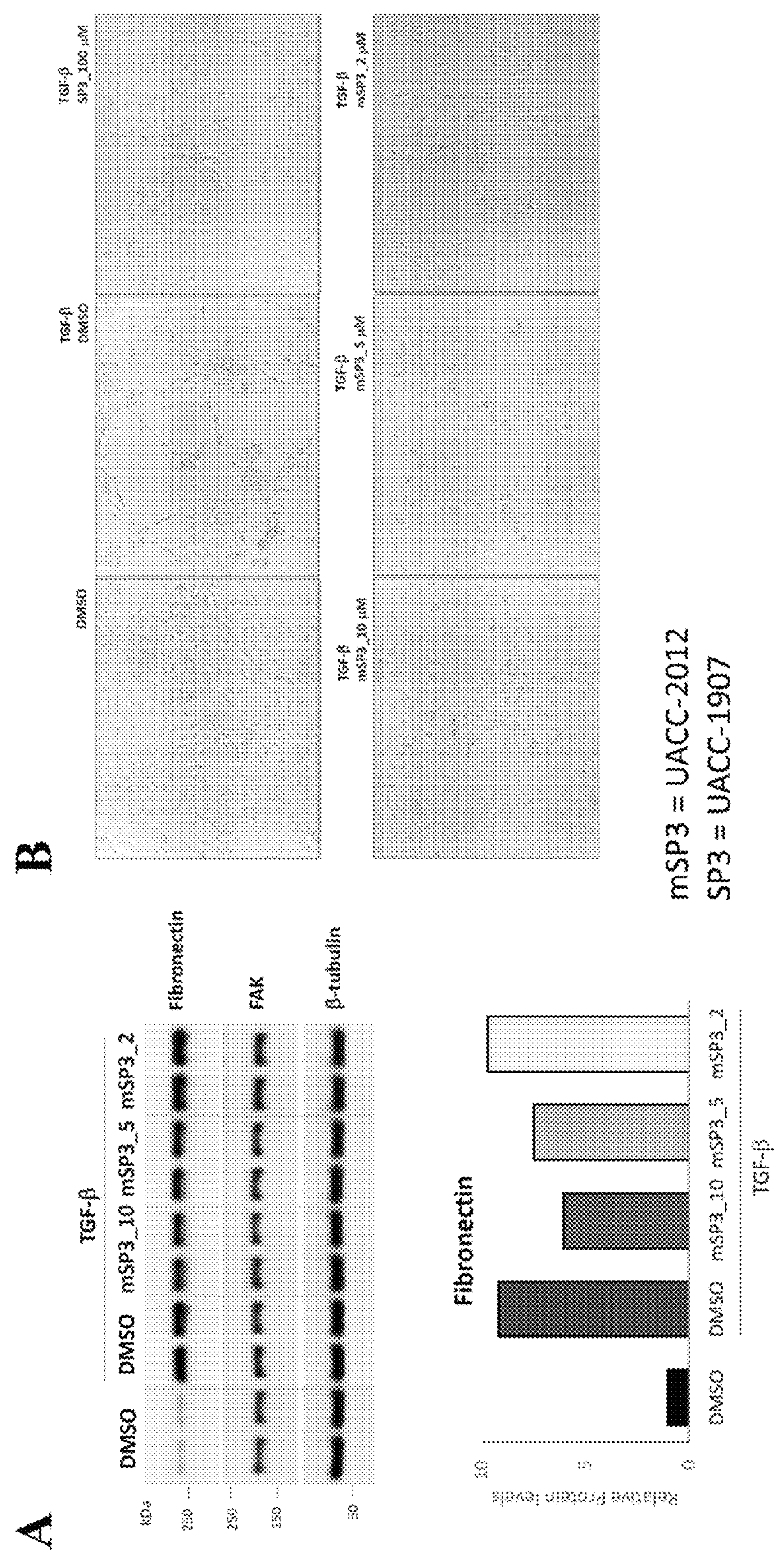
FIG. 13. Anti-fibrotic activity of FAT stapled peptide UACC-2012 in LX2 human liver stellate cells. A. Western blot studies of LX2 cells treated with 2 ng/mL TGF-β for 17 h to induce pro-fibrotic phenotypes. Cells were pretreated for 1 h with either DMSO or UACC-2012 (mSP3) at 10 μM, 5 μM, and 2 μM. Quantification of fibronectin results are shown in the lower panel. B. Morphological changes of LX2 cells after TGF-β and peptide treatment for 17 h. Images were captured using bright field microscopy. Abbreviations: mSP3=UACC-2012; SP3=UACC-1907.

Experiments were conducted to test the anti-fibrotic effects of stapled peptides targeting the FAK FAT domain (FIG. 13). TGF-β induction was performed in LX-2 human liver stellate cells to promote a pro-fibrotic phenotypic and differentiation to myofibroblast-like cells. 2012 treatment reduced the TGF-β-induced expression of fibronectin, a marker of fibrosis, in a dose-dependent manner. Also, 2012 treatment induced a morphological change in TGF-β-induced LX-2 cells, causing a de-differentiation of cells and reversion of the phenotype.

Additional stapled peptides were generated. Table 2 provides additional stapled peptides with sequence/structural information, SPR and FP results.

TABLE 2

Stapled Peptide SAR Analysis.

| SEQ ID NO: | Name | Sequence | SPR $K_d$ (μM) | FP $K_i$ (μM) |
|---|---|---|---|---|
| 1 | 1967 | Ac-NLSELDRLLLELN-NH$_2$ (Ac-LD$_2$-NH$_2$) | 156 | 70.6 |
| 2 | 1905 | Ac-NLSR$_8$LDRLLLS$_5$LN-NH$_2$ | >200 | >1250 |
| 3 | 1906 | H-NLSR$_5$LDRLLNS$_5$LN-NH$_2$ | >200 | >1250 |
| 4 | 1907 | Ac-NLR$_8$ELDRLLS$_5$ELN-NH$_2$ | 3.43 | 5.80 |
| 5 | 1910 | Ac-NLR$_8$QLDRLLS$_5$QLN-NH$_2$ | 24.8 | 46.8 |
| 6 | 1912 | Ac-NLAibELDRLLAibELN-NH$_2$ | 38.7 | 28.1 |
| 7 | 1913 | Ac-DLR$_8$ELDRLLS$_5$ELD-NH$_2$ | 13.7 | 21.8 |
| 8 | 1914 | Ac-NLSER$_8$DRLLLES$_5$N-NH$_2$ | 64.3 | >1250 |
| 9 | 1919 | Ac-NLSES$_5$DRLS$_5$LELN-NH$_2$ | 68.9 | 38.6 |
| 10 | 1920 | Ac-SLGSNLR$_8$ELDRLLS$_5$ELNAVQH-NH$_2$ | 6.95 | 25.0 |
| 11 | 1921 | Ac-NLSELDRLR$_5$LES$_5$N-NH$_2$ | >200 | 492 |
| 12 | 1925 | Ac-NLSER$_8$DRAALES$_5$N-NH$_2$ | >200 | 492 |
| 13 | 1929 | Ac-RRR$_8$ARLRFMS$_5$QFY-NH$_2$ | 77.6 | >1250 |
| 14 | 1931 | Ac-NLRES$_5$DRLS$_5$RELN-NH$_2$ | 13.7 | 14.5 |
| 15 | 1933 | Ac-NLR$_8$EWDRLLS$_5$EWN-NH$_2$ | 155 | 281 |
| 16 | 2007 | Ac-NLR$_8$ELDRLWS$_5$ELN-NH$_2$ | 73.1 | 190 |
| 17 | 2009 | Ac-NLR$_8$ALDRLLS$_5$ELN-NH$_2$ | 6.96 | 26.7 |
| 18 | 2010 | Ac-NLR$_8$ALDALLS$_5$ELN-NH$_2$ | 12.6 | 68.5 |
| 19 | 2011 | Ac-R$_8$ELDRLLS$_5$-NH$_2$ | >200 | >333 |
| 20 | 2013 | Ac-NLR$_8$ELDRLLS$_5$ELN-NH$_2$ (unstapled) | 37.2 | 20.3 |
| 21 | 2014 | Ac-NLR$_8$EEDRLLS$_5$EEN-NH$_2$ | >200 | >1250 |
| 22 | 2015 | Ac-NLSELDRS$_5$LLES$_5$N-NH$_2$ | 47.5 | 114 |
| 23 | 2017 | Ac-NR$_8$SELDRLS$_5$LELN-NH$_2$ | 20.3 | 80.6 |
| 24 | 2022 | Ac-NLSER$_5$DRS$_5$LLELN-NH$_2$ | 911 | 341 |
| 25 | 2024 | Ac-NR$_5$SES$_5$DRLLLELN-NH$_2$ | >200 | 412 |
| 26 | 2028 | Ac-NLR$_8$ELDKLLS$_5$ELN-NH$_2$ | 1.36 (1) 10.9 (2)* | NC |
| 27 | 2006 | N$_3$(CH$_2$CH$_2$O)$_3$CH$_2$CO-NLR$_8$ELDRLLS$_5$ELN-NH$_2$ (Az-1907) | 4.58 | 51.4 |
| 28 | 2012 | Myristoyl-NLR$_8$ELDRLLS$_5$ELN-NH$_2$ | >200 | 83.0 |
| 29 | 2020 | Myristoyl-NLR$_8$EEDRLLS$_5$EEN-NH$_2$ | >200 | >1250 |
| 30 | 2029 | Ac-NLR$_8$ELDK(myristoyl)LLS$_5$ELN-NH$_2$ | 19.5 | NC |
| 31 | 2025 | 4-Dodecyl-(Az-1907) | 190 | 257 |
| 32 | 2018 | (Az-1907)-[DBCO-PEG-DBCO]-(Az-1907) | 24.2 | 51.3 |
| 33 | 2021 | (Az-1907)-PEG18-(Az-1907) | 0.237 | NA |
| 34 | 2023 | (Az-1907)-PEG10-(Az-1907) | 0.0214 | NA |
| 35 | 2019 | Thalidomide-(Az-1907) | 10.2 | 29.1 |
| 36 | 1916 | Ac-SATR$_8$ELDELMS$_5$SLSD-NH$_2$ | 32.3 | 47.5 |
| 37 | 1917 | Ac-SATRES$_5$DELS$_5$ASLSD-NH$_2$ | 4.90 | 6.72 |

Synthesized hydrocarbon stapled peptides were varied based on staple strategy ((i, i + 3); (i, i + 4); and (i, i + 7)), staple position, sequence length, amino acid composition, and homologous sequences. MW, SPR data, and FP data are shown.

Note:

1907 and 2023 were identified as top candidates based on data.

Abbreviations: R$_8$: (R)-2-(7-octenyl)alanine; S$_5$: (S)-2-(4-pentenyl)alanine; R$_5$: (R)-2-(4-pentenyl)alanine; Az: 2-(2-(2-(2-azidoethoxy)ethoxy)ethoxy)acetyl; Aib: 2-aminoisobutyric acid; DBCO: 3-amino-1-(2-azatricyclo[10.4.0.0$^{4,9}$]hexadeca-1(16),4,6,8,12,14-hexaen-10-yn-2-yl)propan-1-one;

*two-site binding model; NC: not yet calculated; NA: Not applicable due to $K_i$ outside range of assay; or derivatives thereof. Unless otherwise stated, the peptides are the product(s) of an intramolecular ring-closing methasis reaction; double bond geometry has not been established or quantified. These sequences are abbreviated and may refer to "click" chemistry products. FIG. 14 shows the structures of peptides P29-P34.

Example II

This example describes the materials and methods for Example I.

Synthesis

The compounds described herein were synthesized using Rink amide resin and various combinations of Fmoc-(S)-2-(4-pentenyl)alanine, Fmoc-(R)-2-(4-pentenyl)alanine, Fmoc-(R)-2-(7-octenyl)alanine, N-α-Fmoc-α-aminoisobutyric acid (Fmoc-Aib-OH), Na-Fmoc-Nε-(azido-PEG4)-L-Lysine, Fmoc-Ala-OH, Fmoc-Arg(Pbf)-OH, Fmoc-Asn (Trt)-OH, Fmoc-Asp(Ot-Bu)-OH, Fmoc-Gln(Trt)-OH, Fmoc-Glu(Ot-Bu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(t-Bu)-OH, Fmoc-Thr(t-Bu)-OH, Fmoc-Tyr(t-Bu)-OH, and Fmoc-Val-OH. Except for glycine, or as otherwise noted, these amino acids are in the "L" configuration. Standard Fmoc-based solid phase peptide synthesis chemistry, as known by those skilled in the art, was employed. Peptides were synthesized on a Biotage Initiator+Alstra automated microwave-assisted peptide synthesizer using Rink amide MBHA ChemMatrix resin (typical loading of 0.45 meq/g). N-Fmoc-protected amino acids were used with standard side chain protecting groups. The alkenyl amino acids Fmoc-(R)-2-(7-octenyl)alanine, Fmoc-(S)-2-(4-pentenyl)alanine and Fmoc-(R)-2-(4-pentenyl)alanine were purchased from Advanced ChemTech. Reactions were carried out on a 0.1 mmol scale. Typical conditions follow. Concentrations of 0.5 M for the protected amino acids, HCTU, DIC and Oxyma Pure; 1.0 M for DIPEA and 5.0 M for acetic anhydride in DMF were used. To ensure efficient mixing, reaction volumes of 4 mL were used and DMF was added as needed. A solution of 20% 4-methylpiperidine in DMF was used for Fmoc-deprotection and cleavage/global deprotection was effected using 95:2.5:2.5 (v/v) FA:water:triisopropylsilane. Couplings used 5 eq of amino acid, 5 eq of HCTU and 10 eq of DIPEA except in the cases where the unnatural alkene amino acids were used, where 3:3:6 mole equivalents of amino acid:HCTU:DIPEA were used.

The resin, provided as the free amine, was first swelled with DMF (70° C. for 20 min). The Fmoc-protected amino acid was coupled at 75° C. for 4 min, then washed with DMF. Double couplings were used for all residues. Arginine was coupled at 50° C. for 6 minutes. A cycle of Fmoc-deprotection followed which consisted of a 3 min reaction, then a 10 min reaction with fresh reagent, at ambient temperature, followed by a DMF wash. Double Fmoc-deprotection cycles were used for N-terminal residues and olefinic amino acids.

Ring closing metathesis was performed on-machine in a manual injection mode on the Fmoc-protected peptide, using Grubbs' first-generation catalyst (benzylidene-bis(tricyclohexylphosphine)dichlororuthenium). Prior to the reaction, the resin was washed well with cycles of DCM followed by $Et_2O$, dried briefly in vacuo, then washed and swelled with DCE. Grubbs' I (10 mM) was added then reacted at 40° C. for 1 h, with venting every 15 min. This was performed a total of three times, with DCE used to wash between reactions. Upon completion, the resin was washed with DCE then DCM, then swelled with DMF.

The Fmoc group was deprotected as above. When N-capped as the acetamide, 50 eq of acetic anhydride and 10 eq of DIPEA were used, and this reacted at ambient temperature for 45 min. Rhodamine B was coupled with 5 eq each of DIC and Oxyma Pure, at 75° C. for 4 min. The resin was washed with three cycles of DCM followed by Et2O, then dried in vacuo.

Cleavage using 95:2.5:2.5 TFA:water:triisopropylsilane was performed for 2 h at ambient temperature. The reaction solution was then added dropwise to 35 mL of cold Et2O. This was mixed, chilled at −80° C. for 30 min, then centrifuged at 6000×G for 6 min. After decanting the supernatant, the pellet was suspended in 20 mL of Et20, then chilled, centrifuged and decanted as above. The crude peptide was dried in vacuo. Preparative HPLC was performed on an Agilent 1260 II quaternary HPLC, with a Variable Wavelength detector, using a Zorbax SB-C18 column (Agilent 880975-202; 9.4×250 mm; 80 Å pore size; 5 m particle size) using a gradient of acetonitrile (0.1% AcOH) in water (0.1% AcOH).

Analytical HPLC was performed on an Agilent 1200 HPLC, with 1200 DAD and Infinity 6125 LCMSD detectors, using a Zorbax SB-C18 column (Agilent 830990-902; 2.1×150 mm; 80 Å pore size; 3.5 m particle size) using a gradient of acetonitrile (0.1% AcOH) in water (0.1% AcOH).

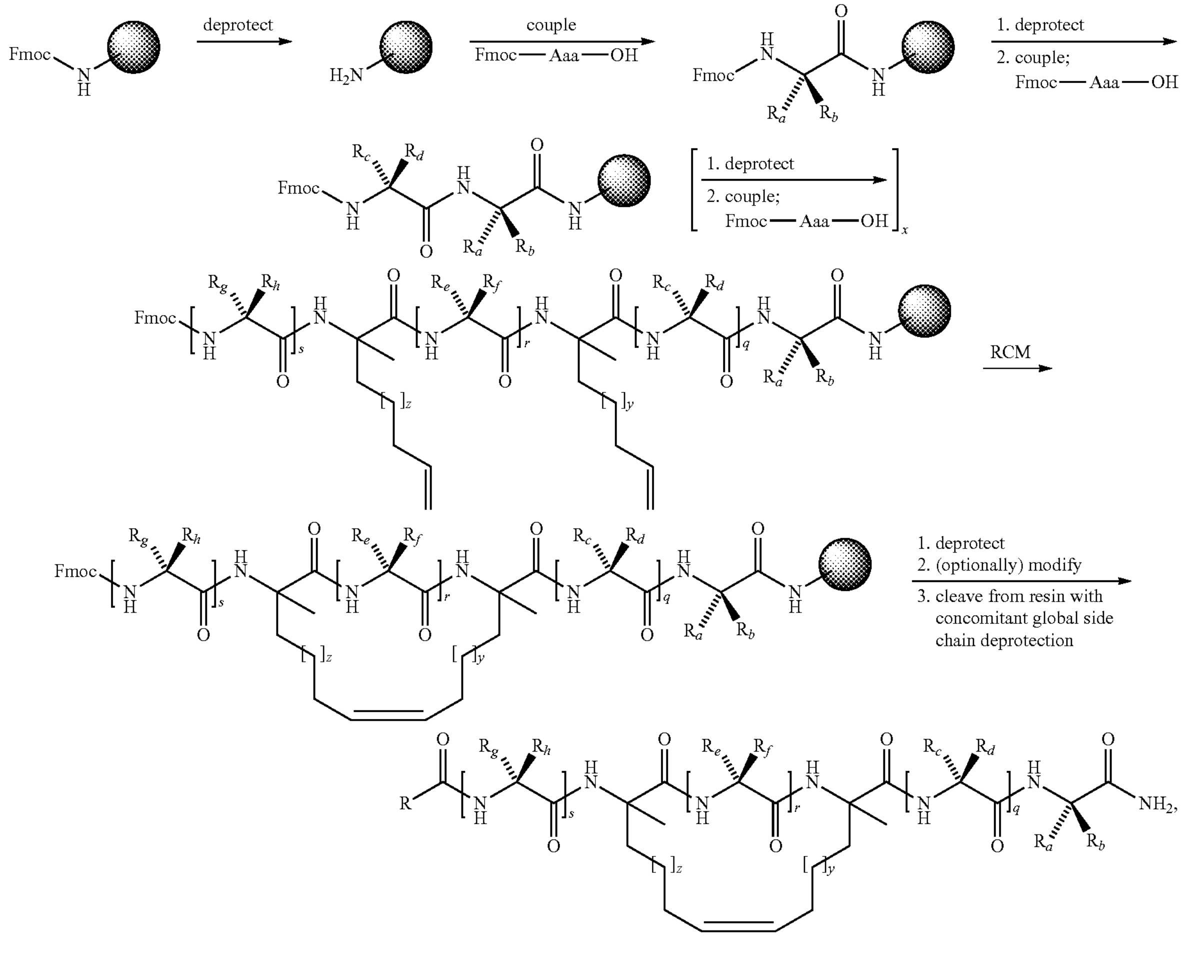

-continued

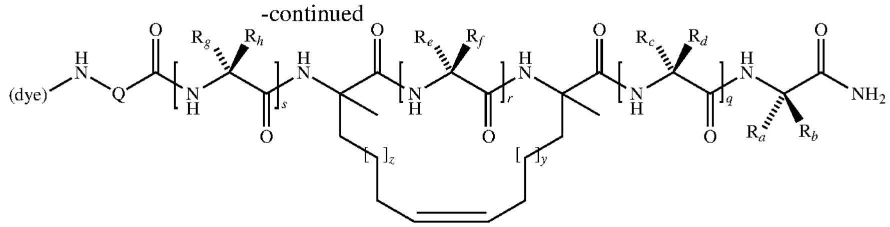

Surface Plasmon Resonance (SPR)

SPR binding studies were performed on a ForteBio Pioneer FE SPR system. In brief, a SADH Streptavidin in Dextran Hydrogel biosensor (ForteBio) was docked onto the flow cell and preconditioned with two injections of 10 mM NaOH, 1 M NaCl for 1 min at 50 μL/min. Subsequently, biotinylated Avitag-FAT protein was diluted in running buffer (100 mM Tris-HCl, 200 mM NaCl, 0.05% Tween-20) and injected at 10 μL/min to achieve approximately 1,000 RU of immobilized protein on channel 1. Empty channel 2 served as the reference control. After achieving a stable baseline, a concentration series (200 μM-0.01 μM) of peptide was prepared in final running buffer (100 mM Tris-HCl, 200 mM NaCl, 0.05% Tween-20, 5% DMSO) and injected using the OneStep gradient injection method at a flow rate of 75 μL/min. 3% sucrose was utilized as a bulk standard control for OneStep injection and a DMSO calibration curve was performed using a concentration range of 3.5% to 6.5% DMSO. Raw SPR data were appropriately processed in Qdat software (ForteBio) by normalizing the baseline prior to injection, aligning the channels, subtraction of the reference channel, and blank subtraction. Kinetic data were fitted to a pseudo-first order 1:1 interaction binding model using to calculate $K_D$. In addition, a steady-state model and Req data points were used to validate the binding affinity. Visual inspection of the SPR sensograms was performed to verify appropriate model fitting, lack of mass transport effects, return to baseline, and lack of irregular kinetics.

Fluorescence Polarization Assay

The FP assay buffer used was 20 mM Tris, 200 mM NaCl, 0.05% β-me, 0.1% Triton X-100, 5% glycerol, and 1× Halt protease inhibitor cocktail. All final FP reactions were placed into a 384-well plate (NUNC 267461) at 30 μL and shaken for 3 hours at room temperature to reach equilibrium. The plates were read on a PerkinElmer EnVision plate reader with software Envision Manager 1.13. Bodipy TMR FP optical module (2100-4100) was used as the mirror. The excitation filter (2100-5830) utilized wavelength at 531 nm and both emission filters (2100-5800 and 2100-5810) were at wavelengths of 579 nm. The baseline mP of TAMRA-LD2-L10D only was set to 15 mP through the assay optimization wizard on the Envision Manager software. The assay optimization set the measurement height to 6.5 mm, excitation light to 100%, G-factor to 1.01, detector gain to 300, and the number of flashes per well at 25.

For $IC_{50}$ determination of peptide inhibitors, inhibitor was titrated from 325 nM to 667 μM into FP Buffer containing 20 μM FAT and 0.1 μM TAMRA-LD2. Wells with no FAT were used as a baseline value which was subtracted from the raw values to produce ΔmP values. The plate was read at every hour for four hours to test for time differences in $IC_{50}$. The titration data was processed through GraphPad Prism to produce a dose response curve and a calculated $IC_{50}$ with standard error (SE). A four-parameter dose-response inhibition model was utilized and the bottom fit was constrained to the lower plateau of the curve. $K_i$ was determined from the following calculation:

$$K_i = \frac{I_{50}}{\frac{L_{50}}{K_D} + \frac{P_0}{K_D} + 1} \quad \text{(Eq. 1)}$$

where $I_{50}$ is the concentration of free inhibitor at 50% inhibition. $L_{50}$ is the concentration of free ligand at 50% inhibition. $P_0$ is the concentration of free protein and $K_D$ is calculated from the saturation curve. $I_{50}$ is calculated by the following equation:

$$I_{50} = IC_{50} - P_T + PL_{50}\left(\frac{K_D}{L_{50}} + 1\right) \quad \text{(Eq. 2)}$$

where $P_T$ is the total protein concentration, $L_T$ is the total labeled-ligand concentration, $P_0$ is the positive root of $P_0^2 + (K_D + L_T)*P_0 - P_T$, $PL_0 = P - P_0$, $PL_{50} = PL_0/2$, $L_0 = L_T - PL_0$, and $L_{50} = L_T - PL_{50}$.

2D HSOC NMR

2D HSQC-NMR samples were prepared at a $^{15}N$ FAT concentration of 100 μM. Peptides were screened at a concentration of 500 μM to 250 nM with a DMSO concentration of 5%. TROSY-based HSQC were collected on a Bruker Avance III-HD console equipped with a 5 mm TCI Prodigy cryoprobe operating at Larmor frequencies of 600.133 and 60.817 MHz for 1H and 15N respectively. Each 2D experiment was collected with sweep widths of 14.03 and 30.0 ppm, 2048 and 256 points respectively, and 16 signal averages [29-33]. All final data was processed through Bruker TopSpin. Chemical shift perturbations (CSPs) were mapped onto the structure of the FAT-LD2 complex (PDB 1OW8) using PyMOL software to examine the binding site and structural changes upon binding.

Flow Cytometry

Flow cytometry assays performed on the Canto II flow cytometer (BD Biosciences) were utilized to measure cellular uptake of TAMRA-tagged peptides. In brief, the instrument was properly gated using cells treated with TAMRA-only as a positive control. Also, cells treated with untagged peptide were used as a negative control to rule out non-specific signal. Cells were treated with TAMRA-tagged peptides for a duration of 2 h-48 h to measure cellular uptake. Permeability of peptide was reported as % positivity relative to TAMRA positive control and mean fluorescence intensity (MFI).

Immunofluorescence

Immunofluorescent staining was performed to measure the effect of stapled peptide on FAK localization. In brief, cells were seeded onto a coverslip and were fixed in 4% paraformaldehyde in 1×PBS PH 7.4 for 10 min and permeabilized with 0.2% Triton X-100 for 5 min on ice. Cells were blocked with 25% normal goat serum in 1×PBS PH 7.4 for 30 min, washed with 1×PBS PH 7.4, and incubated with primary FAK 4.47 antibody (Millipore) diluted 1:200 in 25% goat serum in 1×PBS PH 7.4. Cells were washed three times with 1×PBS PH 7.4, and a FITC-conjugated secondary antibody (1:400 dilution in 25% goat serum) was applied to the coverslip. Cells were imaged using a Zeiss AXIO Imager M2 Upright Widefield Fluorescent Microscope. Over six fields of view were captured per sample.

X-Ray Crystallography

Co-crystallization of lead peptide SP3 with the human FAK FAT domain (AA 919-1052), in which peptide was mixed and incubated with protein (1:1 molar ratio) prior to crystallization, was performed using a Rigaku Phoenix-HT crystallization robot using commercially available crystallization kits (Hampton Research, Molecular Dimensions, Qiagen) and focused buffer plates around the initial crystallization condition (altering pH, salt, glycerol, and other precipitants). Data collection was performed at synchrotron radiation sources such as the Advanced Photon Source (APS) at the Argonne National Laboratory (Chicago, IL), and the Advanced Light Source (ALS) at the Lawrence Berkeley National Laboratory (Berkeley, California). Structural determination was done by molecular replacement using the crystallographic structure PDB 1K05 as a reference model. Extra electron density in FAK-FAT domain binding pockets (Fo-Fc) was modeled to peptide structures and progressively refined over multiple cycles to build a high quality model.

Table 3 provides mass spectrometry data for peptide inhibitors of the present invention.

TABLE 3

Mass Spectrometry Data for Peptide Inhibitors. Mass spectra were by ESI+.

| SEQ ID NO: | Name | Exact mass | Observed mass | Calc mass | Assignment |
|---|---|---|---|---|---|
| 1 | 1967 | 1581.87 | 792.1 | 791.9 | /½/*[M + 2H]$^{2+}$ |
| 2 | 1905 | 1616.00 | 809.1 | 809.0 | /½/*[M + 2H]$^{2+}$ |
| 3 | 1906 | 1574.95 | 788.6 | 788.5 | /½/*[M + 2H]$^{2+}$ |
| 4 | 1907 | 1673.97 | 838.1 | 838.0 | /½/*[M + 2H]$^{2+}$ |
| 5 | 1910 | 1672.00 | 837.1 | 837.0 | /½/*[M + 2H]$^{2+}$ |
| 6 | 1912 | 1551.86 | 777.1 | 776.9 | /½/*[M + 2H]$^{2+}$ |
| 7 | 1913 | 1675.94 | 839.5 | 839.0 | ½*[M + 2H]$^{2+}$ |
| 8 | 1914 | 1647.92 | 825.1 | 825.0 | ½*[M + 2H]$^{2+}$ |
| 9 | 1919 | 1605.87 | 804.0 | 803.9 | ½*[M + 2H]$^{2+}$ |
| 10 | 1920 | 2453.36 | 1227.9 | 1227.7 | ½*[M + 2H]$^{2+}$ |
| 11 | 1921 | 1605.87 | 804.0 | 803.9 | ½*[M + 2H]$^{2+}$ |
| 12 | 1925 | 1563.83 | 783.0 | 782.9 | ½*[M + 2H]$^{2+}$ |
| 13 | 1929 | 1876.08 | 626.6 | 626.4 | ⅓*[M + 3H]$^{3+}$ |
| 14 | 1931 | 1717.96 | 860.5 | 860.0 | ½*[M + 2H]$^{2+}$ |
| 15 | 1933 | 1819.96 | 911.1 | 911.0 | ½*[M + 2H]$^{2+}$ |
| 16 | 2007 | 1746.97 | 874.6 | 874.5 | ½*[M + 2H]$^{2+}$ |
| 17 | 2009 | 1615.97 | 809.1 | 809.0 | ½*[M + 2H]$^{2+}$ |
| 18 | 2010 | 1530.90 | 766.6 | 766.5 | ½*[M + 2H]$^{2+}$ |
| 19 | 2011 | 1090.68 | 1091.6 | 1091.7 | [M + H]$^{+}$ |
| 20 | 2013 | 1702.00 | 852.1 | 852.0 | ½*[M + 2H]$^{2+}$ |
| 21 | 2014 | 1705.89 | 854.1 | 854.0 | ½*[M + 2H]$^{2+}$ |
| 22 | 2015 | 1605.87 | 804.1 | 803.9 | ½*[M + 2H]$^{2+}$ |
| 23 | 2017 | 1648.90 | 825.1 | 825.5 | ½*[M + 2H]$^{2+}$ |
| 24 | 2022 | 1605.87 | 803.9 | 803.9 | ½*[M + 2H]$^{2+}$ |
| 25 | 2024 | 1605.87 | 803.9 | 803.9 | ½*[M + 2H]$^{2+}$ |
| 26 | 2028 | 1645.97 | 823.3 | 824.0 | ½*[M + 2H]$^{2+}$ |
| 27 | 2006 | 1847.05 | 935.7 | 935.5 | ½*[M + 2H]$^{2+}$ |
| 28 | 2012 | 1842.16 | 933.3 | 933.1 | ½*[M + H + Na]$^{2+}$ |
| 29 | 2020 | 1874.08 | 938.2 | 938.0 | ½*[M + 2H]$^{2+}$ |
| 30 | 2029 | 1856.16 | 929.0 | 929.1 | ½*[M + 2H]$^{2+}$ |
| 31 | 2025 | 2041.26 | 681.0 | 681.4 | ⅓*[M + 3H]$^{3+}$ |
| 32 | 2018 | 4548.49 | 1138.7 | 1138.1 | ¼*[M + 4H]$^{4+}$ |
| 33 | 2021 | 4536.59 | 1135.7 | 1135.8 | ¼*[M + 4H]$^{4+}$ |
| 34 | 2023 | 4184.38 | 1047.3 | 1047.1 | ¼*[M + 4H]$^{4+}$ |
| 35 | 2019 | 2158.14 | 1079.4 | 1080.1 | ½*[M + 2H]$^{2+}$ |
| 36 | 1916 | 1742.86 | 872.5 | 872.4 | ½*[M + 2H]$^{2+}$ |
| 37 | 1917 | 1683.83 | 843.0 | 842.9 | ½*[M + 2H]$^{2+}$ |
| 38 | 2030 | 2,366.18 | 1184.3 | 1184.1 | ½*[M + 2H]$^{2+}$ |
| 39 | 2016 | 2,128.22 | 717.7 | 717.1 | ⅓*[M + 2H + Na]$^{3+}$ |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes, including but not limited to the following references:

1. Golubovskaya V M, Kweh F A, Cance W G. Focal adhesion kinase and cancer. Histol Histopathol. 2009; 24(4):503-10. Epub 2009/02/19. PubMed PMID: 19224453.
2. Weiner T M, Liu E T, Craven R J, Cance W G. Expression of focal adhesion kinase gene and invasive cancer. Lancet. 1993; 342(8878):1024-5.
3. Owens L V, Xu L, Craven R J, Dent G A, Weiner T M, Kornberg L, Liu E T, Cance W G. Overexpression of the focal adhesion kinase (p125FAK) in invasive human tumors. Cancer Research. 1995; 55(13):2752-5.
4. Lark A L, Livasy C A, Calvo B, Caskey L, Moore D T, Yang X, Cance W G. Overexpression of focal adhesion kinase in primary colorectal carcinomas and colorectal liver metastases: immunohistochemistry and real-time PCR analyses. Clin Cancer Res. 2003; 9(1):215-22. PubMed PMID: 12538472.
5. Siesser P M F, Hanks S K. The Signaling and Biological Implications of FAK Overexpression in Cancer. Clin Cancer Res % R 101158/1078-0432CCR-06-0456. 2006; 12(11):3233-7.
6. McLean G W, Carragher N O, Avizienyte E, Evans J, Brunton V G, Frame M C. The role of focal-adhesion kinase in cancer—a new therapeutic opportunity. Nat Rev Cancer. 2005; 5(7):505-15. PubMed PMID: 16069815.
7. Schaller M D, Borgman C A, Cobb B S, Vines R R, Reynolds A B, Parsons J T. pp125fak a structurally distinctive protein-tyrosine kinase associated with focal adhesions. Proceedings of the National Academy of Sciences of the United States of America. 1992; 89(11):5192-6.
8. Zhao X, Guan J L. Focal adhesion kinase and its signaling pathways in cell migration and angiogenesis. Advanced drug delivery reviews. 2011; 63(8):610-5. Epub 2010/12/02. doi: 10.1016/j.addr.2010.11.001. PubMed PMID: 21118706; PMCID: 3132829.
9. Golubovskaya V M, Finch R, Cance W G. Direct Interaction of the N-terminal domain of Focal Adhesion Kinase with the N-terminal transactivation domain of p53. J Biol Chem. 2005; 280(26):25008-21. doi: 10.1074/jbc.M414172200.
10. Kurenova E, Xu L-H, Yang X, Baldwin A S, Jr., Craven R J, Hanks S K, Liu Z-g, Cance W G. Focal Adhesion Kinase Suppresses Apoptosis by Binding to the Death Domain of Receptor-Interacting Protein. Mol Cell Biol. 2004; 24(10):4361-71.
11. Lahlou H, Sanguin-Gendreau V, Zuo D, Cardiff R D, McLean G W, Frame M C, Muller W J. Mammary epithelial-specific disruption of the focal adhesion kinase blocks mammary tumor progression. Proc Natl Acad Sci USA. 2007; 104(51):20302-7. PubMed PMID: 18056629.
12. Pylayeva Y, Gillen K M, Gerald W, Beggs H E, Reichardt L F, Giancotti F G. Ras- and PI3K-dependent breast tumorigenesis in mice and humans requires focal adhesion kinase signaling. The Journal of Clinical Investigation. 2009; 119(2):252-66.
13. Nishimura M, Machida K, Imaizumi M, Abe T, Umeda T, Takeshima E, Watanabe T, Ohnishi Y, Takagi K, Hamaguchi M. Tyrosine phosphorylation of 100-130 kDa proteins in lung cancer correlates with poor prognosis. British Journal of Cancer. 1996; 74(5):780-7.
14. Recher C, Ysebaert L, Beyne-Rauzy O, Mansat-De Mas V, Ruidavets J-B, Cariven P, Demur C, Payrastre B, Laurent G, Racaud-Sultan C. Expression of Focal Adhesion Kinase in Acute Myeloid Leukemia Is Associated with Enhanced Blast Migration, Increased Cellularity, and Poor Prognosis. Cancer Res. 2004; 64(9):3191-7. doi: 10.1158/0008-5472.can-03-3005.
15. Ilic D, Furuta Y, Kanazawa S, Takeda N, Sobue K, Nakatsuji N, Nomura S, Fujimoto J, Okada M, Yamamoto T. Reduced cell motility and enhanced focal adhesion contact formation in cells from FAK-deficient mice. Nature. 1995; 377(6549):539-44. doi: 10.1038/377539a0. PubMed PMID: 7566154.
16. Xu L-h, Yang X-h, Bradham C A, Brenner D A, Baldwin A S, Craven R J, Cance W G. The focal adhesion kinase suppresses transformation-associated, anchorage-Independent apoptosis in human breast cancer cells. J Biol Chem. 2000; 275:30597-604.
17. Sonoda Y, Matsumoto Y, Funakoshi M, Yamamoto D, Hanks S K, Kasahara T. Anti-apoptotic Role of Focal Adhesion Kinase (FAK). INDUCTION OF INHIBITOR-OF-APOPTOSIS PROTEINS AND APOPTOSIS SUPPRESSION BY THE OVEREXPRESSION OF FAK IN A HUMAN LEUKEMIC CELL LINE, HL-60. J Biol Chem. 2000; 275(21):16309-15. PubMed PMID: 0010821872.
18. Kessler B E, Sharma V, Zhou Q, Jing X, Pike L A, Kerege A A, Sams S B, Schweppe R E. FAK Expression, Not Kinase Activity, Is a Key Mediator of Thyroid Tumorigenesis and Protumorigenic Processes. Mol Cancer Res. 2016; 14(9):869-82. Epub 2016/06/05. doi: 10.1158/1541-7786.MCR-16-0007. PubMed PMID: 27259715; PMCID: PMC5025360.
19. Walsh C, Tanjoni I, Uryu S, Tomar A, Nam J O, Luo H, Phillips A, Patel N, Kwok C, McMahon G, Stupack D G, Schlaepfer D D. Oral delivery of PND-1186 FAK inhibitor decreases tumor growth and spontaneous breast to lung metastasis in pre-clinical models. Cancer Biol Ther. 2010; 9(10):778-90. PubMed PMID: 20234193; PMCID: PMC2933309.
20. Stokes J B, Adair S J, Slack-Davis J, Walters D M, Tilghman R W, Hershey E D, Lowrey B, Thomas K S, Bouton A H, Hwang R F, Stelow E B, Parsons J T, Bauer T W. Inhibition of Focal Adhesion Kinase by PF-562,271 Inhibits the Growth and Metastasis of Pancreatic Cancer Concomitant with Altering the Tumor Microenvironment. Molecular Cancer Therapeutics. 2011. doi: 10.1158/1535-7163.mct-11-0261.
21. Cance W G, Golubovskaya V M. Focal adhesion kinase versus p53: apoptosis or survival?Sci Signal. 2008; 1(20): pe22. PubMed PMID: 18493017.
22. Xu L H, Yang X, Craven R J, Cance W G. The COOH-terminal domain of the focal adhesion kinase induces loss of adhesion and cell death in human tumor cells. Cell Growth Differ. 1998; 9(12):999-1005.
23. Marlowe T A, Lenzo F L, Figel S A, Grapes A T, Cance W G. Oncogenic Receptor Tyrosine Kinases Directly Phosphorylate Focal Adhesion Kinase (FAK) as a Resistance Mechanism to FAK-Kinase Inhibitors. Mol Cancer Ther. 2016; 15(12):3028-39. Epub 2016/09/18. doi: 10.1158/1535-7163.MCT-16-0366. PubMed PMID: 27638858; PMCID: PMC5136315.
24. Infante J R, Camidge D R, Mileshkin L R, Chen E X, Hicks R J, Rischin D, Fingert H, Pierce K J, Xu H, Roberts W G, Shreeve S M, Burris H A, Siu L L. Safety, pharmacokinetic, and pharmacodynamic phase I dose-escalation trial of PF-00562271, an inhibitor of focal adhesion kinase, in advanced solid tumors. J Clin Oncol. 2012; 30(13):1527-33. Epub 2012/03/29. doi: 10.1200/JCO.2011.38.9346. PubMed PMID: 22454420.
25. Jones S F, Siu L L, Bendell J C, Cleary J M, Razak A R, Infante J R, Pandya S S, Bedard P L, Pierce K J, Houk B, Roberts W G, Shreeve S M, Shapiro G I. A phase I study of VS-6063, a second-generation focal adhesion kinase inhibitor, in patients with advanced solid tumors. Invest New Drugs. 2015; 33(5):1100-7. doi: 10.1007/s10637-015-0282-y. PubMed PMID: 26334219.
26. Verastem I. Placebo Controlled Study of VS-6063 in Subjects With Malignant Pleural Mesothelioma (COMMAND 2015 [updated Oct. 5, 2015; cited 2016 Apr. 24, 2016]. Available from: clinicaltrials.gov/ct2/show/study/NCTO1870609.

27. Hoellerer M K, Noble M E, Labesse G, Campbell I D, Werner J M, Arold S T. Molecular recognition of paxillin LD motifs by the focal adhesion targeting domain. Structure. 2003; 11(10):1207-17. Epub 2003/10/07. PubMed PMID: 14527389.
28. Garron M L, Arthos J, Guichou J F, McNally J, Cicala C, Arold S T. Structural basis for the interaction between focal adhesion kinase and CD4. J Mol Biol. 2008; 375 (5):1320-8. Epub 2007/12/15. doi: 10.1016/j.jmb.2007.11.040. PubMed PMID: 18078954.
29. Xu S, Liu Y, Li X, Liu Y, Meijers R, Zhang Y, Wang J H. The binding of DCC-P3 motif and FAK-FAT domain mediates the initial step of netrin-1/DCC signaling for axon attraction. Cell Discov. 2018; 4:8. Epub 2018/02/27. doi: 10.1038/s41421-017-0008-8. PubMed PMID: 29479476; PMCID: PMC5818605.
30. Sieg D J, Hauck C R, Schlaepfer D D. Required role of focal adhesion kinase (FAK) for integrin-stimulated cell migration. J Cell Sci. 1999; 112(Pt):2677-91.
31. Sieg D J, Hauck C R, Ilic D, Klingbeil C K, Schaefer E, Damsky C H, Schlaepfer D D. FAK integrates growth-factor and integrin signals to promote cell migration. Nat Cell Biol. 2000; 2(5):249-56.
32. Thomas J W, Cooley M A, Broome J M, Salgia R, Griffin J D, Lombardo C R, Schaller M D. The role of FAK binding in the regulationof tyrosine phosphorylation of paxillin. J Biol Chem. 1999; in press.
33. Kaneda T, Sonoda Y, Ando K, Suzuki T, Sasaki Y, Oshio T, Tago M, Kasahara T. Mutation of Y925F in focal adhesion kinase (FAK) suppresses melanoma cell proliferation and metastasis. Cancer Lett. 2008; 270(2):354-61. Epub 2008/07/09. doi: 10.1016/j.canlet.2008.05.042. PubMed PMID: 18606490.
34. Deramaudt T B, Dujardin D, Noulet F, Martin S, Vauchelles R, Takeda K, Ronde P. Altering FAK-paxillin interactions reduces adhesion, migration and invasion processes. PLoS One. 2014; 9(3):e92059. Epub 2014/03/20. doi: 10.1371/journal.pone.0092059. PubMed PMID: 24642576; PMCID: PMC3958421.
35. Kanteti R, Batra S K, Lennon F E, Salgia R. FAK and paxillin, two potential targets in pancreatic cancer. Oncotarget. 2016; 7(21):31586-601. Epub 2016/03/17. doi: 10.18632/oncotarget.8040. PubMed PMID: 26980710; PMCID: PMC5058780.
36. Scheswohl D M, Harrell J R, Rajfur Z, Gao G, Campbell S L, Schaller M D. Multiple paxillin binding sites regulate FAK function. J Mol Signal. 2008; 3:1. Epub 2008/01/04. doi: 10.1186/1750-2187-3-1. PubMed PMID: 18171471; PMCID: PMC2246129.
37. Gao G, Prutzman K C, King M L, Scheswohl D M, DeRose E F, London R E, Schaller M D, Campbell S L. NMR solution structure of the focal adhesion targeting domain of focal adhesion kinase in complex with a paxillin LD peptide: evidence for a two-site binding model. J Biol Chem. 2004; 279(9):8441-51. PubMed PMID: 14662767.
38. Bertolucci C M, Guibao C D, Zheng J. Structural features of the focal adhesion kinase-paxillin complex give insight into the dynamics of focal adhesion assembly. Protein Sci. 2005; 14(3):644-52. Epub 2005/02/04. doi: 10.1110/ps.041107205. PubMed PMID: 15689512; PMCID: PMC2279287.
39. Chang Y S, Graves B, Guerlavais V, Tovar C, Packman K, To K H, Olson K A, Kesavan K, Gangurde P, Mukherjee A, Baker T, Darlak K, Elkin C, Filipovic Z, Qureshi F Z, Cai H, Berry P, Feyfant E, Shi X E, Horstick J, Annis D A, Manning A M, Fotouhi N, Nash H, Vassilev L T, Sawyer T K. Stapled alpha-helical peptide drug development: a potent dual inhibitor of MDM2 and MDMX for p53-dependent cancer therapy. Proc Natl Acad Sci USA. 2013; 110(36):E3445-54. Epub 2013/08/16. doi: 10.1073/pnas.1303002110. PubMed PMID: 23946421; PMCID: PMC3767549.
40. Gao H, Wu Y, Sun Y, Yang Y, Zhou G, Rao Y. Design, Synthesis, and Evaluation of Highly Potent FAK-Targeting PROTACs. ACS Med Chem Lett. Article ASAP. DOI: 10.1021/acsmedchemlett.9b00372

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A composition comprising a compound comprising Myristoyl-NLR$_8$ELDRLLS$_5$ELN-NH$_2$ (SEQ ID NO: 28), wherein in the peptide NLR$_8$ELDRLLS$_5$ELN-NH$_2$ (SEQ ID NO: 28), R$_8$ is (R)-2-(7-octenyl)alanine, S$_5$ is (S)-2-(4-pentenyl)alanine, and R$_8$ and S$_5$ have undergone a ring-closure metathesis reaction to yield the structure:

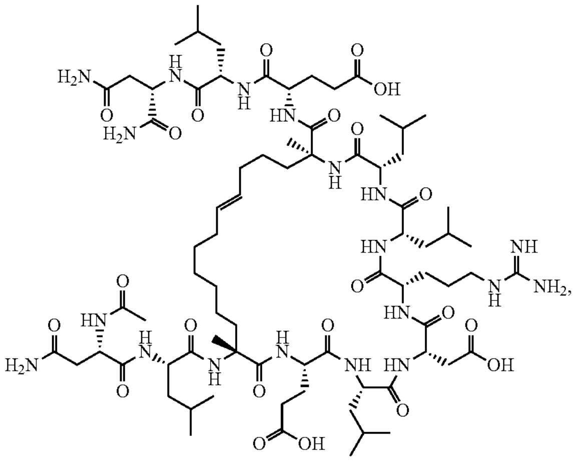 [SMILES: CC(=O)N[C@@H](CC(N)=O)C(=O)N[C@@H](CC(C)C)C(=O)N[C@]1(C)CCCCCC/C=C/CCC[C@@](C)(C(=O)N[C@@H](CCC(=O)O)C(=O)N[C@@H](CC(C)C)C(=O)N[C@@H](CC(N)=O)C(N)=O)NC(=O)[C@H](CC(C)C)NC(=O)[C@H](CC(C)C)NC(=O)[C@H](CCCNC(=N)N)NC(=O)[C@H](CC(=O)O)NC(=O)[C@H](CC(C)C)NC(=O)[C@H](CCC(=O)O)NC1=O]

and

Myristoyl is covalently attached to the N-terminal amino group.

2. The composition of claim 1, the compound is further conjugated with an additional therapeutic agent.

3. The composition of claim 1, wherein the compound is further conjugated with an imaging agent.

4. The composition of claim 3, wherein the imaging agent is (5-/6-)carboxytetramethylrhodamine (TAMRA).

5. A method of treating, ameliorating, or preventing a hyperproliferative disease or fibrosis in a patient comprising administering to said patient a therapeutically effective amount of a composition of claim 1.

6. The method of claim 5, wherein said hyperproliferative disease is cancer, wherein said cancer is a cancer characterized with FAK expression, FAK pathway activation, FAK dependence, FAK activity and/or FAK-paxillin related activity;

wherein said patient is a human patient.

7. The method of claim 5, further comprising administering to said patient one or more anticancer agents selected from a chemotherapeutic agent and radiation therapy.

8. A composition of claim 1, wherein the composition is a pharmaceutical composition and wherein the compound is within a liposomal formulation.

9. The pharmaceutical composition of claim 8, wherein the liposomal formulation comprises HSPC, Cholesterol, PEG2000-DSPE, DSPC, DOPE, DOTAP, Triolein, EPC, DOPS, POPC, SM, DMPC, DMPG, DOPC, mPEG derivatives, MVL5, DOTMA, DDAB, DC-Cholesterol, GL67, DODMA, Soy phospholipids, cationic lipids, anionic lipids, and/or neutral lipids.

* * * * *